US012758545B2

(12) United States Patent
(10) Patent No.: US 12,758,545 B2
(45) Date of Patent: Oct. 13, 2026

Bouyssou et al.

(54) INHIBITORS OF TRPC6 FOR TREATING RESPIRATORY CONDITIONS

(71) Applicant: Boehringer Ingelheim International GmbH, Ingelheim am Rhein (DE)

(72) Inventors: Thierry Bouyssou, Warthausen (DE); Abhya Gupta, Biberach an der Riss (DE); Paul Nicklin, Biberach an der Riss (DE); Nima Soleymanlou, Maple (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 885 days.

(21) Appl. No.: 17/914,773

(22) PCT Filed: Apr. 14, 2021

(86) PCT No.: PCT/EP2021/059683

§ 371 (c)(1),
(2) Date: Sep. 27, 2022

(87) PCT Pub. No.: WO2021/209510

PCT Pub. Date: Oct. 21, 2021

(65) Prior Publication Data

US 2023/0149393 A1 May 18, 2023

(30) Foreign Application Priority Data

Apr. 16, 2020 (EP) .................................... 20169943
Oct. 23, 2020 (EP) .................................... 20203583

(51) Int. Cl.

| | |
|---|---|
| ***A61K 31/496*** | (2006.01) |
| ***A61K 31/4523*** | (2006.01) |
| ***A61K 31/46*** | (2006.01) |
| ***A61K 31/501*** | (2006.01) |
| ***A61K 31/5386*** | (2006.01) |

(52) U.S. Cl.

CPC ........ *A61K 31/496* (2013.01); *A61K 31/4523* (2013.01); *A61K 31/46* (2013.01); *A61K 31/501* (2013.01); *A61K 31/5386* (2013.01)

(58) Field of Classification Search

CPC .. A61K 31/496; A61K 31/4523; A61K 31/46; A61K 31/501; A61K 31/5386

See application file for complete search history.

(56) References Cited

U.S. PATENT DOCUMENTS

| | | | | |
|---|---|---|---|---|
| 6,673,799 | B1 | 1/2004 | Taniguchi et al. | |
| 7,196,080 | B2 | 3/2007 | Iwata et al. | |
| 7,220,744 | B2 | 5/2007 | Jolidon et al. | |
| 7,317,125 | B2 | 1/2008 | Bolin et al. | |
| 7,332,495 | B2 | 2/2008 | Li et al. | |
| 7,473,787 | B2 | 1/2009 | McHardy et al. | |
| 7,557,114 | B2 | 7/2009 | Jolidon et al. | |
| 7,951,836 | B2 | 5/2011 | Jolidon et al. | |
| 8,188,139 | B2 | 5/2012 | Jolidon et al. | |
| 8,288,435 | B2 | 10/2012 | Aissaoui et al. | |
| 8,497,289 | B2 | 7/2013 | Lindsley et al. | |
| 8,816,079 | B2 | 8/2014 | Maeda et al. | |
| 10,800,757 | B2 * | 10/2020 | Bouyssou ............ | C07D 213/04 |
| 10,889,568 | B2 * | 1/2021 | Bouyssou ............ | C07D 213/04 |
| 11,485,740 | B2 * | 11/2022 | Brunette .............. | C07D 405/14 |
| RE49,699 | E * | 10/2023 | Bouyssou ............ | C07D 401/14<br>544/238 |
| 12,156,874 | B2 * | 12/2024 | Gottschling ............ | A61P 25/00 |
| 2004/0016224 | A1 | 1/2004 | Haaken et al. | |
| 2006/0167000 | A1 | 7/2006 | Barnham et al. | |
| 2007/0021472 | A1 | 1/2007 | Zhu et al. | |
| 2008/0280916 | A1 | 11/2008 | Bilich et al. | |
| 2008/0287455 | A1 | 11/2008 | Jolidon et al. | |
| 2010/0035914 | A1 | 2/2010 | Bertani et al. | |
| 2010/0234603 | A1 | 9/2010 | Linghu et al. | |

(Continued)

FOREIGN PATENT DOCUMENTS

| | | | |
|---|---|---|---|
| CL | 2020001097 | A1 | 8/2020 |
| CN | 1381449 | A | 11/2002 |

(Continued)

OTHER PUBLICATIONS

Yang, Oncotarget, 2017, 8:5123-5134 (Year: 2017).*
Remick, Infection and Immunity, May 2005, 2751-2757 (Year: 2005).*
Annane, Annals of Intensive Care, Apr. 13, 2011; 1:7) (Year: 2011).*
Human Protein Atlas, TRPC6 Expression in Cancer, https://web.archive.org/web/20160804013702/https://www.proteinatlas.org/ENSG00000137672-TRPC6/cancer (Year: 2016).*
Thornber, Chemical Society Reviews, Issue 4, 1979 (Year: 1979).*
Abstract CN103360343 cited herein.
Abstract WO2009139576 cited herein.
Alessandri-Haber, Nicole, et al. "TRPC1 and TRPC6 Channels Cooperate with TRPV4 to Mediate Mechanical Hyperalgesia and Nociceptor Sensitization", The Journal of Neuroscience, (2009) vol. 29, 6217-6228.

(Continued)

*Primary Examiner* — Andrew D Kosar
*Assistant Examiner* — Phillip Matthew Rzeczycki
(74) *Attorney, Agent, or Firm* — David L. Kershner

(57) ABSTRACT

The invention relates to methods for treating a disorder associated with vascular hyperpermeability and/or conditions arising therefrom, comprising administering to a patient in need thereof a pharmaceutically effective amount of a TRPC6 inhibitor of formula (I), or pharmaceutically acceptable salts thereof, wherein $R^1$ to $R^7$, A, Y and L are as defined herein.

(I)

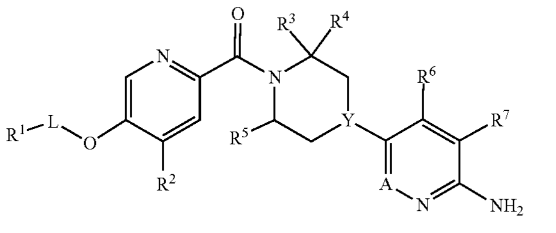

23 Claims, 1 Drawing Sheet

(56) References Cited

U.S. PATENT DOCUMENTS

| | | | |
|---|---|---|---|
| 2011/0257196 A1 | 10/2011 | Lu et al. |
| 2012/0022099 A1 | 1/2012 | Zlotnikov et al. |
| 2015/0087673 A1 | 3/2015 | Hitoshi et al. |
| 2015/0218165 A1 | 8/2015 | Frey et al. |
| 2019/0169167 A1 | 6/2019 | Bouyssou et al. |
| 2020/0399282 A1 | 12/2020 | Brunette et al. |
| 2021/0053935 A1 | 2/2021 | Berry et al. |
| 2021/0163449 A1 | 6/2021 | Bouyssou et al. |
| 2021/0270343 A1 | 9/2021 | Battlogg |

FOREIGN PATENT DOCUMENTS

| | | | |
|---|---|---|---|
| CN | 1516691 | A | 7/2004 |
| CN | 103360343 | A | 10/2013 |
| CN | 103694242 | A | 4/2014 |
| CN | 106317050 | A | 1/2017 |
| CN | 107176927 | A | 9/2017 |
| CN | 107253952 | A | 10/2017 |
| CN | 107540636 | A | 1/2018 |
| EP | 1396487 | A1 | 3/2004 |
| EP | 1396487 | B1 | 12/2008 |
| EP | 2556820 | A2 | 2/2013 |
| EP | 2556829 | A1 | 2/2013 |
| JP | 2003064057 | A | 3/2003 |
| JP | 2007500715 | A | 1/2007 |
| JP | 2007254391 | A | 10/2007 |
| JP | 2008239568 | A | 10/2008 |
| JP | 2008540594 | A | 11/2008 |
| JP | 2013107881 | A | 6/2013 |
| JP | 2013116858 | A | 6/2013 |
| JP | 2013536873 | A | 9/2013 |
| JP | 2014528921 | A | 10/2014 |
| JP | 2016520105 | A | 7/2016 |
| JP | 2021008503 | A | 1/2021 |
| JP | 2021500390 | A | 1/2021 |
| JP | 2021513966 | A | 6/2021 |
| JP | 2021513984 | A | 6/2021 |
| JP | 6979502 | B2 | 12/2021 |
| TW | 201930264 | A | 8/2019 |
| WO | 1991009594 | A1 | 7/1991 |
| WO | 1993000313 | A2 | 1/1993 |
| WO | 1994012461 | A1 | 6/1994 |
| WO | 2000017163 | A1 | 3/2000 |
| WO | 2002008221 | A2 | 1/2002 |
| WO | 2002102778 | A1 | 12/2002 |
| WO | 2003090752 | A1 | 11/2003 |
| WO | 2004089363 | A1 | 10/2004 |
| WO | 2005011653 | A2 | 2/2005 |
| WO | 2005037216 | A2 | 4/2005 |
| WO | 2006044174 | A2 | 4/2006 |
| WO | 2006106425 | A1 | 10/2006 |
| WO | 2007053394 | A1 | 5/2007 |
| WO | 2007075629 | A2 | 7/2007 |
| WO | 2007129745 | A1 | 11/2007 |
| WO | 2008110611 | A1 | 9/2008 |
| WO | 2009016560 | A2 | 2/2009 |
| WO | 2009139576 | A2 | 11/2009 |
| WO | 2010078348 | A1 | 7/2010 |
| WO | 2010080357 | A1 | 7/2010 |
| WO | 2010116328 | A2 | 10/2010 |
| WO | 2010150281 | A2 | 12/2010 |
| WO | 2011019798 | A1 | 2/2011 |
| WO | 2011044001 | A1 | 4/2011 |
| WO | 2011062939 | A1 | 5/2011 |
| WO | 2011109059 | A1 | 9/2011 |
| WO | 2011136292 | A1 | 11/2011 |
| WO | 2011143365 | A1 | 11/2011 |
| WO | 2012016217 | A1 | 2/2012 |
| WO | 2012037349 | A2 | 3/2012 |
| WO | 2012158784 | A2 | 11/2012 |
| WO | 2013014185 | A1 | 1/2013 |
| WO | 2013017657 | A1 | 2/2013 |
| WO | 2013066714 | A1 | 5/2013 |
| WO | 2014139144 | A1 | 9/2014 |
| WO | 2014191336 | A1 | 12/2014 |
| WO | 2014192865 | A1 | 12/2014 |
| WO | 2015048547 | A2 | 4/2015 |
| WO | 2015101957 | A2 | 7/2015 |
| WO | 2015199206 | A1 | 12/2015 |
| WO | 2016073774 | A2 | 5/2016 |
| WO | 2016138114 | A1 | 9/2016 |
| WO | 2016138144 | A2 | 9/2016 |
| WO | 2017066705 | A1 | 4/2017 |
| WO | 2017161028 | A1 | 9/2017 |
| WO | 2017222930 | A1 | 12/2017 |
| WO | 2018159827 | A1 | 9/2018 |
| WO | 2018170225 | A1 | 9/2018 |
| WO | 2018183145 | A1 | 10/2018 |
| WO | 2019046931 | A1 | 3/2019 |
| WO | 2019079578 | A1 | 4/2019 |
| WO | 2019081637 | A1 | 5/2019 |
| WO | 2019161010 | A1 | 8/2019 |
| WO | 2019169168 | A1 | 9/2019 |
| WO | 2020208002 | A1 | 10/2020 |
| WO | 2020223419 | A1 | 11/2020 |
| WO | 2021209510 | A1 | 10/2021 |

OTHER PUBLICATIONS

Antigny, Fabrice et al., "Transient Receptor Potential Canonical Channel 6 Links Ca2+ Mishandling to Cysytic Fibrosis Transmembrane Conductance Regulator Channel Dysfunction in Cystic Fibrosis", Am J. Resp Cell Mol. Biol., (2011) vol. 44, 83-90.

Baldovini, N. et al. "3-Oxa- and 3-Azabicyclo[3.1.0]hexan-2-ones via Tandem Radical Cyclization-Intramolecular Sn2 Reactions", J of Organic Chemistry, (1996), vol. 61, 3205-3208.

Bergdahl, Andreas et al., "Plasticity of TRPC expression in arterial smooth muscle: correlation with store-operated CA2+ entry", Am. J. Cell Physiol, (2005) vol. 288, C872-C880.

Berge, Stephen et al., "Pharmaceutical Salts", J. Pharm. Sci, (1977), vol. 66, 1-19.

Chaudhuri, Pinaki et al., "Elucidation of a TRPC6-TRCP5 Channel Cascade that Restricts Endothelial Cell Movement", Mole. Biol. of the Cell, (2008) vol. 19, 3203-3211.

Chigurupati, Srinivasulu et al, "Receptor Channel TRPC6 is a Key Mediator of Notch Driven Glioblastoma Growth and Invasiveness", Cancer Research, (2009) 70(1), 418-427.

Clapham, David E. et al., "TRP channels as cellular sensors" Pharmacol Review, (2003) vol. 55, vol. 4, 591-596.

Clapham, David E. et al. "The TPR Ion Channel Family", (2001) Nat. Rev. Neuro Sci, 387-396.

Clapham, David et al., "International Union of Pharmacology, XLIII. Compendium of Voltage-Gated Ion Channels: Transient Receptor Potential Channels" Pharmacological Reviews, (2004) vol. 55, 2003, 7 pages.

Clarson, L.H. et al. "Store operated Ca2+ entry in first trimester and term human placenta", J. Physiol., (2003) vol. 2, 515-528.

Clinical Trials, NCT02832037, Clinical Trial of BI425809 Effect on Cognition and Functional Capacity in Schizophrenia, A phase II Randomised, Double Blind, Placebo controlled Parallel group trial, May 20, 2020, 6 pages.

Davis, Jennifer et al., A TRPC6-Dependent Pathway for Myofibroblast Transdifferentiation and Wound Healing in Vivo, Developmental Cell, (2012) vol. 23, 705-715.

De Quiros, Sandra Bernaldo et al. "Identification of TRPC6 as a possible candidate target gene with an amplicon at 11q21-q22.2 for migratory capcity in head and neck squamous cell carcinomas", BMC Cancer, (2013) vol. 13, 116, 11 pgs.

Desai, Bimal N. et al., "TRP channels and mice deficient in TRP channels", Eur. J. Physiol. (2005) vol. 451, 11-18.

Dhennin-Duthille, Isabelle et al., "High Expression of Transient Receptor Potential Channels in Human Breast Cancer Epithelial Cells and Tissues: Correlation with Pathological Parameters", Cellular Physiology and Biochemistry, (2011) vol. 28, 813-822.

Ding, Mingmin et al, "Pyrazolo [1,5-a] pyrimidine TRP6 antagonists for the treatment of gastric cancer", Cancer Letters, (2018) 432, 47-55.

(56) References Cited

OTHER PUBLICATIONS

Ding, Xia et al., "Essential Role of TRPC6 Channels in G2/M Phase Transition and Development of Human Glioma", JNCI, (2010) vol. 102, 1052-1068.
Eckel, Jason et al., "TRPC6 Enhances Angiostentin II-induced Albuminuria", JASN, (2011) vol. 22, 526-535.
Finney-Hayward, Tricia K. et al., "Expression of Transient Receptor Potential C6 Channels in Human Lung Macrophages", Am. J. Respir. Cell Mol. Biol., (2010) vol. 43, 296-304.
Gilligan et al., Divergent mechanisms for the Dealkoxycarbonylation of a 2-(3-Azetidiny)malonate by Chloide and Cyanide, Tetrahedron Letters, 1994, vol. 35, No. 21, pp. 3441-3444.
Hafner, Stephanie et al. "A (+) Larixol Congener with High Affinity and Subtype Selectivity toward TRP6", ChemPubSoc Europe, (2018) vol. 13, 1028-1035.
Hofmann, Katharina et al, "Classical transient receptor potential 6 (TRPC6) channels support myofibroblast differentiation and development of experimental pulmonary fibrosis", Biochemica, (2017) vol. 1863, 560-568.
Hofmann, Thomas et al, "Direct activation of human TRPC6 and TRP3 channels by diacylglycerol", Nature (1999), vol. 397, 259-263.
Holz, Investigational Treatment for Cognitive Impairment Associated with Schizophrenia receives FDA Breakthrough therapy designation, Press Release, BI, from May 24, 2021.
International Preliminary Report on Patentability for PCT/EP2021/059683 mailed Oct. 27, 2022.
International Report on Patentability, PCT/US2019/017939 mailed Aug. 20, 2020.
International Search Report and Written Opinion for PCT/EP2018/079276 mailed Oct. 25, 2018.
International Search Report and Written Opinion for PCT/EP2018079276.
International Search Report and Written Opinion for PCT/EP2019/053525 mailed Apr. 10, 2019.
International Search Report and Written Opinion for PCT/EP2021/059683 mailed Jun. 29, 2021.
International Search Report and Written Opinion for PCT/EP2022/078609 mailed Jan. 25, 2023.
International Search Report and Written Opinion for PCT/US2019/017939 mailed May 18, 2020.
International Search Report and Written Opinion, PCT/EP2012/065140, mailed Aug. 27, 2012.
International Search Report PCT/EP2020/059854 mailed May 2, 2019.
International Search Report PCT/US2019/017939 mailed May 15, 2019.
Iyer, Soumya et al. "Receptor channel TRPC6 orchestrate the activation of human hepatic stellate cell under hypoxia condition", Experimental Cell Research, (2015) vol. 336, 66-75.
Jacobs, Chaja F. et al, "Kinase inhibitors developed for treatment of hematologic malignancies implications for immune modulation in COVID-19", Blood Advan., (2021) vol. 5, 913-925.
Johansson, S.E. et al., "Cerebrovascular endothelin I hyperreactivity is associated with transient receptor potential canonical channels 1 and 6 activation and delayed cerebral hypoperfusion after forebrain ischachemia in rats", Acta Pysiol, (2015) 214, 376-389.
Krall, Paola et al, "Podocyte-Specific Overexpression of Wild Type or Mutant TRPC6 in Mice is Sufficient to cause Glomerular Disease", PLOS, (2010) vol. 5, Issue 9, e12859, 11 pgs.
Ku, Chun-Ying et al, "Expression of Transient Receptor Channel Proteins in Human Fundal Myometrium in Pregnancy", J Soc Gynecol Investig, (2006) vol. 13, No. 3, 217- 225.
Kunichika, Naomi et al., "Bosentan Inhibits Transient Receptor Potential Channel Expression in Pulmonary Vascular Myocytes", Am J. Respir. Crit. Care Med., (2004) vol. 170, 1101-1107.
Kuwahara, Koichiro et al., "TRPC6 fulfills a calcineurin signalling circuit during pathologic cardiac remodeling", Journal of Clinical Investigation, (2006) vol. 116, No. 12, 3113-3126.
Lei, Lei et al., "The role of mechanical tension on lipid raft dependent PDGF-induced TRPC6 activation", Biomaterials, (2014) vol. 35, 2868-2877.
Levy, Mitchell et al., "2001 SCCM/EICM/ACCP/ATS/SIS International Sepsis Definitions Conference", Crit. Care Med, (2003) vol. 31, 1250-1256.
Lin, Brian Lee et al, "In vivo selective inhibition of TRPC6 by antagonist BI 749327 ameliorates fibrosis and dysfunction in cardiac and renal disease", PNAS, (2019) vol. 116, No. 20, 10156-10161.
Maier, T. et al. "Discovery and Pharmacological Characterization of a Novel Potent Inhibitor of Diacylglycerol-senistive TRPC cation channels", British Journal of Pharmacology, (2015) 172, 3650-3660.
Medda et al., 3,4-Methano-ß -Proline: A Conformationally Constrained ß-Amino Acid, Synlett, vol. 2009, No. 06, p. 921-924.
Miripour, Zohreh S. et al, "Real time diagnosis of reactive oxygen species (ROS) in fresh sputum by electrochemical tracing; correlation between COVID-19 and viral-induced ROS in lung/respiratory epithelium during this pandemic" Biosensors and Bioelectronics, (2020) vol. 165, 6 pages.
Moller, Clemens C. et al. "Induction of TRPC6 Channel in Acquired Forms of Proteneuric Kidney Disease", J. Am. Socio Nephrol. (2007) vol. 18, 29-36.
Moschetti, Viktoria et al, "Safety, Tolerability, and Pharmacokinetics of Oral BI 425809, a Glycine Transporter 1 Inhibitor, in Healthy Male Volunteers: A Partially Randomised, Single-Blind, Placebo-Controlled, First in Human Study" Eur. J. Drug Metab Pharmacokinet. (2018) vol. 43, 239-249.
Motoyama, Keisuke et al, Discovery of a bicyclo [4.3.0] nonane DS88790512 as a potent, selective, and orally bioavailable blocker of transient receptor potential canonical 6 (TRPC6), Bioorganic & Medicinal Chem Letters, (2018) 28, 2222-2227.
Reiser, Jochen et al, "TRPC6 is a glomular slit diaphragm association channel required for normal renal function", Nature Genetics, (2009) vol. 37, No. 7, 739-744.
Rosenbaum, Michael A. et al. "Hypercholesterolemia inhibits Reendothelialization of Arterial Injuries by TRPC Channel Activation", J. Vasc. Surg., (2015) vol. 62, 4, 1040-1047.
Sadowski, Carolin et al., "A Single-Gene Cause in 29.5% of Cases of Steroid-Resistant Nephrotic Syndrome", JASN, (2015) vol. 26, 1279-1289.
Sawamura, Seishiro et al, "Screening of Transient Receptor Potential Canonical Channel Activators Identifies Novel Neurotrophic Piperazine Compounds", Molecular Pharmacology, (2016) vol. 89, 348-363.
Schlondorff, Johannes et al., "TRPC6 mutations associated with focal segmental glomerulosclerosis cause constitutive activation of NFAT-dependent transcription", Am J. Physiol Cell Physiol, (2009) vol. 296, C558-C569.
Seo, Kinya et al, "Combined TRPC3 and TRPC6 blockade by selective small-molecule or genetic deletion inhibits pathological cardiac myopathy", PNAS, (2014) vol. 111, No. 4, 1551-1556.
Seo, Kinya et al, "Hyperactive Adverse Mechanical Stress Responses in Dystrophic Heart are Coupled to Transient Receptor Potential Canonical 6 and Blocked by cGMP-Protein Kinase G Modulation" Circulation Research, (2014) 823-832.
Sharma, Swagat, et al. "Review of Transient Receptor Potential Canonical (TRPC5) Channel Modulators and Diseases", Journal of Medicinal Chemistry, (2019) a-n.
Song, Jiayin et al., "Critical Role of TRPC6 channels in the development of human renal cell carcinoma", Mol. Biol. Rep. (2013) vol. 40, 5115-5122.
Tauseef, Mohammad et al. "TLR4 activation of TRPC6-dependent calcium signaling mediates endotoxin-induced lung vascular permeability and inflammation", JEM, vol. (2012) vol. 209, No. 11, 1953-1968.
Thilo, Florian et al, "Pulsatile Atheroprone Shear Stress Affects the Expression of Transient Receptor Potential Channels in Human Endothelial Cells", Hypertension, (2012) 1232-1240.
Thilo, Florian et al, "VEGF regulates TRPC Channels in Podocytes", Nephrol. Dial. Transplant, (2012) vol. 27, 921-929.

(56) References Cited

OTHER PUBLICATIONS

Urban, Nicole et al, "Identification and Validation of Larixyl Acetate as a Potent TRPC6 Inhibitor", Molecular Pharmacology, (2015) 89, 197-213.
Wan, Qi et al, "Expression of transient receptor potential channel 6 in cervical cancer", Onco Targets and Therapy, (2012) vol. 5, 171-176.
Wang, Jian et al, "Effects of chronic exposure to cigarette smoke on cannonical transient receptor potential expression in rat pulmonary arterial smooth muscle", Am. J. Physiol Cell Physiol, (2014) vol. 306, C364-C373.
Washburn, David G. et al., "The discovery of potent blockers of the canonical transient receptor channels TRPC3 and TRPC6, based on an anilino-thiazole pharmacophore", Bioorganic & Medicinal Chemistry Letters, (2013) 23, 4979-4984.
Weissmann, Norbert et al., "Activation of TRP6 channels is essential for lung ischaemia-reperfusion induced oedema in mice", Nature Communications, (2011) 649-658.
Wen, Liang et al. "Regulation of multi drug resistance in hepatocellular carcinoma cells is TRPC6/Calcium dependent", Scientific Reports, (2015) 1-14.
Winn, Michelle et al., "A Mutation in the TRPC6 Cation Channel causes Familial Focal Segmental Glomerulosclerosis", www.sciencemag.org, vol. 38, (2005) 1801-1804.
Wu, Xu et al, "TRPC channels are necessary mediators of pathologic cardiac hypertrophy", PNAS, (2010) vol. 107, No. 15, 7000-7005.
Wu, Yueh-Lin et al., "Inhibition of TRPC6 Channels Ameliorates Renal Fibrosis and Contributes to Renal Protection by Soluble Klotho", Kidney International, (2016) 1-12.
Xie, Jian et al., "Cardioprotection by Klotho through downregulation of TRPC6 channels in the mouse heart", Nature Communications, (2012) 11 pgs.
Xie, Jian et al., "Soluble Klotho Protects against Uremic Cardiomyopathy independently of Fibroblast Growth Factor 23 and Phophate", JASN, (2015) vol. 26, 1150-1160.
Yu, Ying et al, "A functional single nucleotide polymorphism in the TRPC6 gene promoter associated with idiopathic pulmonary arterial hypertension", Circulation, (2009) vol. 119, 2313-2322.
Yu, Ying et al., "Enhanced expression of transient receptor potential channels in idiopathic pulmonary arterial hypertension", PNAS, (2004), vol. 101, No. 38, 13861-13866.
Zhang, Shui-Shen et al., "High expression of transient potential receptor C6 correlated with poor prognosis in patients with esophageal squamous cell carcinoma", Med. Oncol., (2013) 30:607, 8 pgs.
Zhang, Yong et al, "MicroRNA-26a prevents endothelial cell apoptosis by directly targeting TRPC6 in the setting of atherosclerosis", Nature, (2015), 5:9401, 10 pgs.
Abstract WO2009139576A2 cited herein.
Canales, Cesar P. et al. "Characterization of a Trpc6 Transgenic Mouse Associated with Early Onset FSCS" BR J Med Med Res, (2015) 5 (10) 1198-2012.
Clapham D.E., "TRP Channels as Cellular Sensors," Nature, Dec. 4, 2003, vol. 426, No. 6966, pp. 517-524, Review.
Dietrich, Alexander et al. "TRPC6: Physiological Function and Pathophysiological Relevance," Mammalian Transient Receptor Potential (TRP) Cation Channels, (2014) vol. 222, 157-188.
Extended European Search Report for European Application No. 20197194.2, dated Feb. 3, 2021, 5 Pages.
Geven, Christopher et al. "Effects of the Humanized Anti-Adrenomedullin Antibody Adrecizumab (HAM8101) on Vascular Barrier Function and Survival in Rodent Models of Systemic Inflammation and Sepsis" Shock, (2018) vol. 50, No. 6, 648-654.
Gipson, Debbie et al. "Clinical trial of focal segmental glomerulosclerosis in children and young adults" (2011) Kidney International, vol. 80, 868-878.
Haas, Mark et al. "Changing Etiologies of Unexplained Adult Nephrotic Syndrome: A Comparison of Renal Biopsy Findings from 1976-1979 and 1995-1997" (1997) American Journal of Kidney Diseases, 30(5), 621-631.
Inker, Lesley A. et al. "Estimating Glomerular Filtration Rate from Serum creatinine and Cystatin C" (2012) New England Journal of Medicine, vol. 367, 20-29.
International Search Report and Written Opinion for International Application No. PCT/US2024/042613, dated Oct. 25, 2024, 12 Pages.
Jiang, Lina et al. "Over-expressing transient receptor potential cation channel 6 in podocytes induces cytoskeleton rearrangement through increases of intracellular Ca2+ and RhoA activation" (2011) Experimental Biology and Medicine, 236, 184-193.
KDIGO: "Clinical Practice Guideline for Acute Kidney Injury," Kidney International, Mar. 2012, Supplement. 1, vol. 2, pp. 1-138,(141 Pages).
Kiffel, Jeremy et al. "Focal Segmental Glomerulosclerosis and Chronic Kidney Disease in Pediatric Patients" (2011) Adv Chronic Kidney Dis, 18(5) 332-338.
Kitiyakara, Chagriay et al. "Twenty-One-Year Trend in ESRD due to Focal Segmental Glomerulosclerosis in the United States" (2004) American Journal of Kidney Disease, 44(5), 815-825.
Levey, Andrew et al. "Glomerular Filtration Rate and Albuminuria for Detection and Staging of Acute and Chronic Kidney Disease in Adults A Systematic Review" (2015) JAMA, vol. 313, 8, 837-846.
Mcmullan, Ross R. et al. "Vascular leak in Sepsis: Physiological basis and potential therapeutic advances" Critical Care, (2024) 28, 97, 15 pgs.
Rosenberg, Avi et al. "Focal Segmental Glomerulosclerosis" (2017) Clin J Am Soc Nephrol, vol. 12, 502-517.
Tian, Dequan et al. "Antagonistic Regulation of Actin Dynamics and Cell Motility by TRPC5 and TRPC6 Channels" (2010) Sci Signal, 3(145), 1-25.
Written Opinion for International Application No. PCT/EP2020/059854, dated May 29, 2020, 5 Pages.
Wuts P., et al., "Protection for the Amino Group," Greene's Protective Groups in Organic Synthesis, Apr. 2006, 696-926, DOI: 10.1002/9780470053485.ch7.
Xiaowen F., "Pharmacy Classroom Notes," Yaojixue Ketang Biji, People's Military Medical Press, 2011, p. 222, (3 Pages), (Jan. 2011).
Zhou, Baoping et al. "Ribemansides A and B, TRPC6 Inhibitors from Ribes manshuricum That Suppress TGF-β1-Induced Fibrogenesis in HK-2 Cells" Journal of Natural Products, 2018, vol. 81, No. 4, 913-917.

* cited by examiner

INHIBITORS OF TRPC6 FOR TREATING RESPIRATORY CONDITIONS

FIELD OF THE INVENTION

The present invention relates to methods for the treatment of disorders associated with vascular hyperpermeability and conditions arising therefrom, using compounds that inhibit the Transient Receptor Potential C6 ion channel (TRPC6).

BACKGROUND

A variety of ion channel proteins exist to mediate ion flux across cellular membranes. The proper expression and function of ion channel proteins is essential for the maintenance of cellular function, intracellular communication, and the like. An important aspect of achieving cellular homeostasis is the maintenance of appropriate ion concentrations in various cell types during development and in response to numerous stimuli. Large numbers of diverse types of ion channels act to maintain cellular homeostasis by moving ions into and out of cells across the plasma membrane, and within cells by moving ions across membranes of intracellular organelles including, for example, the endoplasmic reticulum, sarcoplasmic reticulum, mitochondria and endocytic organelles including endosomes and lysosomes. Numerous diseases are the result of dysregulation of membrane potential or aberrant calcium handling. Given the central importance of ion channels in modulating membrane potential and ion flux in cells, identification of agents that can promote or inhibit particular ion channels is of great interest as research tools and as possible therapeutic agents.

One such channel is the Transient Receptor Potential C6 (TRPC6) channel. TRPC6 belongs to the larger family of TRP ion channels (see, Desai et al., 2005 Eur J Physiol 451:11-18; Clapham et al., 2001 Nat Neurosci 2:387-396; Clapham, 2003 Nature 426: 517-524; Clapham et al., Pharmacol Rev 55:591-596, 2003). TRPC6 is a calcium permeable channel, specifically a non-selective calcium permeable cation channel. In addition to calcium ions, TRPC6 channels are permeable to other cations, for example sodium. Thus, TRPC6 channels modulate not only intracellular calcium concentration, but also membrane potential by modulating the flux of cations including calcium and sodium ions. Although non-selective cation channels such as TRPC6 modulate, among other things, calcium ion flux, they are mechanistically distinct from voltage-gated calcium channels. Generally, voltage-gated calcium channels respond to depolarization of the potential difference across the membrane and can open to permit an influx of calcium from the extracellular medium and a rapid increase in intracellular calcium levels or concentrations. In contrast, non-selective cation channels such as TRPC6 are generally signal transduction gated, long-lasting, and produce less rapid changes in ion concentration. They show increased activity in response to the production of the second messenger, diacylglycerol (Hofmann et al., 1999). In addition, TRPC6 can respond to changes in pressure. These mechanistic differences are accompanied by structural differences among voltage-gated and cation permeable channels. Thus, although many diverse channels act to regulate ion flux and membrane potential in various cell types and in response to numerous stimuli, it is important to recognize the significant structural, functional, and mechanistic differences among different classes of ion channels.

Based on its expression and work implicating it in Transforming Growth Factor-Beta TGF-ß signaling (involved in cell growth, differentiation and apoptosis), TRPC6 is also thought to be important in treating or preventing diseases or disorders of the respiratory system.

Yue et al. studied TRPC6 channels for a role in mediating the pulmonary artery smooth muscle cell proliferation that can lead to idiopathic pulmonary arterial hypertension (IPAH) and pulmonary hypertension (PH). Pulmonary vascular medial hypertrophy caused by excessive pulmonary artery smooth muscle cell (PASMC) proliferation is a major cause for the elevated pulmonary vascular resistance in patients with IPAH and PH. The authors found that TRPC6 was highly expressed and TRPC3 was minimally expressed in PASMC from healthy lung tissue. However, in lung tissue from IPAH patients, mRNA and protein expression of TRPC3 and TRPC6 were significantly elevated in comparison to that in normotensive patients. Furthermore, proliferation of PASMC cells derived from IPAH patients was markedly reduced following incubation with TRPC6 siRNA. Based on these results, the authors concluded that TRPC6 may be important in mediating proper PASMC proliferation, and that dysregulation of TRPC6 may lead to increased PASMC proliferation and pulmonary vascular medial hypertrophy observed in IPAH patients (Yu et al., 2004 Proc Natl Acad Sci 101(38):13861-6). Further support is provided by the observation that in IPAH patients the frequency of a single-nucleotide polymorphism in the promoter of TRPC6 which increases expression was significantly higher when compared to normal subjects (Yue, et al., 2009 Circulation 119: 2313-22).

Additional evidence implicating TRPC6 dysregulation in IPAH comes from studies of bosentan, a dual endothelin receptor blocker that has been used clinically to treat IPAH. This inhibitor decreases proliferation of PASMCs, but the mechanism by which this occurs is unclear. Interestingly, bosentan both decreases proliferation of PASMC and also decreases expression of TRPC6 in lung tissue of IPAH patients (Kunichika et al., 2004 Am J Respir Crit Care Med 170(10):1101-7).

Evidence supports a role of TRPC6 in additional pulmonary disorders. In alveolar macrophages from patients with chronic obstructive pulmonary disease (COPD), TRPC6 expression was found to be elevated when compared with controls (Finney-Hayward et al., 2010 Am J Respir Cell Mol Biol 43:296-304). In human cystic fibrosis epithelial cells, the TRPC6-mediated calcium influx is abnormally increased and may contribute to the hypersecretion of mucus. siRNA-TRPC6 was able to reduce this abnormal calcium influx (Antigny et al. 2011 Am J Resp Cell Mol Biol, 44:83-90). In mouse lung fibroblasts, the pro-fibrotic activity of PDGF is dependent on the activation of TRPC6, suggesting that TRPC6 inhibition would reduce lung fibrosis (Lei et al., 2014 Biomaterials 35:2868-77). A role of TRPC6 in pulmonary endothelial cell function was demonstrated in mouse lung models of ischemia-reperfusion induced-edema and lipopolysaccharide-induced inflammation in which TRPC6 deficiency was able to reduce acute lung injury by preserving endothelial barrier function (Weissmann et al., 2011 Nat Comm, 3:649-58 and Tauseef et al., 2012 J Exp Med 209:1953-68).

The inhibition of TRPC6 is an attractive means for preventing other respiratory disorders including lung vascular hyperpermeability, pulmonary (lung) edema, acute respiratory distress syndrome (ARDS), acute lung injury (ALI), lung ischemia reperfusion, idiopathic interstitial pneumonia, Idiopathic pulmonary fibrosis (IPF) and acute exacerbation IPF, severe acute respiratory syndrome (SARS), and Middle Eastern respiratory syndrome (MERS).

Increased vascular permeability (vascular hyperpermeability) contributes to many diseases, including acute respiratory distress syndrome, sepsis, severe sepsis, septic shock, cancer and inflammation. Reducing vascular hyperpermeability of the lung will reduce the accumulation of fluid in the alveolar space (lung edema) and therefore will improve the gas exchange between the lung and the vessels leading to a better oxygenation of the arterial blood. Improvement of the arterial blood oxygenation translates into a better oxygenation of all the organs (brain, heart, liver, kidney . . . etc.) and reduces the risk of multiple organ failure followed by death.

Increase in vascular permeability in sepsis, severe sepsis, septic shock or ischemia reperfusion is also reported in several organs including but not limited to the lung, kidney, liver and heart. The accumulation of fluid in these organs impairs their proper functioning (e.g. causing arrhythmia, glomerular filtration disruption, or impairment of the metabolism) and leads to organ failure followed by death.

Pulmonary (lung) edema is a condition in which the lungs fill with fluid. The most common cause of pulmonary edema is congestive heart failure. Other less common conditions that may cause pulmonary edema include sudden high blood pressure, pneumonia, kidney failure, lung damage caused by severe infection, severe sepsis of the blood, or blood poisoning caused by infection.

Acute lung injury (ALI) is a lung disorder often caused by smoke inhalation including, more recently, in the use of E-cigarette or vaping products. Chronic exposure of cigarette smoke (CS) to rats resulted in an increase in TRPC6 mRNA and protein expression in distal pulmonary arteries and similar effects were observed using PASMCs in vitro. Nicotine treatment of cultured rat PASMCs upregulated TRPC6 expression and increased intracellular calcium levels, both of which were reduced by TRPC6 siRNA silencing (Wang et al., 2014 Am J Physiol Cell Physiol 306:C364-73). These results suggest a role for TRPC6 in CS-induced lung injury. Regulation of the TRPC6 pathway may be useful in treating ALI. The separation of ALI from ARDS is of more historical interest, with ALI now considered as a milder or earlier form of ARDS (JAMA. 2012; 307(23):2526-2533).

Acute respiratory distress syndrome (ARDS) is a lung inflammation characterized by an increase in lung vascular permeability and/or lung edema. ARDS is often characterized as low, mild, or severe based on the degree of hypoxemia. ARDS can be triggered by several causes, e.g. can be induced by a bacterial or viral lung infection, by sepsis, inhalation of harmful substances, severe pneumonia, trauma, pancreatitis (inflammation of the pancreas), massive blood transfusions and burns. The most common cause of ARDS is sepsis.

Severe acute respiratory syndrome (SARS) is a viral respiratory illness caused by a coronavirus called SARS-associated coronavirus (SARS-CoV). SARS begins with a high fever (temperature greater than 100.4° F. [>38.0° C.]). Other symptoms may include sore throat, cough, headache, an overall feeling of discomfort, and body aches. Some people also have mild respiratory symptoms at the outset. Most patients develop pneumonia. Since 2004 until the outbrake of SARS-CoV-2 pandemic in December 2019, there have not been any known cases of SARS reported anywhere in the world.

Middle Eastern respiratory syndrome (MERS) is an illness caused by a virus (more specifically, a coronavirus) called Middle East Respiratory Syndrome Coronavirus (MERS-CoV). The disease is characterized by severe respiratory illness, including fever, cough, and shortness of breath. About 3 or 4 out of every 10 patients reported with MERS have died. ARDS can occur as a result of other respiratory viruses, not just coronaviruses, for example, but not limited to Herpes viruses, influenza viruses, respiratory syncytial virus, and parainfluenza viruses.

Calcium overload has been recognized as a critical cause of the injury tissues suffer after periods of ischemia. The ports that determine calcium entry into tissues subjected to transient hypoxia have not been identified. TRPC6 is one of the major factors causing calcium entry in the heart and in the lungs, which is responsible for ischemia/reperfusion (I/R) injury. Blocking TRPC6 activity or the genetic ablation of TRPCs markedly protected cardiac and lung tissue and cells from I/R injury (He et al., PNAS. 2017; 19: E4582-E4591, Weismann et al., Nature Communications. 2012; 3(649): DOI:10.1038)

Sepsis, severe sepsis, and septic shock are disorders arising from the systemic inflammatory response to an infection (see Mitchell M. Levy et al., Crit Care Med. 2003 April; 31(4):1250-6). Sepsis is a disorder having both an infection (e.g., viral, bacterial, abdominal trauma, gut perforation) and a systemic inflammatory response. This leads to increase in vascular permeability of several organs such as kidney liver, heart and lung. Severe sepsis (sepsis with organ dysfunction) refers to sepsis with acute organ dysfunction caused by sepsis. Septic shock refers to persistent hypotension unexplained by other causes.

TRPC6 inhibitors may be useful to reduce progression to, severity and/or the rate of mortality in SARS, MERS, and ARDS. TRPC6 inhibitors may be useful to reduce severity and/or the rate of mortality in sepsis, severe sepsis and septic shock since the survival rate in the mouse model of systemic sepsis (cecal ligation puncture, CLP) was significantly improved (80% vs 10% in the vehicle group) in TRPC6 deficient mice (Tauseef et al., 2012 J Exp Med 209: 1953-1968).

In patients hospitalized for Covid-19, there is an increase in reactive oxygen species (ROS) due to airway injury. ROS has been shown to activate TRPC6, causing a cascade of cellular damage resulting in disruption of cell barrier function, hyper-permeability, plasma leakage and eventually oedema and acute respiratory distress syndrome (ARDS). (See Z. S. Miripour et al., Biosensors and Bioelectronics 165 (2020) 112435.) TRPC6 inhibition has been shown to stabilize the pulmonary vasculature to ROS-induced hyper-permeability and may prevent lung oedema in patients with severe SARS-CoV2 infection.

There is a need for highly selective TRPC6 antagonists for treating respiratory diseases or disorders that can be alleviated by modulating TRPC6.

BRIEF SUMMARY OF THE INVENTION

The present invention provides methods for treating disorders associated with vascular hyperpermeability and/or conditions arising therefrom by inhibiting the Transient Receptor Potential C6 ion channel (TRPC6).

Disorders associated with vascular hyperpermeability encompass (group 1): respiratory disorders associated with vascular hyperpermeability that are not primarily caused by an infection, and (group 2): disorders associated with vascular hyperpermeability caused by certain bacterial, viral, or fungal parasites infections.

Disorders of group 1 are selected from the group consisting of pulmonary (lung) edema),
idiopathic interstitial pneumonia,
idiopathic pulmonary fibrosis (IPF) and acute exacerbation IPF,
ARDS, not infection-related,
acute lung injury (ALI), and
lung ischemia reperfusion.

Disorders of group 2 are selected from the group consisting of

ARDS, related to infection,
severe acute respiratory syndrome (SARS),
middle eastern respiratory syndrome (MERS),
sepsis,
severe sepsis, and
septic shock.

ARDS, not infection-related, is understood as ARDS which is not triggered or caused by an infection, such as ARDS caused by inhalation of harmful substances (e.g. toxic smoke), trauma, pancreatitis, gastric juice reflux, massive blood transfusions or burns.

ARDS, infection-related, is understood as ARDS which is triggered or caused by an infection, such as ARDS caused by sepsis or severe pneumonia.

In one embodiment, the invention relates to a method for treating a disorder associated with vascular hyperpermeability and/or conditions arising therefrom, comprising administering to a patient in need thereof a pharmaceutically effective amount of a TRPC6 inhibitor of formula (I), (I)

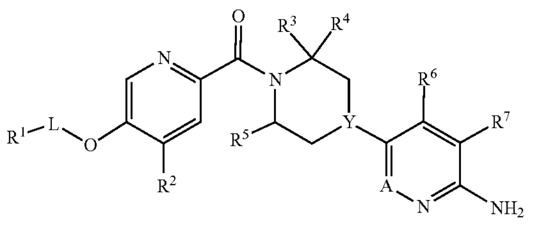

wherein

L is absent or is methylene or ethylene;
Y is CH or N;
A is CH or N;
$R^1$ is selected from the group consisting of:
$C_{1-6}$alkyl optionally substituted with 1 to 3 groups independently selected from the group consisting of halo, $C_{3-6}$cycloalkyl and $OC_{3-6}$cycloalkyl;
phenyl optionally substituted with 1 to 3 groups independently selected from the group consisting of $CF_3$, halo, $C_{3-6}$cycloalkyl, $OC_{3-6}$cycloalkyl, and $OC_{1-6}$alkyl optionally substituted with one to three halo; and
$C_{3-6}$cycloalkyl optionally substituted with 1 to 3 groups independently selected from the group consisting of halo and $C_{1-6}$alkyl optionally substituted with 1 to 3 halo;
$R^2$ is selected from the group consisting of H, $C_{1-6}$alkyl, $OCF_3$, $C_{3-6}$cycloalkyl, $OC_{1-6}$alkyl, and $OC_{3-6}$cycloalkyl;
$R^3$ is selected from the group consisting of H, $C_{1-6}$alkyl, $C_{3-6}$cycloalkyl, and $OC_{3-6}$cycloalkyl; wherein each of the $C_{1-6}$alkyl, $C_{3-6}$cycloalkyl, $OC_{3-6}$cycloalkyl of the $R^3$ group may be optionally substituted with one to three groups each independently selected from the group consisting of halo, OH, $OC_{1-6}$alkyl, and $SC_{1-6}$alkyl, $N(C_{1-6}alky)_2$; and wherein one to three carbon atoms of the $C_{1-6}$alkyl of the $R^3$ group may optionally be replaced one or two moieties selected from the group consisting of NH, $N(C_{1-6}alkyl)$, O, and S;
$R^4$ and $R^5$ are each independently selected from the group consisting of H and $C_{1-6}$alkyl;
$R^3$ and $R^4$ can together with the atom to which they are attached join to form a 3 to 9-membered carbocyclyl ring which optionally may contain one to three heteroatoms selected from the group consisting of N, O, and S; or
$R^3$ and $R^5$ can together form a 3 to 9-membered bicyclic ring which optionally may contain one to three heteroatoms selected from the group consisting of N, O, and S;
$R^6$ is selected from the group consisting of H, $C_{1-6}$alkyl, CN, $CF_3$, $OCF_3$, $C_{3-6}$cycloalkyl, $OC_{1-6}$alkyl, and $OC_{3-6}$cycloalkyl;
$R^7$ is selected from the group consisting of H and $OC_{1-6}$alkyl;
or a pharmaceutically acceptable salt thereof.

In a second embodiment, the invention relates to the method of the first embodiment, wherein the disorder associated with vascular hyperpermeability and/or conditions arising therefrom is selected from the group 1 consisting of:

pulmonary (lung) edema,
idiopathic interstitial pneumonia,
idiopathic pulmonary fibrosis (IPF) and acute exacerbation IPF,
(ARDS), not infection-related,
acute lung injury (ALI), and
lung ischemia reperfusion.

In a third embodiment, the invention relates to the method of the first embodiment, wherein the disorder associated with vascular hyperpermeability and/or conditions arising therefrom is selected from the group 2 consisting of:

ARDS, related to infection,
severe acute respiratory syndrome (SARS),
middle eastern respiratory syndrome (MERS),
sepsis,
severe sepsis, and
septic shock.

In another embodiment (embodiment four), the invention relates to a method of using the compound of formula (I) according to any one of embodiments one, two or three, wherein $R^1$ is selected from the group consisting of:
$C_{1-6}$alkyl optionally substituted with 1 to 3 groups independently selected from the group consisting of halo, and $C_{3-6}$cycloalkyl;
phenyl optionally substituted with 1 to 3 groups independently selected from the group consisting of $CF_3$, halo, $OC_{3-6}$cycloalkyl, and $OC_{1-6}$alkyl optionally substituted with one to three halo; and
$C_{3-6}$cycloalkyl optionally substituted with 1 to 3 halo groups;
$R^2$ is $OC_{1-6}$alkyl;
$R^3$ is selected from the group consisting of H and $C_{1-6}$alkyl optionally substituted with OH or $OC_{1-6}$alkyl,
$R^4$ is H;
$R^5$ is H;
$R^3$ and $R^4$ can together with the atom to which they are attached join to form a 3 to 9-membered carbocyclyl ring which optionally may contain one to three heteroatoms selected from the group consisting of N and O; or $R^3$ and $R^5$ can together form a 3 to 9-membered bicyclic which optionally may contain one to three heteroatoms selected from the group consisting of N and O;

$R^6$ is selected from the group consisting of H, $C_{1-6}$alkyl, $OC_{1-6}$alkyl, and $OC_{3-6}$cycloalkyl, $R^7$ is selected from the group consisting of H and $OC_{1-6}$alkyl;

or a pharmaceutically acceptable salt thereof.

In another embodiment (embodiment five), the invention relates to a method of using the compound of formula (I) according to any one of embodiments one, two or three, wherein A is CH and Y is N; or A is CH and Y is CH; or A is N and Y is CH;

or a pharmaceutically acceptable salt thereof.

In another embodiment (embodiment six), the invention relates to a method of using the compound of formula (I) according to any one of embodiments one, two or three, wherein $R^1$ is selected from the group consisting phenyl optionally substituted with a group selected from the group consisting of $CF_3$, $OCF_3$, halo, $OC_{3-6}$cycloalkyl, and $OC_{1-6}$alkyl optionally substituted with one to three halo; and, $R^2$ is $OC_{1-6}$alkyl;

$R^3$ is selected from the group consisting of H and $C_{1-6}$alkyl optionally substituted with OH or $OC_{1-6}$alkyl;

$R^4$ is H;

$R^5$ is H;

$R^3$ and $R^4$ can together with the atom to which they are attached join to form a 3 to 9-membered carbocyclyl ring which optionally may contain one to three heteroatoms selected from the group consisting of N and O; or $R^3$ and $R^5$ can together form a 3 to 9-membered bicyclic which optionally may contain one to three heteroatoms selected from the group consisting of N and O;

$R^6$ is selected from the group consisting of H, $C_{1-6}$alkyl, $OC_{1-6}$alkyl, and $OC_{3-6}$cycloalkyl;

$R^7$ is selected from the group consisting of H and $OC_{1-6}$alkyl;

or a pharmaceutically acceptable salt thereof.

In another embodiment (embodiment seven), the invention relates to a method of using the compound of formula (I) according to any one of embodiments one, two or three, wherein $R^1$ is selected from the group consisting phenyl optionally substituted with a group selected from the group consisting of $CF_3$, $OCF_3$, F, and methoxy;

$R^2$ is selected from the group consisting of methoxy and ethoxy;

$R^3$ is selected from the group consisting of H, 2-hydroxymethyl, methoxymethyl, and 1-hydroxyethyl;

$R^4$ is H;

$R^5$ is H;

or $R^3$ is ethyl, and $R^3$ and $R^4$ join to form a spirocyclic ring;

or $R^3$ is ethyl or methoxymethyl, and $R^3$ and $R^5$ join to form a bicyclic ring;

$R^6$ is selected from the group consisting of H, methyl, methoxy, ethoxy, propoxy, and cyclylpropyloxy;

$R^7$ is selected from the group consisting of H and methoxy;

or a pharmaceutically acceptable salt thereof.

In another embodiment (embodiment eight), the invention relates to a method of using the compound of formula (I) according to any one of embodiments one, two or three, wherein $R^1$ together with L represent a group selected from the group consisting of phenyl, 4-chlorophenyl, 4-fluorophenyl, 4-methoxyphenyl, 4-isopropoxyphenyl, 4-trifluoromethylphenyl, 4-difluoromethoxyphenyl 4-cyclopropyloxyphenyl, cyclopropyl, cyclopentyl, cyclohexyl, benzyl, 2-fluorobenzyl, and phenylethyl;

$R^2$ is methoxy or ethoxy;

or a pharmaceutically acceptable salt thereof.

In another embodiment (embodiment nine), the invention relates to a method of using the compound of formula (I) according to any one of embodiments one, two or three, wherein Y is CH and A is N;

$R^1$ together with L represent a group selected from the group consisting of phenyl, 4-chlorophenyl, 4-fluorophenyl, 4-methoxyphenyl, 4-isopropoxyphenyl, 4-trifluoromethylphenyl, 4-difluoromethoxyphenyl 4-cyclopropyloxyphenyl, benzyl, 2-fluorobenzyl, and phenylethyl;

$R^2$ is methoxy or ethoxy;

$R^3$, $R^4$ and $R^5$ are each H;

$R^6$ is H, methyl, methoxy or ethoxy;

$R^7$ is H;

or a pharmaceutically acceptable salt thereof.

In another embodiment (embodiment ten), the invention relates to a method of using the compound of formula (I) according to any one of embodiments one, two or three, wherein Y is CH and A is CH;

$R^1$ together with L represent a group selected from the group consisting of phenyl, 4-chlorophenyl, 4-fluorophenyl, 4-methoxyphenyl, 4-trifluoromethylphenyl, cyclopentyl, cyclohexyl, benzyl, 2-fluorobenzyl, and phenylethyl;

$R^2$ is methoxy or ethoxy;

$R^3$, $R^4$ and $R^5$ are each H;

$R^6$ is H, methyl, methoxy, or ethoxy;

$R^7$ is H;

or a pharmaceutically acceptable salt thereof.

In another embodiment (embodiment eleven), the invention relates to a method of using the compound of formula (I) according to any one of embodiments one, two or three, wherein Y is N and A is CH;

$R^1$ together with L represent a group selected from the group consisting of phenyl, and 4-fluorophenyl;

$R^2$ is methoxy;

$R^3$ is selected from the group consisting of H, 2-hydroxymethyl, and hydroxyethyl, $R^4$ is H;

$R^5$ is H;

$R^3$ and $R^4$ may join to form a spirocyclic ring;

or $R^3$ and $R^5$ may join to form a bicyclic ring;

$R^6$ is selected from the group consisting of H and methoxy;

$R^7$ is H;

or a pharmaceutically acceptable salt thereof.

In another embodiment (embodiment twelve), the invention relates to a method of using the compound of formula (I) according to any one of embodiments one, two or three, wherein $R^1$ is $C_{1-6}$alkyl optionally substituted with 1 to 3 groups independently selected from the group consisting of halo and $C_{3-6}$cycloalkyl;

$R^2$ is $OC_{1-6}$alkyl;

$R^3$, $R^4$ and $R^5$ are each H;

$R^6$ is selected from the group consisting of H, $C_{1-6}$alkyl, and $OC_{1-6}$alkyl;

$R^7$ is H;

or a pharmaceutically acceptable salt thereof.

In another embodiment (embodiment thirteen), the invention relates to a method of using the compound of formula (I) according to any one of embodiments one, two or three, wherein $R^1$ together with L represent a group selected from the group consisting ethyl, propyl, isopropyl, isobutyl, cyclopropylmethyl, cyclobutylmethyl, 2,2-dimethylpropyl, 1-methylcyclopropylmethyl, 1-fluoromethylcyclopropylmethyl, 1-cyclopropylethyl, 2-cyclopropylethyl, cyclopentyl, cyclohexyl, 2,2-difluorocyclobutylmethyl, 3,3-difluorocyclobutylmethyl, 3-(trifluoromethyl)cyclobutylmethyl, and 3,3,3-trifluoro-2-methyl-propyl;

$R^2$ is methoxy;

$R^3$, $R^4$ and $R^5$ are each H;

$R^6$ is selected from the group consisting of H, methyl, and methoxy;

$R^7$ is H;

or a pharmaceutically acceptable salt thereof.

In another embodiment (embodiment fourteen), the invention relates to a method of using the compound of formula (I) according to any one of embodiments one, two or three, wherein Y is CH and A is N;

$R^1$ together with L represent a group selected from the group consisting propyl, isopropyl, isobutyl, cyclopropylmethyl, cyclobutylmethyl, 2,2-dimethylpropyl, 1-cyclopropylethyl, 2-cyclopropylethyl, and cyclohexyl;

$R^2$ is methoxy;

$R^3$, $R^4$ and $R^5$ are each H;

$R^6$ is selected from the group consisting of H, methyl, and methoxy;

$R^7$ is H;

or a pharmaceutically acceptable salt thereof.

In another embodiment (embodiment fifteen), the invention relates to a method of using the compound of formula (I) according to any one of embodiments one, two or three, wherein Y is CH and A is CH;

$R^1$ together with L represent a group selected from the group consisting ethyl, propyl, isopropyl, isobutyl, cyclopropylmethyl, cyclobutylmethyl, 2,2-dimethylpropyl, 1-methylcyclopropylmethyl, 1-fluoromethylcyclopropylmethyl, 1-cyclopropylethyl, 2-cyclopropylethyl, cyclopentyl, cyclohexyl, 2,2-difluorocyclobutylmethyl, 3,3-difluorocyclobutylmethyl, 3-(trifluoromethyl)cyclobutylmethyl, and 3,3,3-trifluoro-2-methyl-propyl;

$R^2$ is methoxy;

$R^3$, $R^4$ and $R^5$ are each H;

$R^6$ is selected from the group consisting of H, methyl, and methoxy;

$R^7$ is H;

or a pharmaceutically acceptable salt thereof.

In another embodiment (embodiment sixteen), the invention relates to a method of using the compound of formula (I) according to any one of embodiments one, two or three, wherein $R^3$ and $R^4$ together with the atom to which they are attached join to form a 3-membered carbocyclyl ring;

or a pharmaceutically acceptable salt thereof.

In another embodiment (embodiment seventeen), the invention relates to a method of using the compound of formula (I) according to any one of embodiments one, two or three, wherein $R^3$ and $R^5$ together form a 3 to 9-membered bicyclic ring which optionally may contain one to two heteroatoms independently selected from the group consisting of N and O, and or a pharmaceutically acceptable salt thereof.

In another embodiment (embodiment eighteen), the invention relates to a method of using the compound of formula (I) according to any one of embodiments one, two or three, wherein Y is C;

A is N;

$R^2$ is $OCH_3$; and $R^3$, $R^4$, $R^5$ and $R^7$ are each H;

or a pharmaceutically acceptable salt thereof.

In another embodiment (embodiment nineteen), the invention relates to a method of using the compound of formula (I) according to any one of embodiments one, two or three, wherein L is absent;

$R^1$ is phenyl optionally substituted with 1 to 3 groups independently selected from the group consisting of $CF_3$, halo, $C_{3-6}$cycloalkyl, $OC_{3-6}$cycloalkyl, and $OC_{1-6}$alkyl optionally substituted with one to three halo; and $R^6$ is H; or $OCH_3$;

or a pharmaceutically acceptable salt thereof.

In another embodiment (embodiment twenty), the invention relates to a method of using the compound of formula (I) according to any one of embodiments one, two or three, wherein $R^1$ is selected from the group consisting of phenyl optionally substituted with 1 to 3 groups independently selected from the group consisting of $CF_3$, halo, $OC_{3-6}$cycloalkyl, and $OC_{1-6}$alkyl optionally substituted with one to three halo;

$R^2$ is $OCH_3$ or $OCH_2CH_3$;

$R^3$, $R^4$, $R^5$, $R^6$, and $R^7$ are each H; and or a pharmaceutically acceptable salt thereof.

In another embodiment (embodiment twenty-one), the invention relates to a method of using the compound of formula (I) according to any one of embodiments one, two or three, wherein $R^1$ is selected from the group consisting of phenyl optionally substituted with 1 to 3 groups independently selected from the group consisting of $CF_3$, halo, $OC_{3-6}$cycloalkyl, and $OC_{1-6}$alkyl optionally substituted with one to three halo;

$R^2$ is $OCH_3$ of $OCH_2CH_3$;

$R^3$, $R^4$, $R^5$ and $R^7$ are each H;

$R^6$ is $CH_3$ or $OCH_3$;

Y is CH; and

A is N;

or a pharmaceutically acceptable salt thereof.

In another embodiment (embodiment twenty-two), the invention relates to a method of using the compound of formula (I) according to any one of embodiments one, two or three, wherein L is absent;

or a pharmaceutically acceptable salt thereof.

In another embodiment (embodiment twenty-three), the invention relates to a method of using the compound of formula (I) according to any one of embodiments one, two or three, wherein the compound is selected from the group consisting of any one of compounds 1-95 in Table 1, or a pharmaceutically acceptable salt thereof.

In another embodiment (embodiment twenty-four), the invention relates to a method for treating a disorder associated with vascular hyperpermeability and/or conditions arising therefrom comprising administering to a patient in need thereof a pharmaceutical composition comprising a compound of formula (I) or any compound of the invention as defined herein, or a pharmaceutically acceptable salt thereof, and optionally a pharmaceutically acceptable excipient.

DETAILED DESCRIPTION OF THE INVENTION

Figures 1A, 1B, 1C:
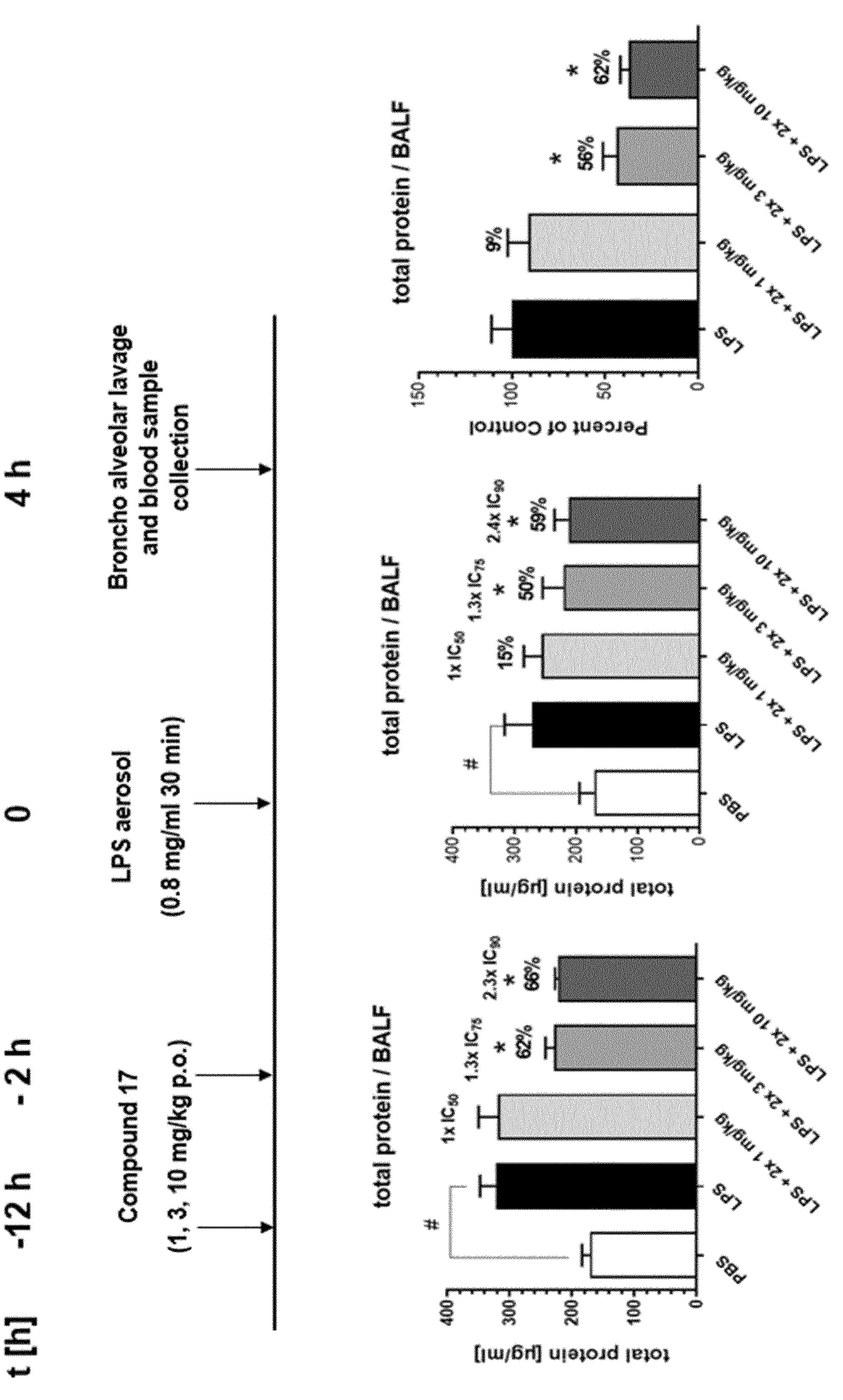
FIGS. 1A, 1B and 1C show that compound 17 significantly reduces pulmonary vascular leakage.

Table 1 shows specific compounds that can be used according to the methods described herein. The compounds shown in Table 1 may be prepared according to procedures described in WO2019081637.

TABLE 1

| Cpd No. | Structure | Compound Name |
|---|---|---|
| 1 | 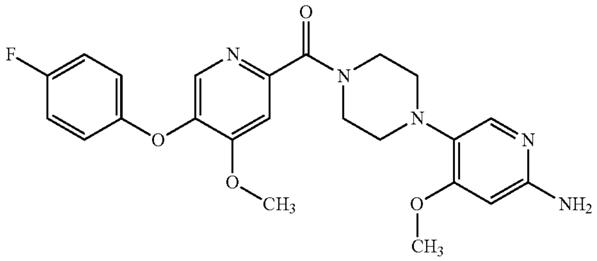 [SMILES: COc1cc(C(=O)N2CCN(c3cnc(N)cc3OC)CC2)ncc1Oc1ccc(F)cc1] | [4-(6-Amino-4-methoxy-pyridin-3-yl)-piperazin-1-yl]-[5-(4-fluoro-phenoxy)-4-methoxy-pyridin-2-yl]-methanone |
| 2 | 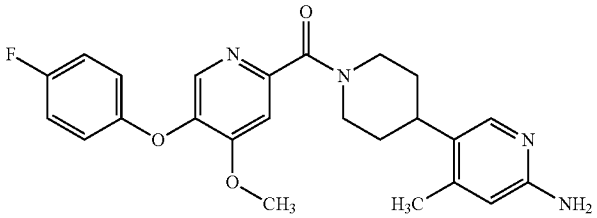 [SMILES: COc1cc(C(=O)N2CCC(c3cnc(N)cc3C)CC2)ncc1Oc1ccc(F)cc1] | (6-Amino-4-methyl-3',4',5',6'-tetrahydro-2'H-[3,4']bipyridinyl-1'-yl)-[5-(4-fluoro-phenoxy)-4-methoxy-pyridin-2-yl]-methanone |
| 3 | 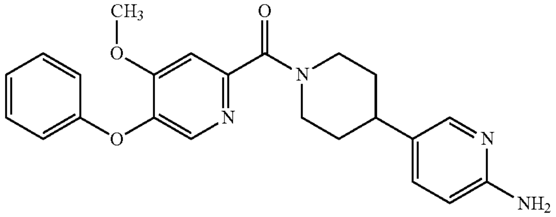 | (6-Amino-3',4',5',6'-tetrahydro-2'H-[3,4']bipyridinyl-1'-yl)-(4-methoxy-5-phenoxy-pyridin-2-yl)-methanone |
| 4 | 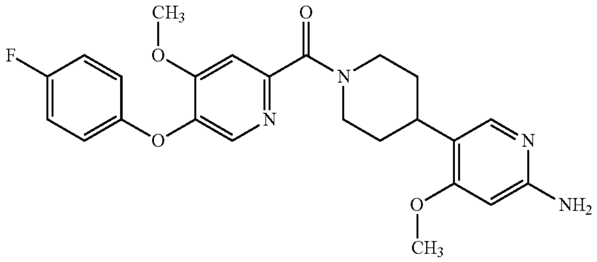 [SMILES: COc1cc(C(=O)N2CCC(c3cnc(N)cc3OC)CC2)ncc1Oc1ccc(F)cc1] | (6-Amino-4-methoxy-3',4',5',6'-tetrahydro-2'H-[3,4']bipyridinyl-1'-yl)-[5-(4-fluoro-phenoxy)-4-methoxy-pyridin-2-yl]-methanone |

TABLE 1-continued

| Cpd No. | Structure | Compound Name |
|---|---|---|
| 5 | 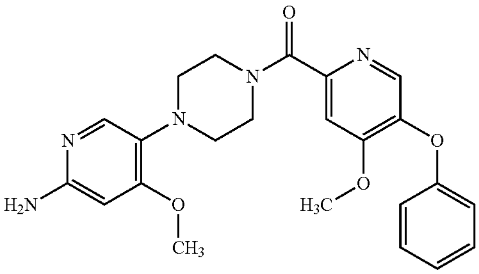 [SMILES: COc1cc(C(=O)N2CCN(c3cnc(N)cc3OC)CC2)ncc1Oc1ccccc1] | [4-(6-Amino-4-methoxy-pyridin-3-yl)-piperazin-1-yl]-(4-methoxy-5-phenoxy-pyridin-2-yl)-methanone |
| 6 | 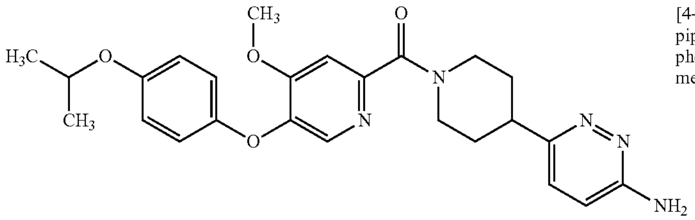 | [4-(6-Amino-pyridazin-3-yl)-piperidin-1-yl]-[5-(4-isopropoxy-phenoxy)-4-methoxy-pyridin-2-yl]-methanone |
| 7 | 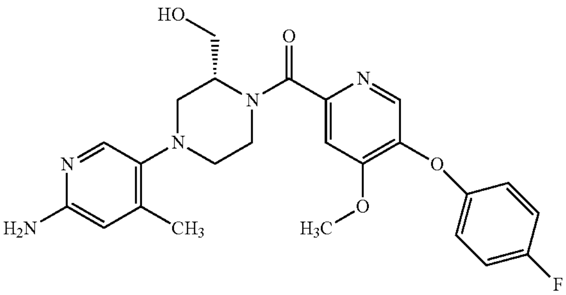 [SMILES: COc1cc(C(=O)N2CCN(c3cnc(N)cc3C)C[C@@H]2CO)ncc1Oc1ccc(F)cc1] | [(R)-4-(6-Amino-4-methyl-pyridin-3-yl)-2-hydroxymethyl-piperazin-1-yl]-[5-(4-fluoro-phenoxy)-4-methoxy-pyridin-2-yl]-methanone |
| 8 | 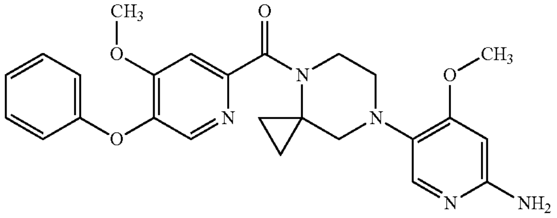 [SMILES: COc1cc(C(=O)N2CCN(c3cnc(N)cc3OC)CC23CC3)ncc1Oc1ccccc1] | [7-(6-Amino-4-methoxy-pyridin-3-yl)-4,7-diaza-spiro[2.5]oct-4-yl]-(4-methoxy-5-phenoxy-pyridin-2-yl)-methanone |
| 9 | 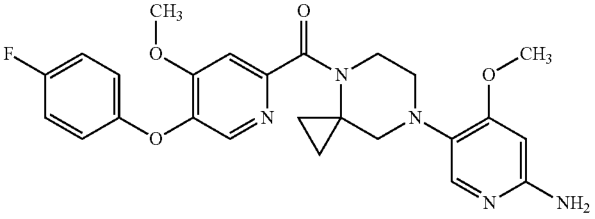 [SMILES: COc1cc(C(=O)N2CCN(c3cnc(N)cc3OC)CC23CC3)ncc1Oc1ccc(F)cc1] | [7-(6-Amino-4-methoxy-pyridin-3-yl)-4,7-diaza-spiro[2.5]oct-4-yl]-[5-(4-fluoro-phenoxy)-4-methoxy-pyridin-2-yl]-methanone |
| 10 | 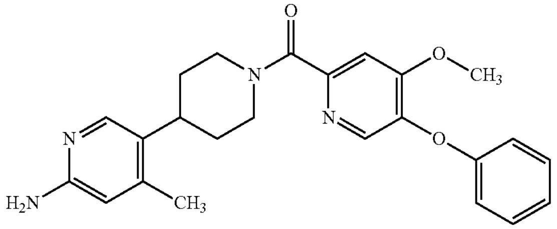 [SMILES: COc1cc(C(=O)N2CCC(c3cnc(N)cc3C)CC2)ncc1Oc1ccccc1] | (6-Amino-4-methyl-3',4',5',6'-tetrahydro-2'H-[3,4']bipyridinyl-1'-yl)-(4-methoxy-5-phenoxy-pyridin-2-yl)-methanone |

TABLE 1-continued

| Cpd No. | Structure | Compound Name |
| --- | --- | --- |
| 11 | 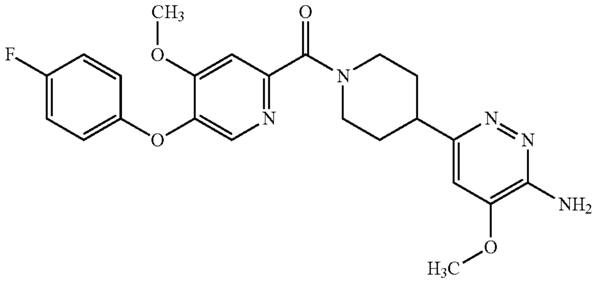 [SMILES: COc1cc(C(=O)N2CCC(c3cc(OC)c(N)nn3)CC2)ncc1Oc1ccc(F)cc1] | [4-(6-Amino-5-methoxy-pyridazin-3-yl)-piperidin-1-yl]-[5-(4-fluoro-phenoxy)-4-methoxy-pyridin-2-yl]-methanone |
| 12 | 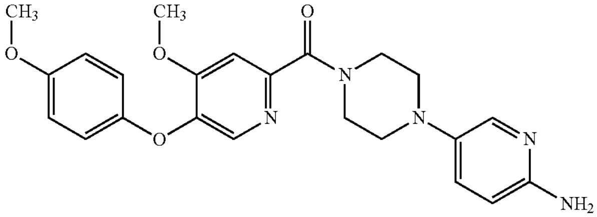 | [4-(6-Amino-pyridin-3-yl)-piperazin-1-yl]-[4-methoxy-5-(4-methoxy-phenoxy)-pyridin-2-yl]-methanone |
| 13 | 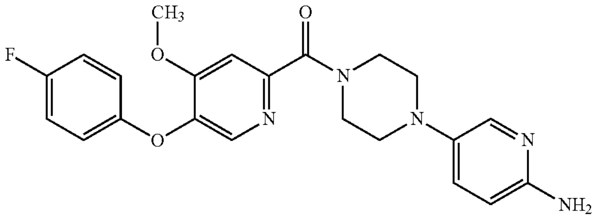 [SMILES: COc1cc(C(=O)N2CCN(c3ccc(N)nc3)CC2)ncc1Oc1ccc(F)cc1] | [4-(6-Amino-pyridin-3-yl)-piperazin-1-yl]-[5-(4-fluoro-phenoxy)-4-methoxy-pyridin-2-yl]-methanone |
| 14 | 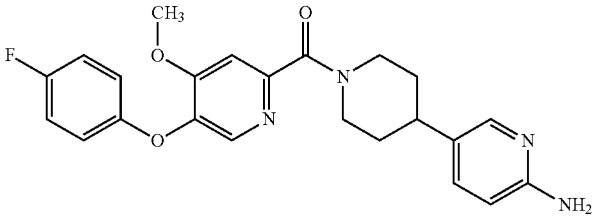 [SMILES: COc1cc(C(=O)N2CCC(c3ccc(N)nc3)CC2)ncc1Oc1ccc(F)cc1] | (6-Amino-3',4',5',6'-tetrahydro-2'H-[3,4']bipyridinyl-1'-yl)-[5-(4-fluoro-phenoxy)-4-methoxy-pyridin-2-yl]-methanone |
| 15 | 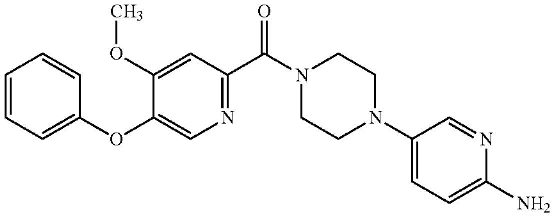 [SMILES: COc1cc(C(=O)N2CCN(c3ccc(N)nc3)CC2)ncc1Oc1ccccc1] | [4-(6-Amino-pyridin-3-yl)-piperazin-1-yl]-(4-methoxy-5-phenoxy-pyridin-2-yl)-methanone |
| 16 | 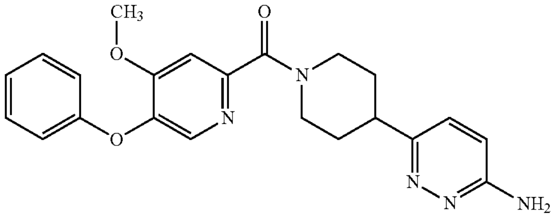 [SMILES: COc1cc(C(=O)N2CCC(c3ccc(N)nn3)CC2)ncc1Oc1ccccc1] | [4-(6-Amino-pyridazin-3-yl)-piperidin-1-yl]-(4-methoxy-5-phenoxy-pyridin-2-yl)-methanone |

TABLE 1-continued

| Cpd No. | Structure | Compound Name |
|---|---|---|
| 17 | 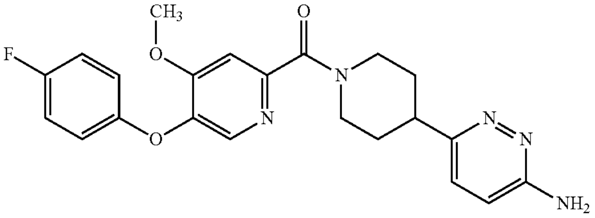 [SMILES: COc1cc(C(=O)N2CCC(c3ccc(N)nn3)CC2)ncc1Oc1ccc(F)cc1] | [4-(6-Amino-pyridazin-3-yl)-piperidin-1-yl]-[5-(4-fluoro-phenoxy)-4-methoxy-pyridin-2-yl]-methanone |
| 18 | 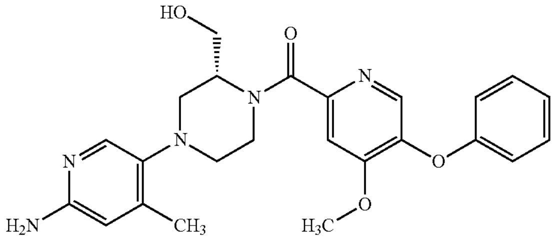 [SMILES: COc1cc(C(=O)N2CCN(c3cnc(N)cc3C)C[C@@H]2CO)ncc1Oc1ccccc1] | [(R)-4-(6-Amino-4-methyl-pyridin-3-yl)-2-hydroxymethyl-piperazin-1-yl]-(4-methoxy-5-phenoxy-pyridin-2-yl)-methanone |
| 19 | 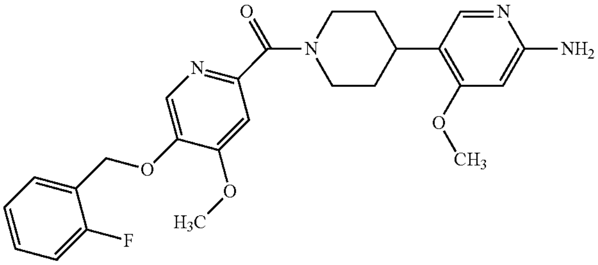 [SMILES: COc1cc(C(=O)N2CCC(c3cnc(N)cc3OC)CC2)ncc1OCc1ccccc1F] | (6-Amino-4-methoxy-3',4',5',6'-tetrahydro-2'H-[3,4']bipyridinyl-1'-yl)-[5-(2-fluoro-benzyloxy)-4-methoxy-pyridin-2-yl]-methanone |
| 20 | 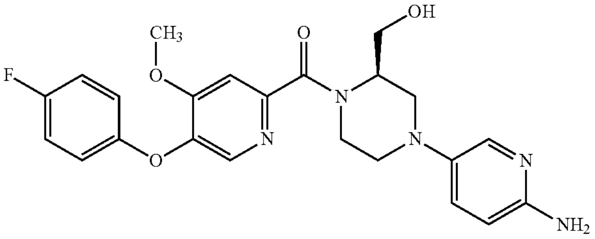 [SMILES: COc1cc(C(=O)N2CCN(c3ccc(N)nc3)C[C@@H]2CO)ncc1Oc1ccc(F)cc1] | [(R)-4-(6-Amino-pyridin-3-yl)-2-hydroxymethyl-piperazin-1-yl]-[5-(4-fluoro-phenoxy)-4-methoxy-pyridin-2-yl]-methanone |
| 21 | 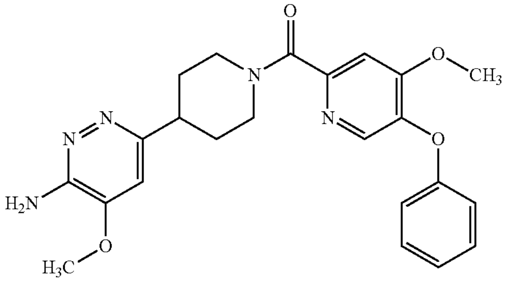 [SMILES: COc1cc(C(=O)N2CCC(c3cc(OC)c(N)nn3)CC2)ncc1Oc1ccccc1] | [4-(6-Amino-5-methoxy-pyridazin-3-yl)-piperidin-1-yl]-(4-methoxy-5-phenoxy-pyridin-2-yl)-methanone |
| 22 | 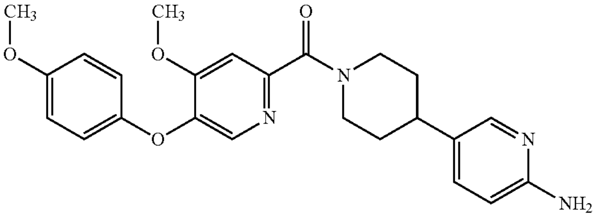 [SMILES: COc1ccc(Oc2cnc(C(=O)N3CCC(c4ccc(N)nc4)CC3)cc2OC)cc1] | (6-Amino-3',4',5',6'-tetrahydro-2'H-[3,4']bipyridinyl-1'-yl)-[4-methoxy-5-(4-methoxy-phenoxy)-pyridin-2-yl]-methanone |

TABLE 1-continued

| Cpd No. | Structure | Compound Name |
|---|---|---|
| 23 | 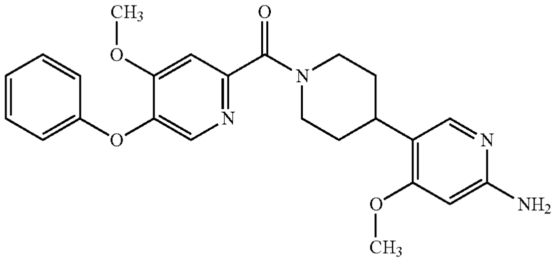 [SMILES: COc1cc(C(=O)N2CCC(c3cnc(N)cc3OC)CC2)ncc1Oc1ccccc1] | (6-Amino-4-methoxy-3',4',5',6'-tetrahydro-2'H-[3,4']bipyridinyl-1'-yl)-(4-methoxy-5-phenoxy-pyridin-2-yl)-methanone |
| 24 | 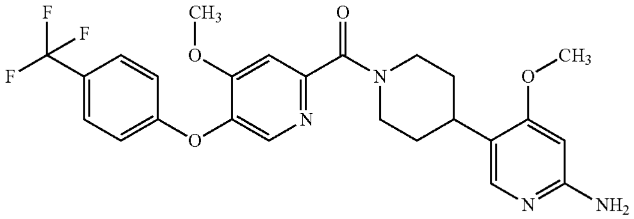 | (6-Amino-4-methoxy-3',4',5',6'-tetrahydro-2'H-[3,4']bipyridinyl-1'-yl)-[4-methoxy-5-(4-trifluoromethyl-phenoxy)-pyridin-2-yl]-methanone |
| 25 | 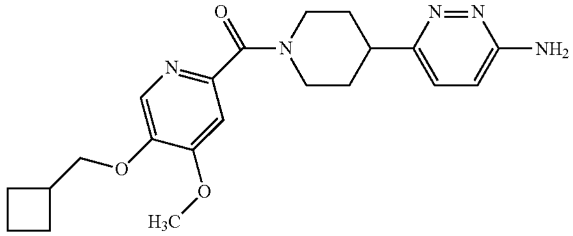 [SMILES: COc1cc(C(=O)N2CCC(c3ccc(N)nn3)CC2)ncc1OCC1CCC1] | [4-(6-Amino-pyridazin-3-yl)-piperidin-1-yl]-(5-cyclobutylmethoxy-4-methoxy-pyridin-2-yl)-methanone |
| 26 | 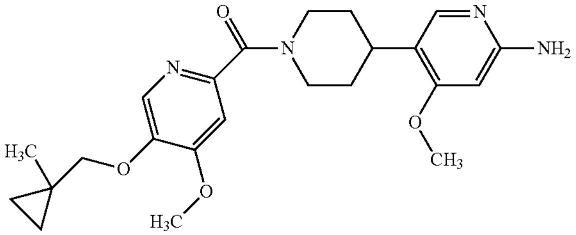 [SMILES: COc1cc(C(=O)N2CCC(c3cnc(N)cc3OC)CC2)ncc1OCC1(C)CC1] | (6-Amino-4-methoxy-3',4',5',6'-tetrahydro-2'H-[3,4']bipyridinyl-1'-yl)-[4-methoxy-5-(1-methyl-cyclopropylmethoxy)-pyridin-2-yl]-methanone |
| 27 | 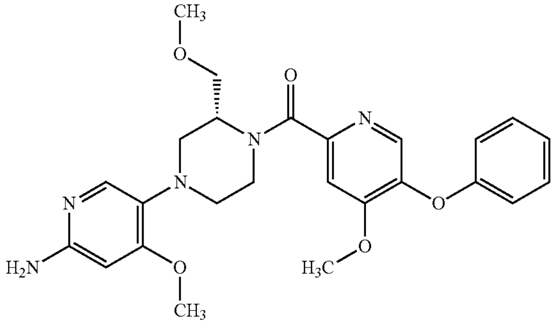 [SMILES: COC[C@H]1CN(c2cnc(N)cc2OC)CCN1C(=O)c1cc(OC)c(Oc2ccccc2)cn1] | [(R)-4-(6-Amino-4-methoxy-pyridin-3-yl)-2-methoxymethyl-piperazin-1-yl]-(4-methoxy-5-phenoxy-pyridin-2-yl)-methanone |
| 28 | 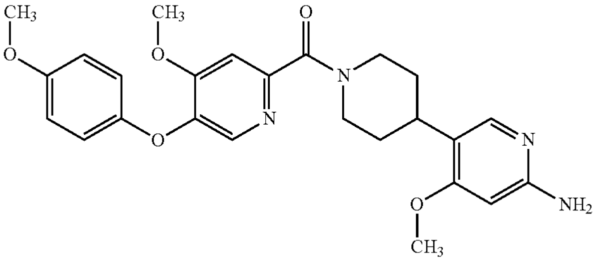 | (6-Amino-4-methoxy-3',4',5',6'-tetrahydro-2'H-[3,4']bipyridinyl-1'-yl)-[4-methoxy-5-(4-methoxy-phenoxy)-pyridin-2-yl]-methanone |

TABLE 1-continued

| Cpd No. | Structure | Compound Name |
| --- | --- | --- |
| 29 | 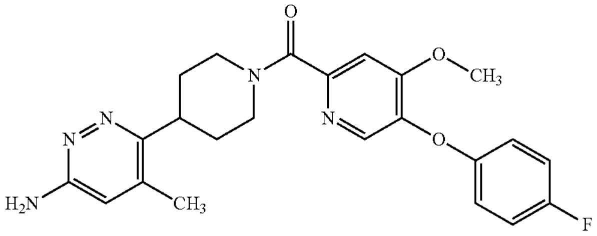 [SMILES: COc1cc(C(=O)N2CCC(c3nnc(N)cc3C)CC2)ncc1Oc1ccc(F)cc1] | [4-(6-Amino-4-methyl-pyridazin-3-yl)-piperidin-1-yl]-[5-(4-fluoro-phenoxy)-4-methoxy-pyridin-2-yl]-methanone |
| 30 | 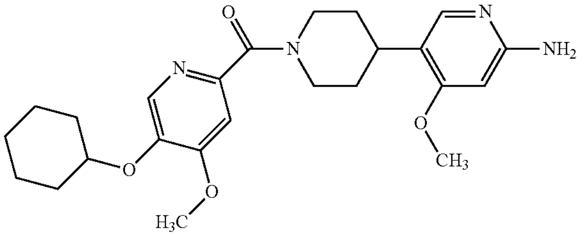 [SMILES: COc1cc(C(=O)N2CCC(c3cnc(N)cc3OC)CC2)ncc1OC1CCCCC1] | (6-Amino-4-methoxy-3',4',5',6'-tetrahydro-2'H-[3,4']bipyridinyl-1'-yl)-(5-cyclohexyloxy-4-methoxy-pyridin-2-yl)-methanone |
| 31 | 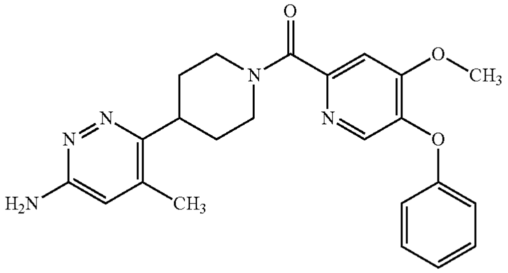 [SMILES: COc1cc(C(=O)N2CCC(c3nnc(N)cc3C)CC2)ncc1Oc1ccccc1] | [4-(6-Amino-4-methyl-pyridazin-3-yl)-piperidin-1-yl]-(4-methoxy-5-phenoxy-pyridin-2-yl)-methanone |
| 32 | 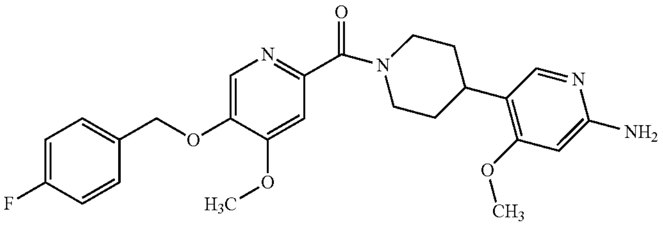 [SMILES: COc1cc(C(=O)N2CCC(c3cnc(N)cc3OC)CC2)ncc1OCc1ccc(F)cc1] | (6-Amino-4-methoxy-3',4',5',6'-tetrahydro-2'H-[3,4']bipyridinyl-1'-yl)-[5-(4-fluoro-benzyloxy)-4-methoxy-pyridin-2-yl]-methanone |
| 33 | 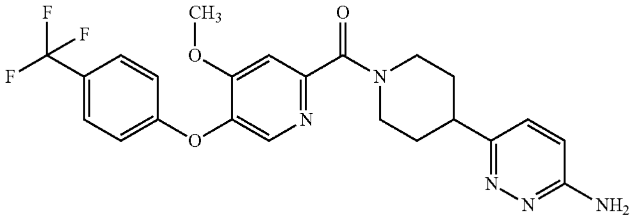 [SMILES: COc1cc(C(=O)N2CCC(c3ccc(N)nn3)CC2)ncc1Oc1ccc(C(F)(F)F)cc1] | [4-(6-Amino-pyridazin-3-yl)-piperidin-1-yl]-[4-methoxy-5-(4-trifluoromethyl-phenoxy)-pyridin-2-yl]-methanone |
| 34 | 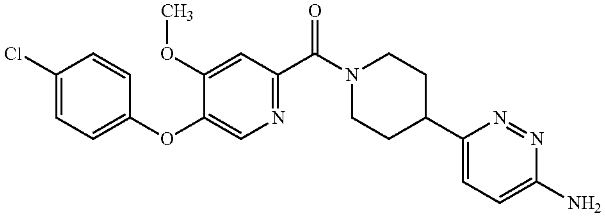 [SMILES: COc1cc(C(=O)N2CCC(c3ccc(N)nn3)CC2)ncc1Oc1ccc(Cl)cc1] | [4-(6-Amino-pyridazin-3-yl)-piperidin-1-yl]-[5-(4-chloro-phenoxy)-4-methoxy-pyridin-2-yl]-methanone |

TABLE 1-continued

| Cpd No. | Structure | Compound Name |
|---|---|---|
| 35 | 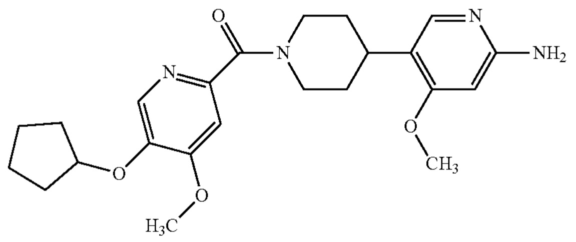 [SMILES: COc1cc(C(=O)N2CCC(c3cnc(N)cc3OC)CC2)ncc1OC1CCCC1] | (6-Amino-4-methoxy-3',4',5',6'-tetrahydro-2'H-[3,4']bipyridinyl-1'-yl)-(5-cyclopentyloxy-4-methoxy-pyridin-2-yl)-methanone |
| 36 | 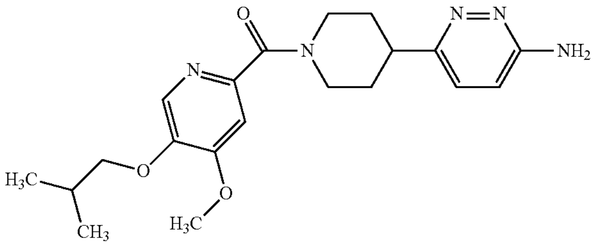 | [4-(6-Amino-pyridazin-3-yl)-piperidin-1-yl]-(5-isobutoxy-4-methoxy-pyridin-2-yl)-methanone |
| 37 | 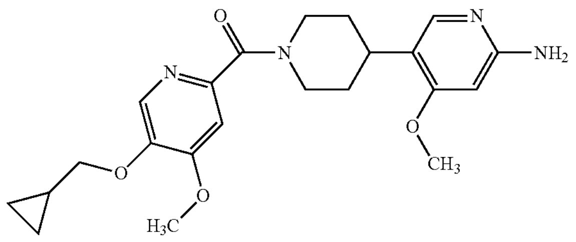 | (6-Amino-4-methoxy-3',4',5',6'-tetrahydro-2'H-[3,4']bipyridinyl-1'-yl)-(5-cyclopropylmethoxy-4-methoxy-pyridin-2-yl)-methanone |
| 38 | 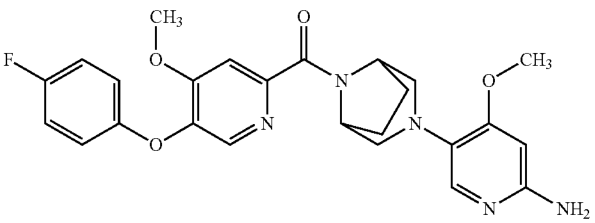 [SMILES: COc1cc(C(=O)N2C3CCC2CN(c2cnc(N)cc2OC)C3)ncc1Oc1ccc(F)cc1] | [3-(6-Amino-4-methoxy-pyridin-3-yl)-3,8-diaza-bicyclo[3.2.1]oct-8-yl]-[5-(4-fluoro-phenoxy)-4-methoxy-pyridin-2-yl]-methanone |
| 39 | 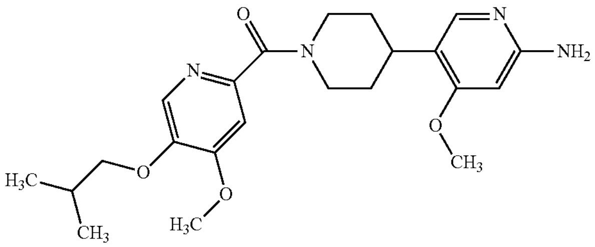 [SMILES: COc1cc(C(=O)N2CCC(c3cnc(N)cc3OC)CC2)ncc1OCC(C)C] | (6-Amino-4-methoxy-3',4',5',6'-tetrahydro-2'H-[3,4']bipyridinyl-1'-yl)-(5-isobutoxy-4-methoxy-pyridin-2-yl)-methanone |
| 40 | 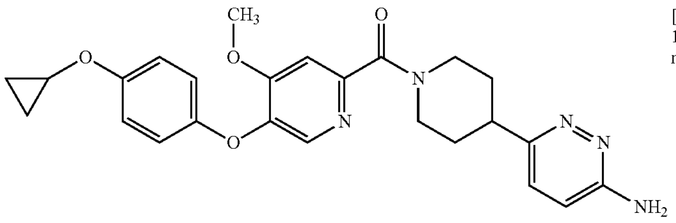 | [4-(6-Amino-pyridazin-3-yl)-piperidin-1-yl]-[5-(4-cyclopropoxy-phenoxy)-4-methoxy-pyridin-2-yl]-methanone |

TABLE 1-continued

| Cpd No. | Structure | Compound Name |
| --- | --- | --- |
| 41 | 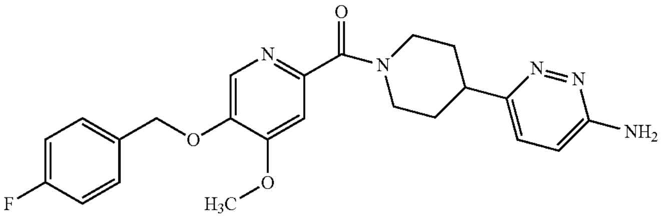 [SMILES: COc1cc(C(=O)N2CCC(c3ccc(N)nn3)CC2)ncc1OCc1ccc(F)cc1] | [4-(6-Amino-pyridazin-3-yl)-piperidin-1-yl]-[5-(4-fluoro-benzyloxy)-4-methoxy-pyridin-2-yl]-methanone |
| 42 | 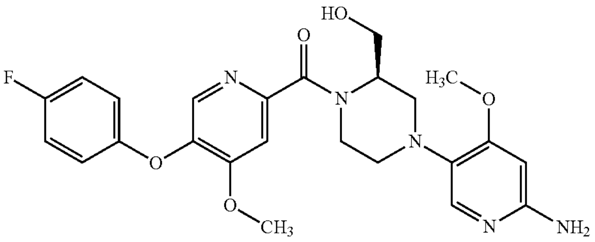 [SMILES: COc1cc(C(=O)N2CCN(c3cnc(N)cc3OC)C[C@@H]2CO)ncc1Oc1ccc(F)cc1] | [(R)-4-(6-Amino-4-methoxy-pyridin-3-yl)-2-hydroxymethyl-piperazin-1-yl]-[5-(4-fluoro-phenoxy)-4-methoxy-pyridin-2-yl]-methanone |
| 43 | 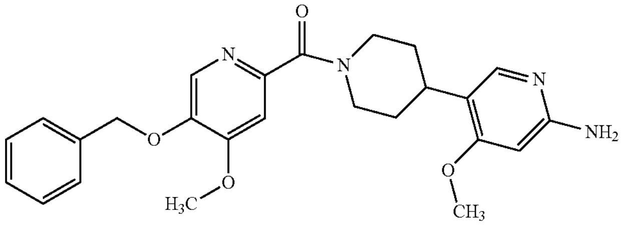 [SMILES: COc1cc(C(=O)N2CCC(c3cnc(N)cc3OC)CC2)ncc1OCc1ccccc1] | (6-Amino-4-methoxy-3',4',5',6'-tetrahydro-2'H-[3,4']bipyridinyl-1'-yl)-(5-benzyloxy-4-methoxy-pyridin-2-yl)-methanone |
| 44 | 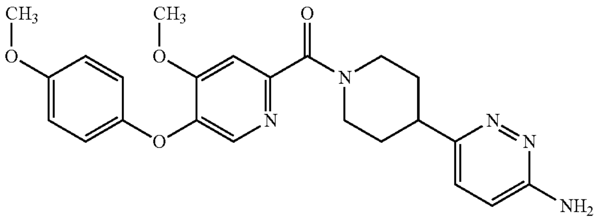 [SMILES: COc1ccc(Oc2cnc(C(=O)N3CCC(c4ccc(N)nn4)CC3)cc2OC)cc1] | [4-(6-Amino-pyridazin-3-yl)-piperidin-1-yl]-[4-methoxy-5-(4-methoxy-phenoxy)-pyridin-2-yl]-methanone |
| 45 | 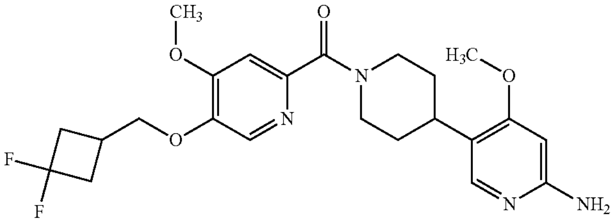 [SMILES: COc1cc(C(=O)N2CCC(c3cnc(N)cc3OC)CC2)ncc1OCC1CC(F)(F)C1] | (6-Amino-4-methoxy-3',4',5',6'-tetrahydro-2'H-[3,4']bipyridinyl-1'-yl)-[5-(3,3-difluoro-cyclobutylmethoxy)-4-methoxy-pyridin-2-yl]-methanone |
| 46 | 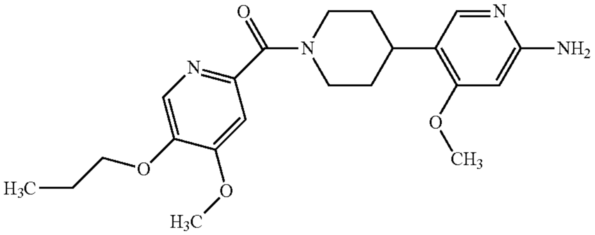 [SMILES: CCCOc1cnc(C(=O)N2CCC(c3cnc(N)cc3OC)CC2)cc1OC] | (6-Amino-4-methoxy-3',4',5',6'-tetrahydro-2'H-[3,4']bipyridinyl-1'-yl)-(4-methoxy-5-propoxy-pyridin-2-yl)-methanone |

TABLE 1-continued

| Cpd No. | Structure | Compound Name |
| --- | --- | --- |
| 47 | 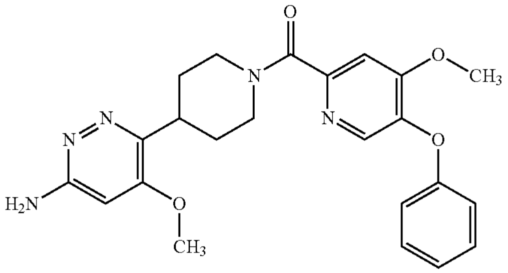 [SMILES: COc1cc(C(=O)N2CCC(c3nnc(N)cc3OC)CC2)ncc1Oc1ccccc1] | [4-(6-Amino-4-methoxy-pyridazin-3-yl)-piperidin-1-yl]-(4-methoxy-5-phenoxy-pyridin-2-yl)-methanone |
| 48 | 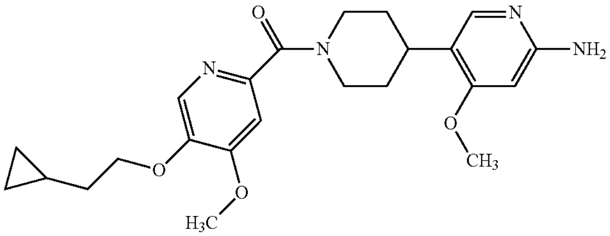 [SMILES: COc1cc(C(=O)N2CCC(c3cnc(N)cc3OC)CC2)ncc1OCCC1CC1] | (6-Amino-4-methoxy-3',4',5',6'-tetrahydro-2'H-[3,4']bipyridinyl-1'-yl)-[5-(2-cyclopropyl-ethoxy)-4-methoxy-pyridin-2-yl]-methanone |
| 49 | 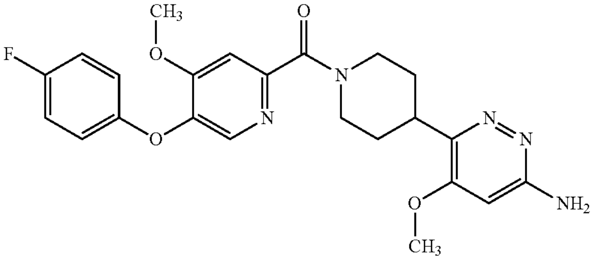 [SMILES: COc1cc(C(=O)N2CCC(c3nnc(N)cc3OC)CC2)ncc1Oc1ccc(F)cc1] | [4-(6-Amino-4-methoxy-pyridazin-3-yl)-piperidin-1-yl]-[5-(4-fluoro-phenoxy)-4-methoxy-pyridin-2-yl]-methanone |
| 50 | 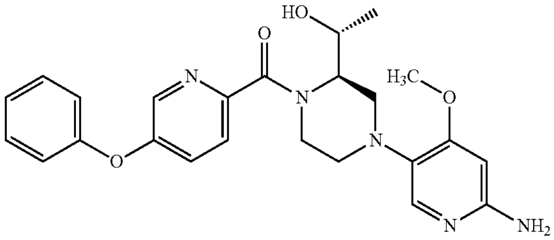 [SMILES: COc1cc(N)ncc1N1CCN(C(=O)c2ccc(Oc3ccccc3)cn2)[C@@H]([C@@H](C)O)C1] | (1R)-1-[(2R)-4-(6-amino-4-methoxypyridin-3-yl)-1-(5-phenoxypyridine-2-carbonyl) piperazin-2-yl]ethan-1-ol |
| 51 | 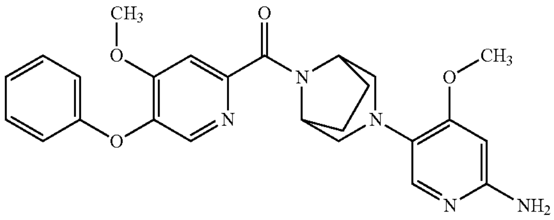 [SMILES: COc1cc(C(=O)N2C3CCC2CN(c2cnc(N)cc2OC)C3)ncc1Oc1ccccc1] | [3-(6-Amino-4-methoxy-pyridin-3-yl)-3,8-diaza-bicyclo[3.2.1]oct-8-yl]-(4-methoxy-5-phenoxy-pyridin-2-yl)-methanone |
| 52 | 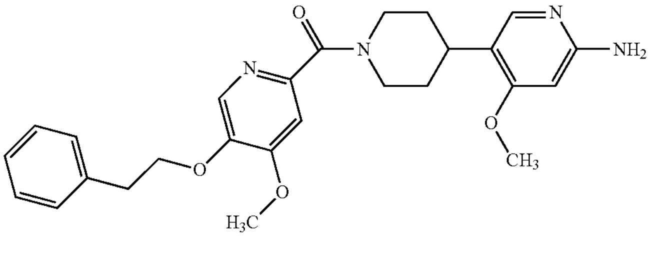 [SMILES: COc1cc(C(=O)N2CCC(c3cnc(N)cc3OC)CC2)ncc1OCCc1ccccc1] | (6-Amino-4-methoxy-3',4',5',6'-tetrahydro-2'H-[3,4']bipyridinyl-1'-yl)-(4-methoxy-5-phenethyloxy-pyridin-2-yl)-methanone |

TABLE 1-continued

| Cpd No. | Structure | Compound Name |
| --- | --- | --- |
| 53 | 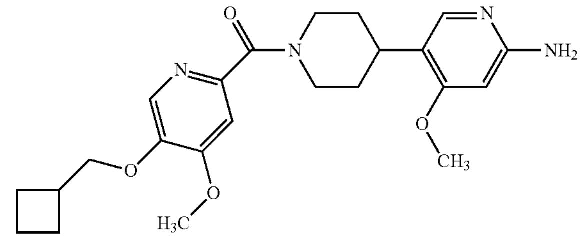 [SMILES: COc1cc(C(=O)N2CCC(c3cnc(N)cc3OC)CC2)ncc1OCC1CCC1] | (6-Amino-4-methoxy-3',4',5',6'-tetrahydro-2'H-[3,4']bipyridinyl-1'-yl)-(5-cyclobutylmethoxy-4-methoxy-pyridin-2-yl)-methanone |
| 54 | 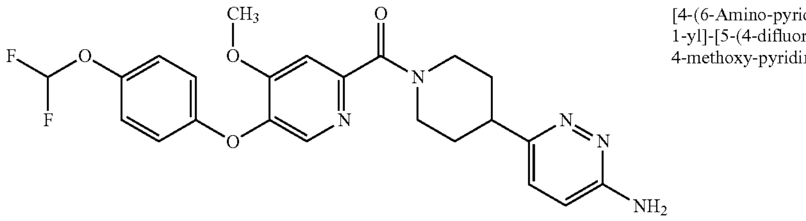 | [4-(6-Amino-pyridazin-3-yl)-piperidin-1-yl]-[5-(4-difluoromethoxy-phenoxy)-4-methoxy-pyridin-2-yl]-methanone |
| 55 | 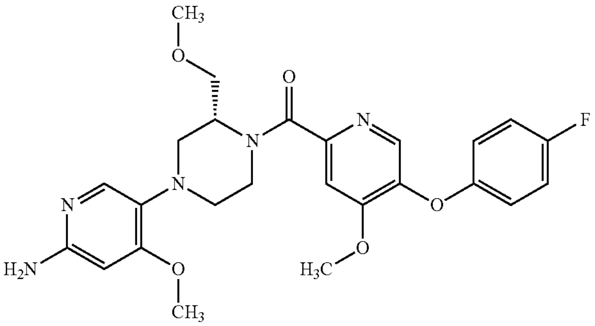 [SMILES: COC[C@H]1CN(c2cnc(N)cc2OC)CCN1C(=O)c1cc(OC)c(Oc2ccc(F)cc2)cn1] | [(R)-4-(6-Amino-4-methoxy-pyridin-3-yl)-2-methoxymethyl-piperazin-1-yl]-[5-(4-fluoro-phenoxy)-4-methoxy-pyridin-2-yl]-methanone |
| 56 | 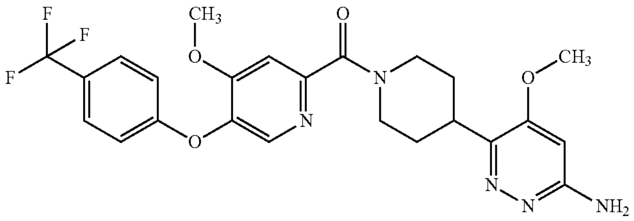 [SMILES: COc1cc(C(=O)N2CCC(c3nnc(N)cc3OC)CC2)ncc1Oc1ccc(C(F)(F)F)cc1] | [4-(6-Amino-4-methoxy-pyridazin-3-yl)-piperidin-1-yl]-[4-methoxy-5-(4-trifluoromethyl-phenoxy)-pyridin-2-yl]-methanone |
| 57 | 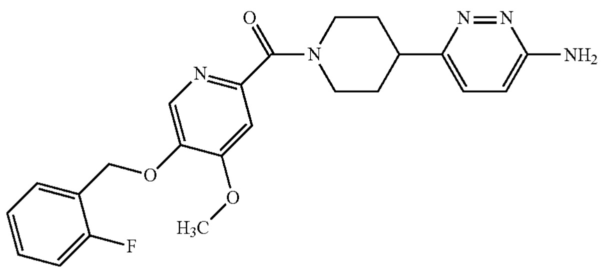 [SMILES: COc1cc(C(=O)N2CCC(c3ccc(N)nn3)CC2)ncc1OCc1ccccc1F] | [4-(6-Amino-pyridazin-3-yl)-piperidin-1-yl]-[5-(2-fluoro-benzyloxy)-4-methoxy-pyridin-2-yl]-methanone |
| 58 | 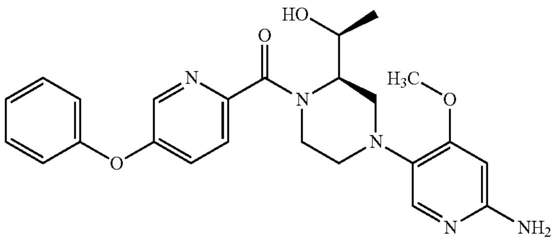 [SMILES: COc1cc(N)ncc1N1CCN(C(=O)c2ccc(Oc3ccccc3)cn2)[C@@H]([C@H](C)O)C1] | (7S)-1-[(2R)-4-(6-amino-4-methoxypyridin-3-yl)-1-(5-phenoxypyridine-2-carbonyl) piperazin-2-yl]ethan-1-ol |

TABLE 1-continued

| Cpd No. | Structure | Compound Name |
|---|---|---|
| 59 | 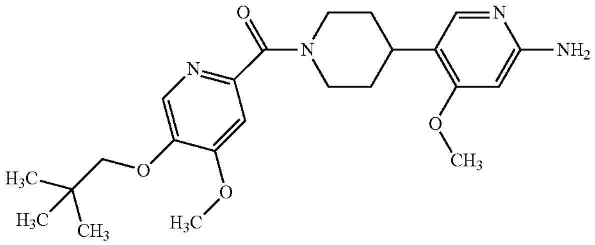 [SMILES: COc1cc(C(=O)N2CCC(c3cnc(N)cc3OC)CC2)ncc1OCC(C)(C)C] | (6-Amino-4-methoxy-3',4',5',6'-tetrahydro-2'H-[3,4']bipyridinyl-1'-yl)-[5-(2,2-dimethyl-propoxy)-4-methoxy-pyridin-2-yl]-methanone |
| 60 | 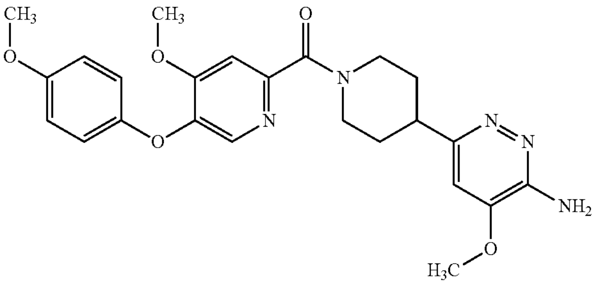 [SMILES: COc1ccc(Oc2cnc(C(=O)N3CCC(c4cc(OC)c(N)nn4)CC3)cc2OC)cc1] | [4-(6-Amino-5-methoxy-pyridazin-3-yl)-piperidin-1-yl]-[4-methoxy-5-(4-methoxy-phenoxy)-pyridin-2-yl]-methanone |
| 61 | 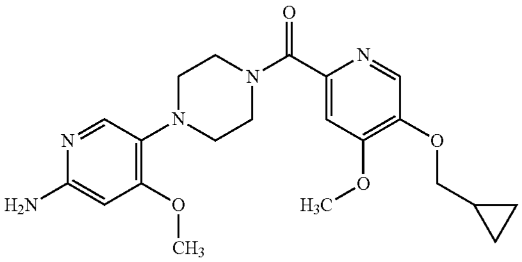 [SMILES: COc1cc(C(=O)N2CCN(c3cnc(N)cc3OC)CC2)ncc1OCC1CC1] | [4-(6-Amino-4-methoxy-pyridin-3-yl)-piperazin-1-yl]-(5-cyclopropylmethoxy-4-methoxy-pyridin-2-yl)-methanone |
| 62 | 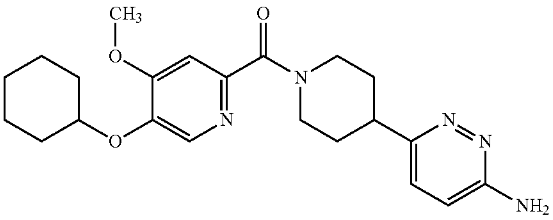 [SMILES: COc1cc(C(=O)N2CCC(c3ccc(N)nn3)CC2)ncc1OC1CCCCC1] | [4-(6-Amino-pyridazin-3-yl)-piperidin-1-yl]-(5-cyclohexyloxy-4-methoxy-pyridin-2-yl)-methanone |
| 63 | 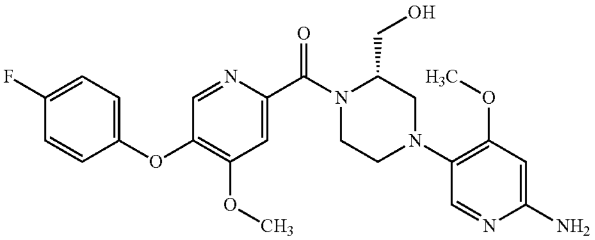 [SMILES: COc1cc(C(=O)N2CCN(c3cnc(N)cc3OC)C[C@H]2CO)ncc1Oc1ccc(F)cc1] | [(S)-4-(6-Amino-4-methoxy-pyridin-3-yl)-2-hydroxymethyl-piperazin-1-yl]-[5-(4-fluoro-phenoxy)-4-methoxy-pyridin-2-yl]-methanone |
| 64 | 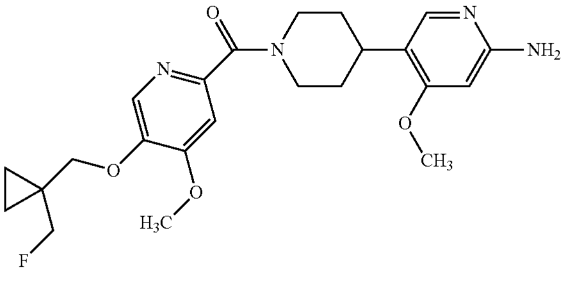 [SMILES: COc1cc(C(=O)N2CCC(c3cnc(N)cc3OC)CC2)ncc1OCC1(CF)CC1] | (6-Amino-4-methoxy-3',4',5',6'-tetrahydro-2'H-[3,4']bipyridinyl-1'-yl)-[5-(1-fluoromethyl-cyclopropyl methoxy)-4-methoxy-pyridin-2-yl]-methanone |

TABLE 1-continued

| Cpd No. | Structure | Compound Name |
|---|---|---|
| 65 | 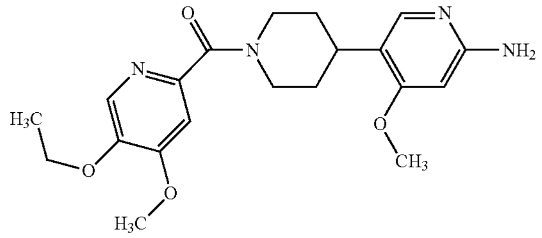 [SMILES: CCOc1cnc(C(=O)N2CCC(c3cnc(N)cc3OC)CC2)cc1OC] | (6-Amino-4-methoxy-3',4',5',6'-tetrahydro-2'H-[3,4']bipyridinyl-1'-yl)-(5-ethoxy-4-methoxy-pyridin-2-yl)-methanone |
| 66 | 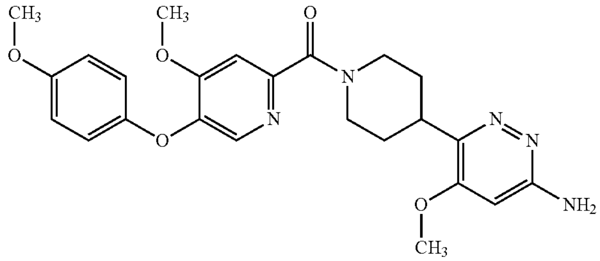 [SMILES: COc1ccc(Oc2cnc(C(=O)N3CCC(c4nnc(N)cc4OC)CC3)cc2OC)cc1] | [4-(6-Amino-4-methoxy-pyridazin-3-yl)-piperidin-1-yl]-[4-methoxy-5-(4-methoxy-phenoxy)-pyridin-2-yl]-methanone |
| 67 | 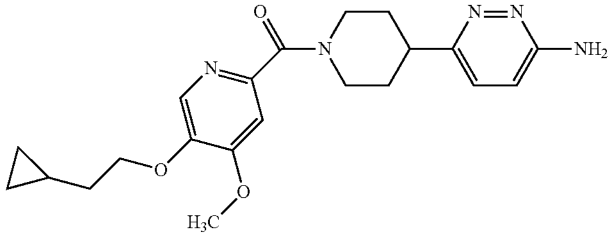 [SMILES: COc1cc(C(=O)N2CCC(c3ccc(N)nn3)CC2)ncc1OCCC1CC1] | [4-(6-Amino-pyridazin-3-yl)-piperidin-1-yl]-[5-(2-cyclopropyl-ethoxy)-4-methoxy-pyridin-2-yl]-methanone |
| 68 | 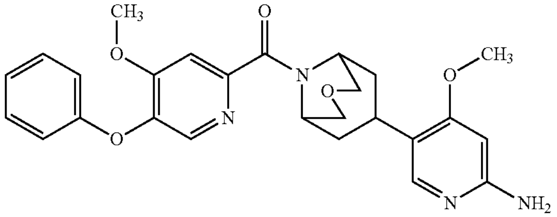 [SMILES: COc1cc(C(=O)N2C3COCC2CC(c2cnc(N)cc2OC)C3)ncc1Oc1ccccc1] | [7-(6-Amino-4-methoxy-pyridin-3-yl)-3-oxa-9-aza-bicyclo[3.3.1]non-9-yl]-(4-methoxy-5-phenoxy-pyridin-2-yl)-methanone |
| 69 | 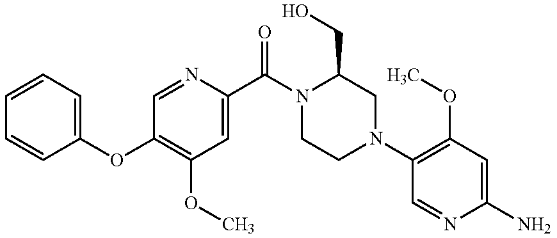 [SMILES: COc1cc(C(=O)N2CCN(c3cnc(N)cc3OC)C[C@@H]2CO)ncc1Oc1ccccc1] | [(R)-4-(6-Amino-4-methoxy-pyridin-3-yl)-2-hydroxymethyl-piperazin-1-yl]-(4-methoxy-5-phenoxy-pyridin-2-yl)-methanone |
| 70 | 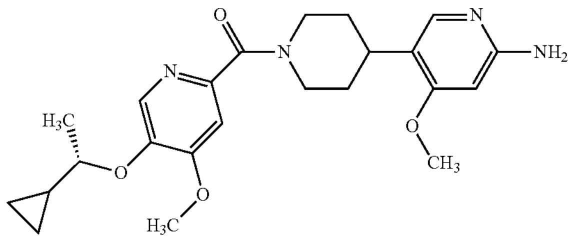 [SMILES: COc1cc(C(=O)N2CCC(c3cnc(N)cc3OC)CC2)ncc1O[C@@H](C)C1CC1] | (6-Amino-4-methoxy-3',4',5',6'-tetrahydro-2'H-[3,4']bipyridinyl-1'-yl)-[5-((S)-1-cyclopropyl-ethoxy)-4-methoxy-pyridin-2-yl]-methanone |

TABLE 1-continued

| Cpd No. | Structure | Compound Name |
| --- | --- | --- |
| 71 | 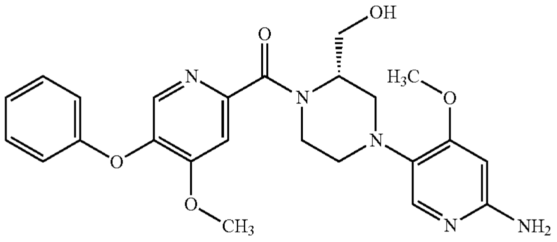 [SMILES: COc1cc(C(=O)N2CCN(c3cnc(N)cc3OC)C[C@H]2CO)ncc1Oc1ccccc1] | [(S)-4-(6-Amino-4-methoxy-pyridin-3-yl)-2-hydroxymethyl-piperazin-1-yl]-(4-methoxy-5-phenoxy-pyridin-2-yl)-methanone |
| 72 | 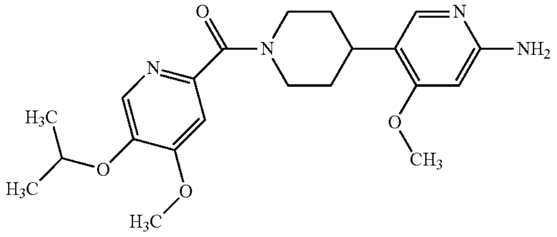 [SMILES: COc1cc(C(=O)N2CCC(c3cnc(N)cc3OC)CC2)ncc1OC(C)C] | (6-Amino-4-methoxy-3',4',5',6'-tetrahydro-2'H-[3,4']bipyridinyl-1'-yl)-(5-isopropoxy-4-methoxy-pyridin-2-yl)-methanone |
| 73 | 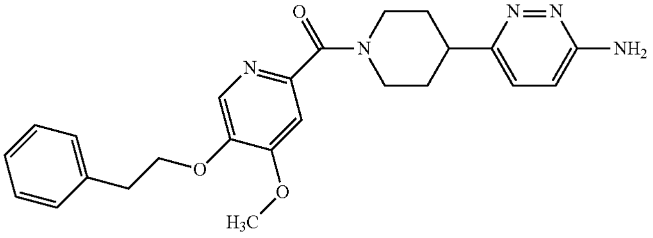 [SMILES: COc1cc(C(=O)N2CCC(c3ccc(N)nn3)CC2)ncc1OCCc1ccccc1] | [4-(6-Amino-pyridazin-3-yl)-piperidin-1-yl]-(4-methoxy-5-phenethyloxy-pyridin-2-yl)-methanone |
| 74 | 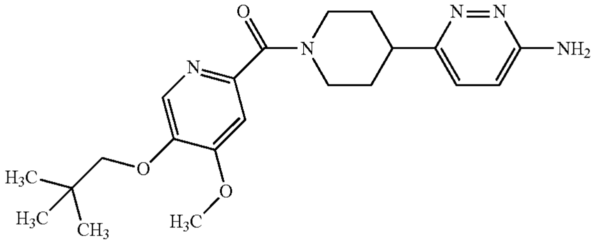 [SMILES: COc1cc(C(=O)N2CCC(c3ccc(N)nn3)CC2)ncc1OCC(C)(C)C] | [4-(6-Amino-pyridazin-3-yl)-piperidin-1-yl]-[5-(2,2-dimethyl-propoxy)-4-methoxy-pyridin-2-yl]-methanone |
| 75 | 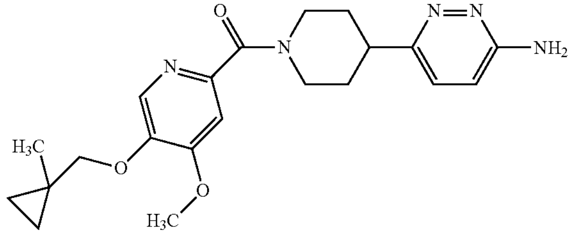 [SMILES: COc1cc(C(=O)N2CCC(c3ccc(N)nn3)CC2)ncc1OCC1(C)CC1] | [4-(6-Amino-pyridazin-3-yl)-piperidin-1-yl]-[4-methoxy-5-(1-methyl-cyclopropylmethoxy)-pyridin-2-yl]-methanone |
| 76 | 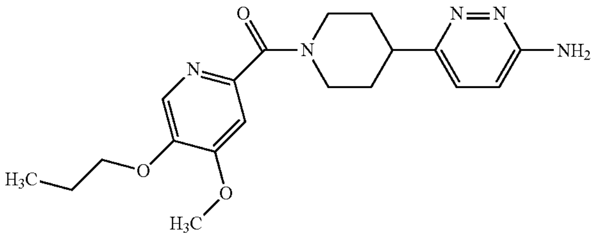 [SMILES: CCCOc1cnc(C(=O)N2CCC(c3ccc(N)nn3)CC2)cc1OC] | [4-(6-Amino-pyridazin-3-yl)-piperidin-1-yl]-(4-methoxy-5-propoxy-pyridin-2-yl)-methanone |

TABLE 1-continued

| Cpd No. | Structure | Compound Name |
|---|---|---|
| 77 | 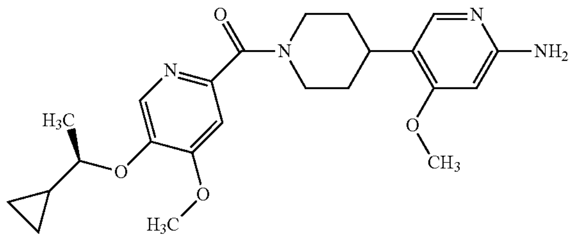 [SMILES: COc1cc(C(=O)N2CCC(c3cnc(N)cc3OC)CC2)ncc1O[C@H](C)C1CC1] | (6-Amino-4-methoxy-3',4',5',6'-tetrahydro-2'H-[3,4']bipyridinyl-1'-yl)-[5-((R)-1-cyclopropyl-ethoxy)-4-methoxy-pyridin-2-yl]-methanone |
| 78 | 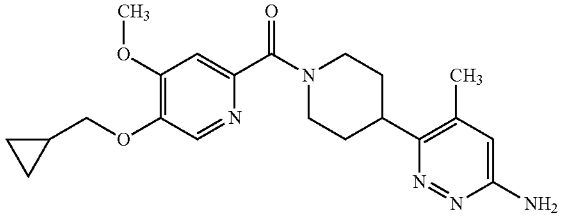 [SMILES: COc1cc(C(=O)N2CCC(c3nnc(N)cc3C)CC2)ncc1OCC1CC1] | [4-(6-Amino-4-methyl-pyridazin-3-yl)-piperidin-1-yl]-(5-cyclopropylmethoxy-4-methoxy-pyridin-2-yl)-methanone |
| 79 | 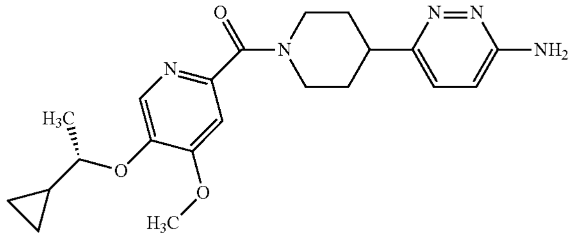 [SMILES: COc1cc(C(=O)N2CCC(c3ccc(N)nn3)CC2)ncc1O[C@@H](C)C1CC1] | [4-(6-Amino-pyridazin-3-yl)-piperidin-1-yl]-[5-((S)-1-cyclopropyl-ethoxy)-4-methoxy-pyridin-2-yl]-methanone |
| 80 | 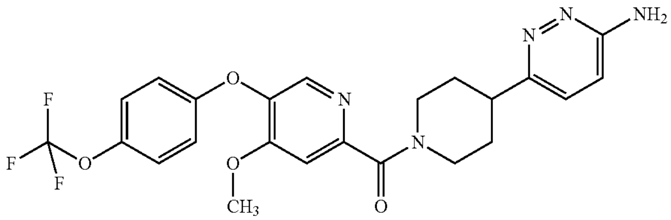 [SMILES: COc1cc(C(=O)N2CCC(c3ccc(N)nn3)CC2)ncc1Oc1ccc(OC(F)(F)F)cc1] | [4-(6-Amino-pyridazin-3-yl)-piperidin-1-yl]-[4-methoxy-5-(4-trifluoromethoxy-phenoxy)-pyridin-2-yl]-methanone |
| 81 | 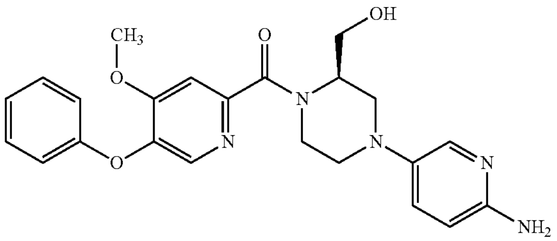 [SMILES: COc1cc(C(=O)N2CCN(c3ccc(N)nc3)C[C@@H]2CO)ncc1Oc1ccccc1] | [(R)-4-(6-Amino-pyridin-3-yl)-2-hydroxymethyl-piperazin-1-yl]-(4-methoxy-5-phenoxy-pyridin-2-yl)-methanone |
| 82 | 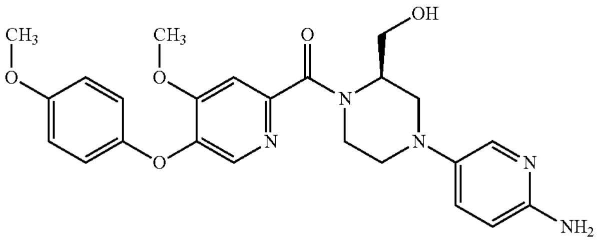 [SMILES: COc1ccc(Oc2cnc(C(=O)N3CCN(c4ccc(N)nc4)C[C@@H]3CO)cc2OC)cc1] | [(R)-4-(6-Amino-pyridin-3-yl)-2-hydroxymethyl-piperazin-1-yl]-[4-methoxy-5-(4-methoxy-phenoxy)-pyridin-2-yl]-methanone |

TABLE 1-continued

| Cpd No. | Structure | Compound Name |
| --- | --- | --- |
| 83 | 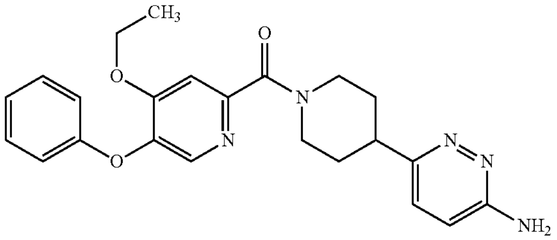 [SMILES: CCOc1cc(C(=O)N2CCC(c3ccc(N)nn3)CC2)ncc1Oc1ccccc1] | [4-(6-Amino-pyridazin-3-yl)-piperidin-1-yl]-[5-(phenoxy)-4-ethoxy-pyridin-2-yl]-methanone |
| 84 | 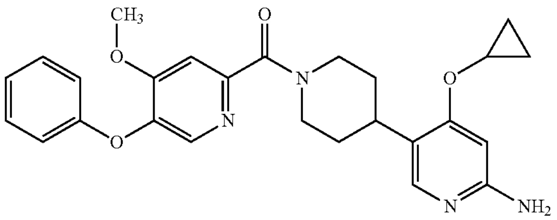 [SMILES: COc1cc(C(=O)N2CCC(c3cnc(N)cc3OC3CC3)CC2)ncc1Oc1ccccc1] | (6-Amino-4-cyclopropoxy-3',4',5',6'-tetrahydro-2'H-[3,4']bipyridinyl-1'-yl)-[5-(phenoxy)-4-methoxy-pyridin-2-yl]-methanone |
| 85 | 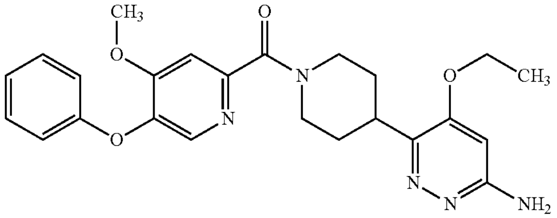 [SMILES: CCOc1cc(N)nnc1C1CCN(C(=O)c2cc(OC)c(Oc3ccccc3)cn2)CC1] | [4-(6-Amino-4-ethoxy-pyridazin-3-yl)-piperidin-1-yl]-[4-methoxy-5-(phenoxy)-pyridin-2-yl]-methanone |
| 86 | 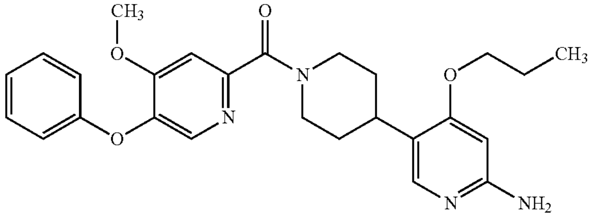 [SMILES: CCCOc1cc(N)ncc1C1CCN(C(=O)c2cc(OC)c(Oc3ccccc3)cn2)CC1] | (6-Amino-4-propoxy-3',4',5',6'-tetrahydro-2'H-[3,4']bipyridinyl-1'-yl)-[5-(phenoxy)-4-methoxy-pyridin-2-yl]-methanone |
| 87 | 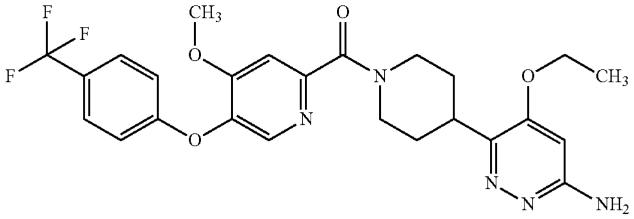 [SMILES: CCOc1cc(N)nnc1C1CCN(C(=O)c2cc(OC)c(Oc3ccc(C(F)(F)F)cc3)cn2)CC1] | 5-Ethoxy-6-(1-{4-methoxy-5-[4-(trifluoromethyl)phenoxy]pyridine-2-carbonyl}piperidin-4-yl)pyridazin-3-amine |
| 88 | 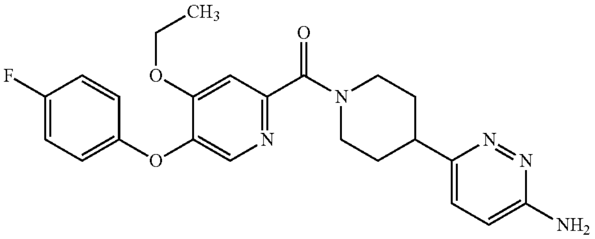 [SMILES: CCOc1cc(C(=O)N2CCC(c3ccc(N)nn3)CC2)ncc1Oc1ccc(F)cc1] | [4-(6-Amino-pyridazin-3-yl)-piperidin-1-yl]-[5-(4-fluoro-phenoxy)-4-ethoxy-pyridin-2-yl]-methanone |

TABLE 1-continued

| Cpd No. | Structure | Compound Name |
| --- | --- | --- |
| 89 | 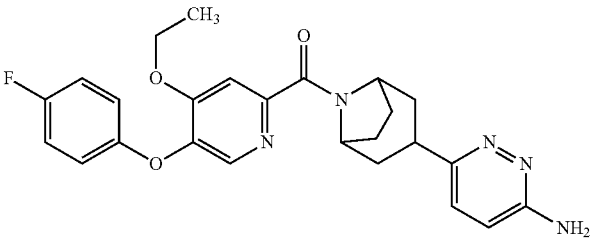 [SMILES: CCOc1cc(C(=O)N2C3CCC2CC(c2ccc(N)nn2)C3)ncc1Oc1ccc(F)cc1] | [3-(6-Amino-pyridazin-3-yl)-8-aza-bicyclo[3.2.1]oct-8-yl]-[4-ethoxy-5-(4-fluoro-phenoxy)-pyridin-2-yl]-methanone |
| 90 | 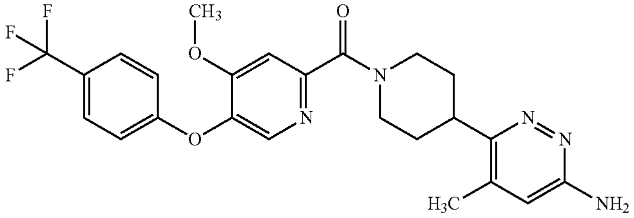 [SMILES: COc1cc(C(=O)N2CCC(c3nnc(N)cc3C)CC2)ncc1Oc1ccc(C(F)(F)F)cc1] | 6-(1-{4-Methoxy-5-[4-(trifluoro-methyl)phenoxy]pyridine-2-carbonyl}piperidin-4-yl)-5-methylpyridazin-3-amine |
| 91 | 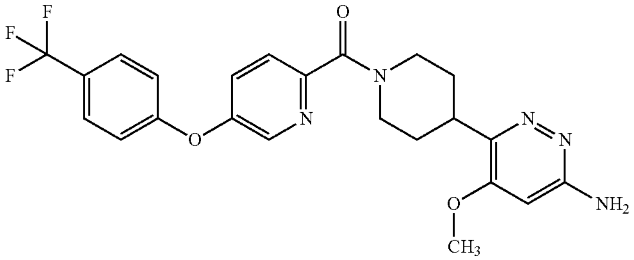 [SMILES: COc1cc(N)nnc1C1CCN(C(=O)c2ccc(Oc3ccc(C(F)(F)F)cc3)cn2)CC1] | 5-Methoxy-6-(1-{5-[4-(trifluoro-methyl)-phenoxy]-pyridine-2-carbonyl}piperidin-4-yl)-pyridazin-3-amine |
| 92 | 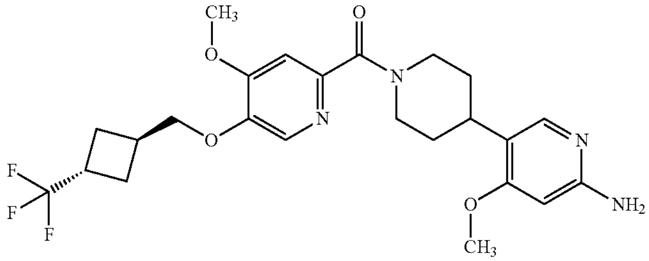 [SMILES: COc1cc(C(=O)N2CCC(c3cnc(N)cc3OC)CC2)ncc1OC[C@H]1C[C@H](C(F)(F)F)C1] | 4-Methoxy-5-[1-(4-methoxy-5-{[trans-3-(trifluoromethyl)cyclobutyl]-methoxy}pyridine-2-carbonyl)-piperidin-4-yl]pyridin-2-amine |
| 93 | 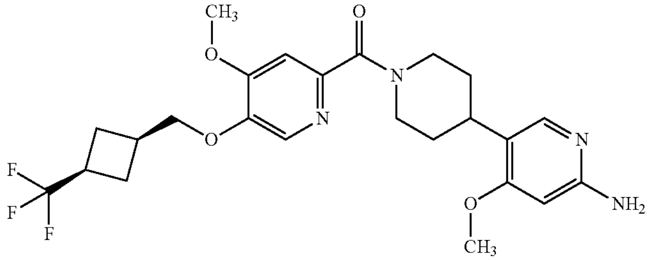 [SMILES: COc1cc(C(=O)N2CCC(c3cnc(N)cc3OC)CC2)ncc1OC[C@H]1C[C@@H](C(F)(F)F)C1] | 4-Methoxy-5-[1-(4-methoxy-5-{[(cis-3-(trifluoromethyl)-cyclobutyl]methoxy}-pyridine-2-carbonyl)piperidin-4-yl]pyridin-2-amine |
| 94 | 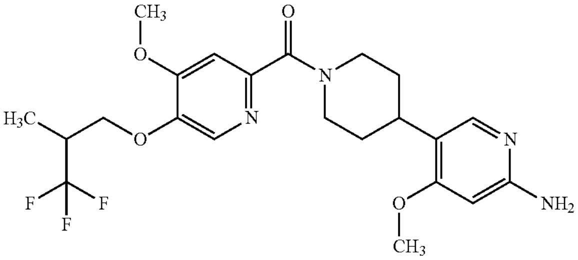 [SMILES: COc1cc(C(=O)N2CCC(c3cnc(N)cc3OC)CC2)ncc1OCC(C)C(F)(F)F] | 4-Methoxy-5-(1-{4-methoxy-5-[(2)-3,3,3-trifluoro-2-methylpropoxy]-pyridine-2-carbonyl}piperidin-4-yl)pyridin-2-amine |

TABLE 1-continued

| Cpd No. | Structure | Compound Name |
| --- | --- | --- |
| 95 | 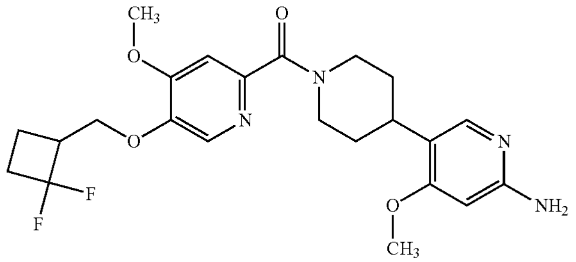 [SMILES: COc1cc(C(=O)N2CCC(c3cnc(N)cc3OC)CC2)ncc1OCC1CCC1(F)F] | 5-(1-{5-[(2,2-Difluorocyclobutyl)-methoxy]-4-methoxy-pyridine-2-carbonyl}-piperidin-4-yl)-4-methoxypyridin-2-amine |

In another embodiment, the invention relates to a method of using any of the compounds 1 to 95 depicted in Table 1 above, and the pharmaceutically acceptable salts thereof, for treating, or reducing the severity of a disorder associated with vascular hyperpermeability and/or conditions arising therefrom which is selected from the group 1 consisting of pulmonary (lung) edema,
idiopathic interstitial pneumonia,
idiopathic pulmonary fibrosis (IPF) and acute exacerbation IPF,
(ARDS), not infection-related,
acute lung injury (ALI), and
lung ischemia reperfusion, or which is selected from the group 2 consisting of ARDS, related to infection,
severe acute respiratory syndrome (SARS),
middle eastern respiratory syndrome (MERS),
sepsis,
severe sepsis, and
septic shock.

In another embodiment, the invention relates to the embodiments immediately above, wherein any one of compounds 6, 16, 17, 29, 31, 33, 34, 40, 41, 44, 49, 54, 56, 57, 66, 80, 83, 85, 87, 88, and 90 depicted in Table 1, or a pharmaceutically acceptable salt thereof, is administered to the patient.

Any method of treatment embodiments one to twenty-four as well as any method of treatment embodiments referring to one or more of compounds 1 to 95 disclosed hereinbefore is understood to have a corresponding embodiment in the European second medical use format "compound X for use in the treatment of disease Y" or
"pharmaceutical composition comprising compound X for use in the therapy of disease Y",
wherein compound X stands for a compound of formula I or one or more of compounds 1 to 95 disclosed hereinbefore, and disease Y stands for a disorder associated with vascular hyperpermeability and/or conditions arising therefrom and the specific conditions of group 1 and 2 disclosed hereinbefore.

Exemplary, the broadest embodiments in the European second medical use format read as follows:

In a further embodiment the invention relates to a TRPC6 inhibitor of formula (I), as defined hereinbefore, for use in the treatment of a disorder associated with vascular hyperpermeability and/or conditions arising therefrom.

In yet a further embodiment the invention relates to a pharmaceutical composition comprising a TRPC6 inhibitor of formula (I), as defined hereinbefore, for use in the treatment of a disorder associated with vascular hyperpermeability and/or conditions arising therefrom.

General Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general in groups like HO, $H_2N$, (O)S, $(O)_2S$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl" means an aryl group, which is bound to a $C_{1-3}$-alkyl-group, the latter of which is bound to the core or to the group to which the substituent is attached.

In case a compound is depicted in form of a chemical name and as a formula in case of any discrepancy the formula shall prevail.

The term "substituted" as used herein, means that any one or more hydrogens on the designated atom is replaced with a selection from the indicated group, provided that the designated atom's normal valence is not exceeded, and that the substitution results in a stable compound.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salt" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, formates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, trifluoroacetates, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19) or with cations from ammonia, L-arginine, calcium, 2,2'-iminobisethanol, L-lysine, magnesium, N-methyl-D-glucamine, potassium, sodium and tris(hydroxymethyl)-aminomethane.

The term halogen generally denotes fluorine, chlorine, bromine and iodine.

The term "$C_{1-n}$-alkyl", wherein n is an integer selected from the group consisting of 2, 3, 4, 5 or 6, preferably 4 or 6, either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$, $H_3C—CH_2—CH_2—CH_2—CH_2—$, $H_3C—CH_2—CH_2—CH(CH_3)—$, $H_3C—CH_2—CH(CH_3)—CH_2—$, $H_3C—CH(CH_3)—CH_2—CH_2—$, $H_3C—CH_2—C(CH_3)_2—$, $H_3C—C(CH_3)_2—CH_2—$, $H_3C—CH(CH_3)—CH(CH_3)—$ and $H_3C—CH_2—CH(CH_2CH_3)—$.

The term "$C_{3-n}$-cycloalkyl", wherein n is an integer from 4 to n, either alone or in combination with another radical denotes a cyclic, saturated, unbranched hydrocarbon radical with 3 to n C atoms. For example, the term $C_{3-7}$-cycloalkyl includes cyclopropyl, cyclobutyl, cyclopentyl, cyclohexyl and cycloheptyl.

By the term "halo" added to an "alkyl", "alkylene" or "cycloalkyl" group (saturated or unsaturated) is such an alkyl or cycloalkyl group wherein one or more hydrogen atoms are replaced by a halogen atom selected from among fluorine, chlorine or bromine, preferably fluorine and chlorine, particularly preferred is fluorine. Examples include: $H_2FC—$, $HF_2C—$, $F_3C—$. Analogously, the term "halo" added to an aryl group (e.g., phenyl) means that one or more hydrogen atoms are replaced by a halogen atom selected from among fluorine, chlorine or bromine, preferably fluorine and chlorine, particularly preferred is fluorine.

The term "carbocyclyl" as used either alone or in combination with another radical, means a mono- bi- or tricyclic ring structure consisting of 3 to 9 carbon atoms and optionally a heteroatom selected from the group consisting of N, O, and S. The term "carbocyclyl" refers to fully saturated ring systems and encompasses fused, bridged and spirocyclic systems.

Many of the terms given above may be used repeatedly in the definition of a formula or group and in each case have one of the meanings given above, independently of one another.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds in Table 1 can exist in more than one tautomeric form. The invention includes methods for using all such tautomers.

In addition, within the scope of the invention is the use of prodrugs of the TRPC6 inhibitors within the methods of treatment of the invention. Prodrugs include those compounds that, upon simple chemical transformation, are modified to produce compounds of the invention.

Simple chemical transformations include hydrolysis, oxidation and reduction. Specifically, when a prodrug is administered to a patient, the prodrug may be transformed into a compound disclosed hereinabove, thereby imparting the desired pharmacological effect.

For all compounds disclosed herein above in this application, in the event the nomenclature is in conflict with the structure, it shall be understood that the compound is defined by the structure.

Assessment of Biological Activity

Example 1: Reduction of LPS-Induced Vascular Leakage in a Mouse Model

Mice are placed in a chamber and exposed to Lipopolysaccharide (LPS, knows as endotoxin and found in outer membrane of Gram-negative bacteria such as *Escherichia Coli*) aerosol (0.8 mg/ml) for 30 min (or Phosphate-Buffered Saline, PBS as vehicle). The TRPC6 inhibitor is given orally 12 h and 2 h before LPS challenge. The mice are euthanized 4 h after the end of the LPS aerosol exposure. Blood is collected for plasma exposure of the compound and the lungs are flushed with 0.8 ml PBS. The broncho-alveolar-lavage is centrifuged at 500 revolutions/min for 10 min and the supernatant is collected for the measurement of total protein according to Lowry measurement by absorbance at 660 nm.

LPS aerosol induced lung edema is characterized by a significant accumulation of Broncho-Alveolar-Lavage protein (BALF protein). The origin of these proteins are albumin from the blood due to the vascular hyperpermeability and proteins from the membranes of lung alveolar cells, which are damaged. In the LPS groups, BALF protein (280-310 μg/ml BALF, FIG. 1*a* and FIG. 1*b*) is significantly higher than BALF protein in the PBS groups (170-180 μg/ml BALF, FIG. 1*a* and FIG. 1*b*). The TRPC6 inhibitor significantly reduced BALF protein concentration of 56% at 3 mg/kg p.o. and 62% at 10 mg/kg p.o. (FIG. 1*c*).

Example 2: Treatment of SARS-CoV-2 Disorders in a Rhesus Monkey Model

The use of the TRPC inhibitors for treating SARS-CoV-2 disorders can be studied in a Rhesus monkey model. Eligible monkeys (male and female, ages 3 to 5 years, body weight 3.5-7.0 kg) are subject to physical examination and show no abnormality. Serological indirect immunofluorescence (IFA) excludes infections with potential simian immunodeficiency virus (SIV), simian retrovirus type D (SRV) and simian T lymphocyte virus type I (STLV-I). Eligible monkeys are sent to a quarantine room for further examination for 14 days. After passing quarantine, monkeys are transferred to the laboratory for adaptive feeding and the experiment is started.

Treatment and Control Groups: Monkeys in the treatment group and positive control group are inoculated with SARS-CoV-2. The TRPC6 inhibitor (solubilized in 5% hydroxypropyl-beta-cyclodextrin) is given intravenously (3 mg/kg) once daily starting 1 dpi (24 h after SARS-CoV-2 inoculation) to 6 dpi (days post-infection) to monkeys in the treatment group. Monkeys in both groups are euthanized at 7 dpi. These groups of monkeys are compared to a negative control group which is inoculated with PBS and treated with the vehicle of TRPC6 (5% hydroxypropyl-beta.cyclodextrin)

Results:

Body weight is measured at 0 dpi and 7 dpi.

Blood samples are collected, 1 ml/time, once every other day. Terminal blood sample (10 ml) are collected and analyzed (ELISA) for IL1β, IL6, IL11, adrenomedullin, angiopoietin-2 and CGRP, PECAM-1 and Surfactant D (SPD).

Lung weight is measured at 7 dpi.

Histopathology and immunohistochemical examination of the lung are performed at 7 dpi. Hematoxylin/eosin (H/E), periodic acid Schiff (PAS) and immunohistochemical (IHC) staining are performed. Severity of lung edema can be evaluated be pathology score.

Exogenous terminal deoxynucleotidyl transferase (TUNEL) assay is performed on lung tissue slides. TUNEL-positive cells may be quantified.

Chest X-ray's are performed at 0 dpi and 7 dpi.

The results of the above measurements and assays can be used to show that the TRPPC inhibitors of the invention are useful for treating disorders of the lung (such as pulmonary (lung) edema) that may arise out of SARS-CoV-2 infection.

Example 3: Reduction of H1N1-Induced Vascular Leakage in a Mouse Model

Mice were inoculated intranasally with 200 PFU (Plaque Formation Unit) of virus Influenza A (strain: PR8/34/H1N1). TRPC6 was given at 3 mg/kg p.o. 2 h after inoculation and once daily from day 1 to day 4. Evans blue was injected intravenously on day 6, 30 min prior to the euthanasia. The Broncho-Alveolar Lavage Fluid (BALF) was collected and centrifuged at 500 revolutions/min for 10 min. The supernatant was collected for the measurement of Evans blue by spectrophotometry at the absorbance of 620 nm At day 6 after inoculation, H1N1 induced lung vascular leakage characterized by an increase in Evans blue extravasation from the blood to the BALF. In the H1N1 group, BALF Evans blue (29 μg/ml) was significantly higher than BALF Evans blue in the vehicle group (7 μg/ml). The TRPC6 inhibitor significantly reduced BALF Evans blue of 24% at 3 mg/kg p.o.

Methods of Therapeutic Use

The inhibition of TRPC6 is an attractive means for treating or alleviating disorders associated with vascular hyperpermeability and/or conditions arising therefrom. The compounds disclosed herein are particularly effective for treating and/or alleviating these disorders, diseases and conditions including, for example: lung vascular hyperpermeability, pulmonary (lung) edema, lung ischemia reperfusion, acute respiratory distress syndrome (ARDS), acute lung injury (ALI), severe acute respiratory syndrome (SARS), Middle Eastern respiratory syndrome (MERS), sepsis, severe sepsis, and septic shock.

In one embodiment, the present invention provides methods for reducing lung vascular hyperpermeability by administering to a patient in need thereof a pharmaceutically effective amount of a TRPC6 inhibitor of formula (I) as defined hereinbefore or of a compound selected from the group consisting of compounds 1 to 95, but preferably of a compound selected from the group consisting of compounds 6, 16, 17, 29, 31, 33, 34, 40, 41, 44, 49, 54, 56, 57, 66, 80, 83, 85, 87, 88, and 90 depicted in Table 1, or a pharmaceutically acceptable salt thereof.

In another embodiment, the present invention provides methods for treating or alleviating pulmonary edema by administering to a patient in need thereof a pharmaceutically effective amount of a TRPC6 inhibitor of formula (I) as defined hereinbefore or of a compound selected from the group consisting of compounds 1 to 95, but preferably of a compound selected from the group consisting of compounds 6, 16, 17, 29, 31, 33, 34, 40, 41, 44, 49, 54, 56, 57, 66, 80, 83, 85, 87, 88, and 90 depicted in Table 1, or a pharmaceutically acceptable salt thereof.

In another embodiment, the present invention provides methods for treating ARDS, including low, mild, and severe ARDS (based on the degree of hypoxemia), by administering to a patient in need thereof a pharmaceutically effective amount of a TRPC6 inhibitor of formula (I) as defined hereinbefore or of a compound selected from the group consisting of compounds 1 to 95, but preferably of a compound selected from the group consisting of compounds 6, 16, 17, 29, 31, 33, 34, 40, 41, 44, 49, 54, 56, 57, 66, 80, 83, 85, 87, 88, and 90 depicted in Table 1, or a pharmaceutically acceptable salt thereof.

In another embodiment, the present invention provides methods for treating ARDS by administering to a patient in need thereof a pharmaceutically effective amount of a TRPC6 inhibitor of formula (I) as defined hereinbefore or of a compound selected from the group consisting of compounds 1 to 95, but preferably of a compound selected from the group consisting of compounds 6, 16, 17, 29, 31, 33, 34, 40, 41, 44, 49, 54, 56, 57, 66, 80, 83, 85, 87, 88, and 90 depicted in Table 1, or a pharmaceutically acceptable salt thereof.

In another embodiment, the present invention provide methods for treating SARS by administering to a patient in need thereof a pharmaceutically effective amount of a TRPC6 inhibitor of formula (I) as defined hereinbefore or of a compound selected from the group consisting of compounds 1 to 95, but preferably of a compound selected from the group consisting of compounds 6, 16, 17, 29, 31, 33, 34, 40, 41, 44, 49, 54, 56, 57, 66, 80, 83, 85, 87, 88, and 90 depicted in Table 1, or a pharmaceutically acceptable salt thereof.

In another embodiment, the present invention provides methods for treating MERS by administering to a patient in need thereof a pharmaceutically effective amount of a TRPC6 inhibitor of formula (I) as defined hereinbefore or of a compound selected from the group consisting of compounds 1 to 95, but preferably of a compound selected from the group consisting of compounds 6, 16, 17, 29, 31, 33, 34, 40, 41, 44, 49, 54, 56, 57, 66, 80, 83, 85, 87, 88, and 90 depicted in Table 1, or a pharmaceutically acceptable salt thereof.

In another embodiment, the present invention provides methods for treating sepsis, severe sepsis, and/or septic shock by administering to a patient in need thereof a pharmaceutically effective amount of a TRPC6 inhibitor of formula (I) as defined hereinbefore or of a compound selected from the group consisting of compounds 1 to 95, but preferably of a compound selected from the group consisting of compounds 6, 16, 17, 29, 31, 33, 34, 40, 41, 44, 49, 54, 56, 57, 66, 80, 83, 85, 87, 88, and 90 depicted in Table 1, or a pharmaceutically acceptable salt thereof.

In one embodiment, the present invention provides methods for treating or alleviating a respiratory disorder or condition described herein that arises from a viral (such as influenza H1N1, Respiratory syncytial virus, Herpesviridae, parainfluenza, adenovirus) or bacterial (such as *Legionella pneumophila, Haemophilus influenzae, Sterptococcus pneumonia, Klebsiella, Mycoplasma* pneumonia; *Staphylococcus aureus*) or fungal (fungal pneumonia) parasites (parasitic pneumonia) infection. Nonlimiting examples of viral infections include human coronavirus (CoV) infections such as SARS-CoV, SARS-CoV-2 and MERS-CoV by administering to a patient in need thereof a pharmaceutically effective amount of a TRPC6 inhibitor of formula (I) as defined hereinbefore or of a compound selected from the group consisting of compounds 1 to 95, but preferably of a compound selected from the group consisting of compounds 6, 16, 17, 29, 31, 33, 34, 40, 41, 44, 49, 54, 56, 57, 66, 80, 83, 85, 87, 88, and 90 depicted in Table 1, or a pharmaceutically acceptable salt thereof.

In another embodiment, the present invention relates to the treatment of a respiratory disorder or condition arising from a viral or bacterial infection, wherein the respiratory disorder or condition is selected from the group consisting of lung vascular hyperpermeability, pulmonary (lung) edema, lung ischemia reperfusion, acute respiratory distress syndrome (ARDS), acute lung injury (ALI), and severe acute respiratory syndrome (SARS) by administering to a patient in need thereof a pharmaceutically effective amount of a TRPC6 inhibitor of formula (I) as defined hereinbefore or of a compound selected from the group consisting of compounds 1 to 95, but preferably of a compound selected from the group consisting of compounds 6, 16, 17, 29, 31, 33, 34, 40, 41, 44, 49, 54, 56, 57, 66, 80, 83, 85, 87, 88, and 90 depicted in Table 1, or a pharmaceutically acceptable salt thereof.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of the invention (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regimen.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, Pharmaceutical Dosage Forms and Drug Delivery Systems, 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

The compounds of the invention may be used alone or in combination of one or more additional therapeutic agents. Nonlimiting examples of additional therapeutic agents may include:

- antimalarials such as hydroxychloroquine or chloroquine, each with or without azithromycin;
- virostatic nucleosid analogs such as remdesivir;
- HIV-protease inhibitors such as lopinavir-ritonavir;
- angiotensin II receptor antagonists (angiotensin receptor blockers (ARBs)) such as candesartan, eprosartan, candesartan, irbesartan, losartan, olmesartan, telmisartan, valsartan, azilsartan, and medoxomil;

angiotensin converting enzyme inhibitors (e.g., benazepril, captopril, enalapril, fosinopril, lisinopril, moexipril, and perindopril);

anticoagulants (e.g. dabigatran, actylise, Warfarin, heparin, and acetylsalicylic acid);

antidiabetics such as alpha-glucosidase inhibitors (e.g., miglitol and acarbose), amylin analogs (e.g., pramlintide), dipeptidyl peptidase 4 inhibitors (e.g., alogliptin, sitagliptin, saxagliptin, and linagliptin), incretin mimetics (e.g., liraglutide, exenatide, liraglutide, exenatide, dulaglutide, albiglutide, and lixisenatide), insulin, meglitinides (e.g., repaglinide and nateglinide), biguanides (e.g., metformin); SGLT-2 inhibitors (e.g., canagliflozin, empagliflozin, and dapagliflozin), sulfonylureas (e.g., chlorpropamide, glimepiride, glyburide, glipizide, glyburide, tolazamide, and tolbutamide), and thiazolidinediones (e.g., rosiglitazone and pioglitazone); CGRP antagonists (such as olcegepant, valcegepant);

bronchodilators including short-acting and long-action beta agonists (e.g., albuterol, levalbuterol, salmeterol, formoterol, arformoterol, vilanterol, indacaterol and olodaterol) and short- and long-acting anticholinergics (ipratropium, tiotropium, umeclidinium, glycopyrrolatei and aclidinium);

steroids such as fluticasone and budesonide; and corticosteroids such as dexamethasone, prednisone, methylprednisolone, and hydrocortisonea.

In one embodiment, the one or more additional therapeutic agents comprises one or more monoclonal antibodies that block infectivity of SARS-CoV-2 including REGN10933 and REGN10987 and combinations or REGN10933 and REGN10987 (REGN-COV2).

In another embodiment the compounds of the invention may be used in combination with anti-IL-6 antibodies, such as tocilizumab, sarilumab, siltuximab, levilimab, olokizumab (CDP6038), elsilimomab, clazakizumab (BMS-945429, ALD518), sirukumab (CNTO 136), levilimab (BCD-089), CPSI-2364 (an apparent macrophage-specific inhibitor of the p38 mitogen-activated protein kinase pathway), ALX-0061, ARGX-109, FE301 and FM101.

In yet another embodiment the compounds of the invention may be used in combination with various kinase inhibitors providing immunomodulatory effects (A. P. Kater et al., Blood Adv. 2021 Feb. 9; 5(3): 913-925), such as TKIs approved or in late-stage development for the treatment of hematological malignancies, including inhibitors of Bruton's tyrosine kinase (BTK), such as ibrutinib, acalabrutinib, zanubrutinib, or tirabrutinib, spleen tyrosine kinase (SYK), such as fostamatinib, entospletinib, or cerdulatinib, BCR-Abl, such as imatinib, nilotinib, dasatinib, bosutinib, ponatinib, or radotinib, phosphatidylinositol 3-kinase (PI3K)/mammalian target of rapamycin (mTOR), such as idelalisib, copanlisib, duvelisib, umbralisib, or temsirolimus, JAK/STAT, such as ruxolitinib, fedratinib, momelotinib, or pacritinib, and FMS-like tyrosine kinase 3 (FLT3), such as midostaurin, sunitinib, sorafenib, gilteritinib, crenolanib, or quizartinib.

In a further embodiment the compounds of the invention may be used in combination with antifibrotics, such as nintedanib or pirfenidone, as patients in need of mechanical ventilation tend to develop lung fibrosis.

When used as combination treatment of a pharmaceutical combination, the compounds of the invention and the one or more additional agents can be administered in the same dosage form or different dosage forms. The compounds of the invention and the one or more additional agents can be administered simultaneously or separately, as part of a regimen.

Example 3: Treatment of SARS-CoV-2 Disorders in Humans

The use of the TPRPC inhibitors for treating SARS-CoV-2 disorders can be studied in adult human patients, for example, to show the efficacy and safety of a TRPC6 inhibitor according to the invention, compared to placebo in reducing risk or severity of acute respiratory distress syndrome (ARDS) in patients hospitalized for COVID-19. This treatment could occur on the background of other therapies shown to have benefit in these patients. One particular TRPC6 inhibitor of the invention (BI 764198) has been shown to be well tolerated in a Phase 1 study in healthy adults (NCT03854552). BI 764198 is expected to reduce vascular hyper-permeability and oedema in the lungs of patients infected with SARS-CoV-2, potentially mitigating risk of respiratory complications and mortality from the disease. By looking at complications in other organ systems, possible effects on other vascular beds might be evaluated.

Eligible patients: Adults (≥50 years) hospitalized for COVID-19 and having a SARS-CoV-2 infection positive (confirmed by PCR) of Grade 5 (hospitalized; oxygen by mask or nasal prongs) or Grade 6 (hospitalized; oxygen by non-invasive ventilation or high flow) based on the WHO Clinical Progression Scale. (See, WHO Working Group on the Clinical Characterization and Management of COVID-19 infection. A minimal common outcome measure set for COVID-19 clinical research. Lancet Infectious Diseases, Published Online Jun. 12, 2020, doi: 10.1016/S1473-3099(20)30483-7; 2020.)

Treatment and Control Groups: Eligible patients are randomly assigned to a treatment group or control group. In the treatment group, the TRPC6 inhibitor (BI 764198) is orally administered once daily to patients in a capsule or, if needed, via nasogastric intubation after dissolution of the capsule in water. In the control group, a placebo is administered once daily to patients as a capsule matching the TRPC6 inhibitor or, only if needed, via nasogastric intubation after dissolution of the capsule in water. The patients in both groups are hospitalized during the treatment period (maximum treatment of 28 days).

Treatment regimen: The study drug and placebo are administered after at least 6 hours fasting (no food, water allowed). Patients should remain fasted for 1.5 hours after study drug or placebo administration. The nutritional status is a recommendation and not a strict requirement.

Results: The primary trial objective is to estimate the treatment effect between BI 764198 and placebo. For example, patients will be monitored for clinical improvement, oxygen saturation and percentage of patients admitted to the intensive care unit. The primary comparison will be made as randomized, without regard to any treatment changes.

Primary endpoint: Patients alive and free of mechanical ventilation at Day 29.

Secondary endpoints: Improvements on the WHO Clinical Progression Scale. To be considered a "responder" to treatment with a target candidate, a patient needs to show a response. The endpoint is: time to response, defined as clinical improvement of at least 2 points (from randomisation) on the World Health Organization Clinical Progression Scale, discharge from the hospital, or considered fit for discharge (a score of 0, 1, 2, or 3 on the Clinical Progression Scale), whichever comes first, by Day 29. For example, a case where a patient who is Grade 5 (hospitalized; oxygen by mask or nasal prongs) at randomization but improves to Grade 3 (symptomatic; assistance needed) would be considered a response. A patient with a discharge from hospital or who is considered fit for discharge (a score of 0, 1, or 2 on the Clinical Progression Scale) by Day 29 will also be considered a response.

WHO Clinical Progression Scale:

0. Uninfected; no viral RNA detected
1. Asymptomatic; viral RNA detected
2. Symptomatic; independent
3. Symptomatic; assistance needed
4. Hospitalized; no oxygen therapy
5. Hospitalized; oxygen by mask or nasal prongs
6. Hospitalized; oxygen by non-invasive ventilation or high flow
7. Intubation and mechanical ventilation, pO2/FiO2≥150 or SpO2/FiO2≥200
8. Mechanical ventilation pO2/FiO2<150 (SpO2/FiO2<200) or vasopressors
9. Mechanical ventilation pO2/FiO2<150 and vasopressors, dialysis, or extracorporeal membrane oxygenation (ECMO)
10. Death ECMO=extracorporeal membrane oxygenation. FiO2=fraction of inspired oxygen. NIV=non-invasive ventilation. pO2=partial pressure of oxygen. SpO2=oxygen saturation. *If hospitalised for isolation only, record status as for ambulatory patient Other Endpoints:

Patients alive and discharged free of oxygen at Day 29

Number of ventilator free days by Day 29Mortality at Day 15, 29, 60, and 90

Patients with occurrence of any component of composite: In-hospital mortality or intensive care unit (ICU) admission or mechanical ventilation at Day 29

What is claimed is:

1. A method for treating a disorder associated with vascular hyperpermeability and/or conditions arising therefrom by inhibiting the Transient Receptor Potential C6 ion channel (TRPC6), comprising administering to a patient in need thereof a pharmaceutically effective amount of a TRPC6 inhibitor of formula (I), (I)

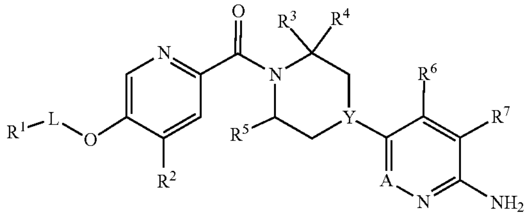

wherein

L is absent or is methylene or ethylene;

Y is CH or N;

A is CH or N;

$R^1$ is selected from the group consisting of:

$C_{1-6}$alkyl optionally substituted with 1 to 3 groups independently selected from the group consisting of halo, $C_{3-6}$cycloalkyl and $OC_{3-6}$cycloalkyl;

phenyl optionally substituted with 1 to 3 groups independently selected from the group consisting of $CF_3$, halo, $C_{3-6}$cycloalkyl, $OC_{3-6}$cycloalkyl, and $OC_{1-6}$alkyl optionally substituted with one to three halo; and $C_{3-6}$cycloalkyl optionally substituted with 1 to 3 groups independently selected from the group consisting of halo and $C_{1-6}$alkyl optionally substituted with 1 to 3 halo;

$R^2$ is selected from the group consisting of H, $C_{1-6}$alkyl, $OCF_3$, $C_{3-6}$cycloalkyl, $OC_{1-6}$alkyl, and $OC_{3-6}$cycloalkyl;

$R^3$ is selected from the group consisting of H, $C_{1-6}$alkyl, $C_{3-6}$cycloalkyl, and $OC_{3-6}$cycloalkyl; wherein each of the $C_{1-6}$alkyl, $C_{3-6}$cycloalkyl, $OC_{3-6}$cycloalkyl of the $R^3$ group may be optionally substituted with one to three groups each independently selected from the group consisting of halo, OH, $OC_{1-6}$alkyl, $SC_{1-6}$alkyl, and $N(C_{1-6}alky)_2$; and wherein one to three carbon atoms of the $C_{1-6}$alkyl of the $R^3$ group may optionally be replaced one or two moieties selected from the group consisting of NH, $N(C_{1-6}alkyl)$, O, and S;

$R^4$ and $R^5$ are each independently selected from the group consisting of H and $C_{1-6}$alkyl;

$R^3$ and $R^4$ can together with the atom to which they are attached join to form a 3 to 9-membered carbocyclyl ring which optionally may contain one to three heteroatoms selected from the group consisting of N, O, and S; or $R^3$ and $R^5$ can together form a 3 to 9-membered bicyclic ring which optionally may contain one to three heteroatoms selected from the group consisting of N, O, and S;

$R^6$ is selected from the group consisting of H, $C_{1-6}$alkyl, CN, $CF_3$, $OCF_3$, $C_{3-6}$cycloalkyl, $OC_{1-6}$alkyl, and $OC_{3-6}$cycloalkyl;

$R^7$ is selected from the group consisting of H and $OC_{1-6}$alkyl;

or a pharmaceutically acceptable salt thereof, wherein the disorder associated with vascular hyperpermeability and/or conditions arising therefrom is selected from the group consisting of sepsis, severe sepsis, and septic shock.

2. The method of claim 1, wherein $R^1$ is selected from the group consisting of:

$C_{1-6}$alkyl optionally substituted with 1 to 3 groups independently selected from the group consisting of halo, and $C_{3-6}$cycloalkyl;

phenyl optionally substituted with 1 to 3 groups independently selected from the group consisting of $CF_3$, halo, $OC_{3-6}$cycloalkyl, and $OC_{1-6}$alkyl optionally substituted with one to three halo; and $C_{3-6}$cycloalkyl optionally substituted with 1 to 3 halo groups;

$R^2$ is $OC_{1-6}$alkyl;

$R^3$ is selected from the group consisting of H and $C_{1-6}$alkyl optionally substituted with OH or $OC_{1-6}$alkyl, $R^4$ is H;

$R^5$ is H;

$R^3$ and $R^4$ can together with the atom to which they are attached join to form a 3 to 9-membered carbocyclyl ring which optionally may contain one to three heteroatoms selected from the group consisting of N and O; or $R^3$ and $R^5$ can together form a 3 to 9-membered bicyclic which optionally may contain one to three heteroatoms selected from the group consisting of N and O;

$R^6$ is selected from the group consisting of H, $C_{1-6}$alkyl, $OC_{1-6}$alkyl, and $OC_{3-6}$cycloalkyl, $R^7$ is selected from the group consisting of H and $OC_{1-6}$alkyl;

or a pharmaceutically acceptable salt thereof.

3. The method of claim 1, wherein the TRPC6 inhibitor is selected from the group consisting of:

| Cpd No. | Structure | Compound Name |
|---|---|---|
| 1 | 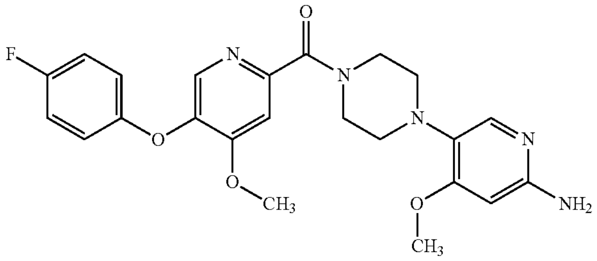 [SMILES: COc1cc(C(=O)N2CCN(c3cnc(N)cc3OC)CC2)ncc1Oc1ccc(F)cc1] | [4-(6-Amino-4-methoxy-pyridin-3-yl)-piperazin-1-yl]-[5-(4-fluoro-phenoxy)-4-methoxy-pyridin-2-yl]-methanone |
| 2 | 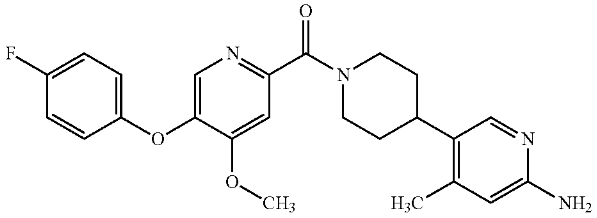 [SMILES: COc1cc(C(=O)N2CCC(c3cnc(N)cc3C)CC2)ncc1Oc1ccc(F)cc1] | (6-Amino-4-methyl-3',4',5',6'-tetrahydro-2'H-[3,4']bipyridinyl-1'-yl)-[5-(4-fluoro-phenoxy)-4-methoxy-pyridin-2-yl]-methanone |
| 3 | 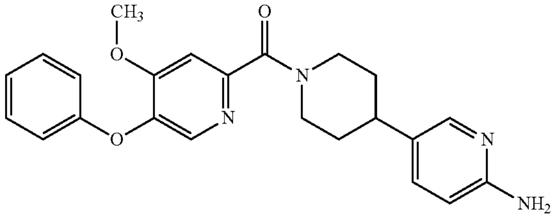 | (6-Amino-3',4',5',6'-tetrahydro-2'H-[3,4']bipyridinyl-1'-yl)-(4-methoxy-5-phenoxy-pyridin-2-yl)-methanone |
| 4 | 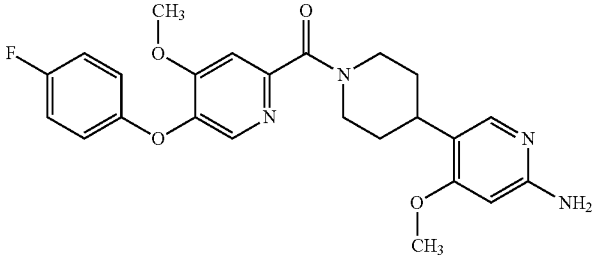 [SMILES: COc1cc(C(=O)N2CCC(c3cnc(N)cc3OC)CC2)ncc1Oc1ccc(F)cc1] | (6-Amino-4-methoxy-3',4',5',6'-tetrahydro-2'H-[3,4']bipyridinyl-1'-yl)-[5-(4-fluoro-phenoxy)-4-methoxy-pyridin-2-yl]-methanone |
| 5 | 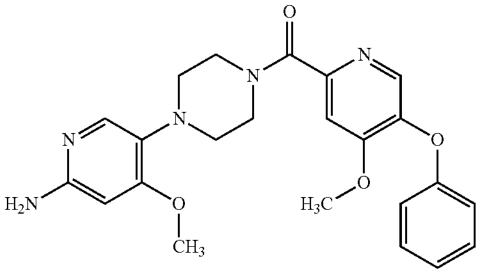 [SMILES: COc1cc(C(=O)N2CCN(c3cnc(N)cc3OC)CC2)ncc1Oc1ccccc1] | [4-(6-Amino-4-methoxy-pyridin-3-yl)-piperazin-1-yl]-(4-methoxy-5-phenoxy-pyridin-2-yl)-methanone |

-continued

| Cpd No. | Structure | Compound Name |
|---|---|---|
| 6 | 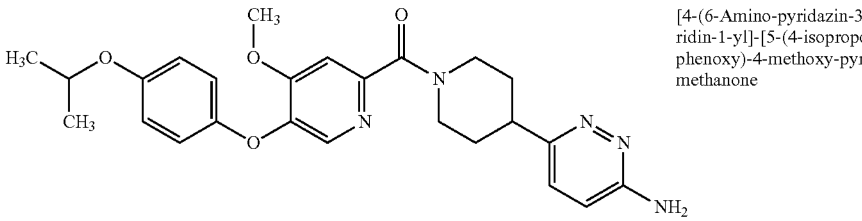 | [4-(6-Amino-pyridazin-3-yl)-piperidin-1-yl]-[5-(4-isopropoxy-phenoxy)-4-methoxy-pyridin-2-yl]-methanone |
| 7 | 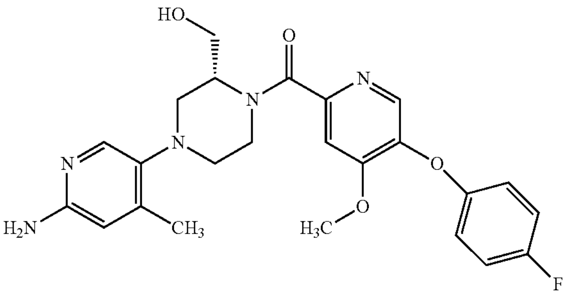 [SMILES: COc1cc(C(=O)N2CCN(c3cnc(N)cc3C)C[C@@H]2CO)ncc1Oc1ccc(F)cc1] | [(R)-4-(6-Amino-4-methyl-pyridin-3-yl)-2-hydroxymethyl-piperazin-1-yl]-[5-(4-fluoro-phenoxy)-4-methoxy-pyridin-2-yl]-methanone |
| 8 | 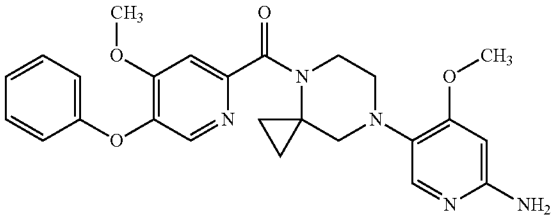 [SMILES: COc1cc(C(=O)N2CCN(c3cnc(N)cc3OC)CC23CC3)ncc1Oc1ccccc1] | [7-(6-Amino-4-methoxy-pyridin-3-yl)-4,7-diaza-spiro[2.5]oct-4-yl]-(4-methoxy-5-phenoxy-pyridin-2-yl)-methanone |
| 9 | 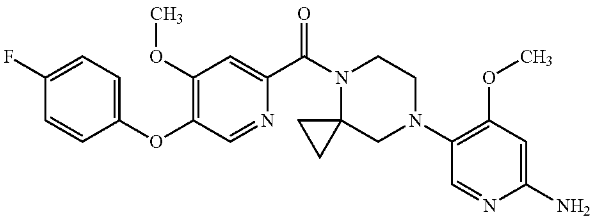 [SMILES: COc1cc(C(=O)N2CCN(c3cnc(N)cc3OC)CC23CC3)ncc1Oc1ccc(F)cc1] | [7-(6-Amino-4-methoxy-pyridin-3-yl)-4,7-diaza-spiro[2.5]oct-4-yl]-[5-(4-fluoro-phenoxy)-4-methoxy-pyridin-2-yl]-methanone |
| 10 | 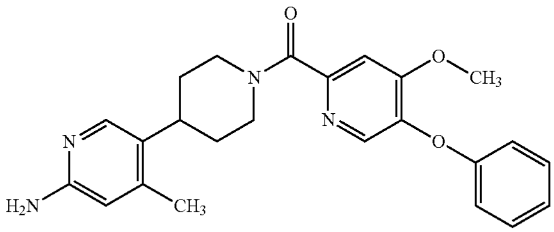 [SMILES: COc1cc(C(=O)N2CCC(c3cnc(N)cc3C)CC2)ncc1Oc1ccccc1] | (6-Amino-4-methyl-3',4',5',6'-tetrahydro-2'H-[3,4']bipyridinyl-r-yl)-(4-methoxy-5-phenoxy-pyridin-2-yl)-methanone |
| 11 | 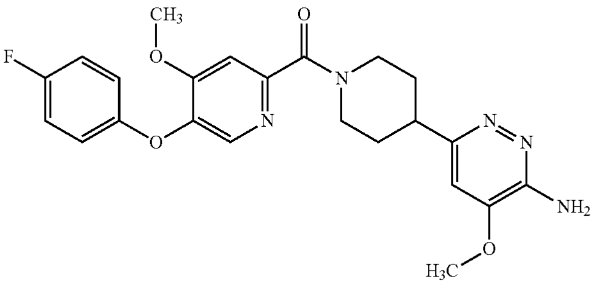 [SMILES: COc1cc(C(=O)N2CCC(c3cc(OC)c(N)nn3)CC2)ncc1Oc1ccc(F)cc1] | [4-(6-Amino-5-methoxy-pyridazin-3-yl)-piperidin-1-yl]-[5-(4-fluoro-phenoxy)-4-methoxy-pyridin-2-yl]-methanone |

-continued

| Cpd No. | Structure | Compound Name |
| --- | --- | --- |
| 12 | 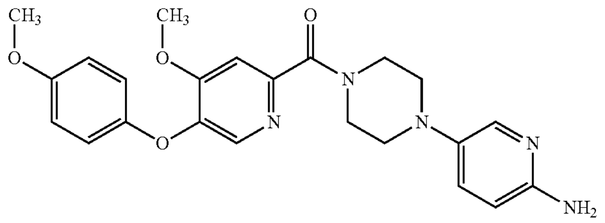 | [4-(6-Amino-pyridin-3-yl)-piperazin-1-yl]-[4-methoxy-5-(4-methoxy-phenoxy)-pyridin-2-yl]-methanone |
| 13 | 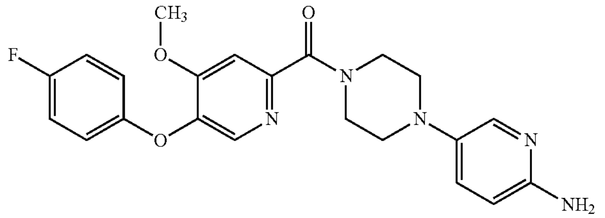 | [4-(6-Amino-pyridin-3-yl)-piperazin-1-yl]-[5-(4-fluoro-phenoxy)-4-methoxy-pyridin-2-yl]-methanone |
| 14 | 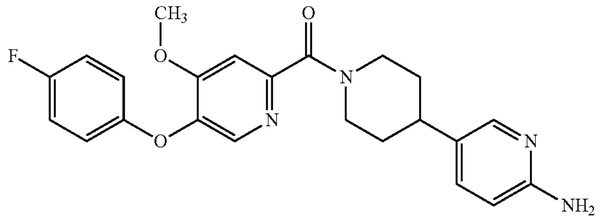 [SMILES: COc1cc(C(=O)N2CCC(c3ccc(N)nc3)CC2)ncc1Oc1ccc(F)cc1] | (6-Amino-3',4',5',6'-tetrahydro-2'H-[3,4']bipyridinyl-1'-yl)-[5-(4-fluoro-phenoxy)-4-methoxy-pyridin-2-yl]-methanone |
| 15 | 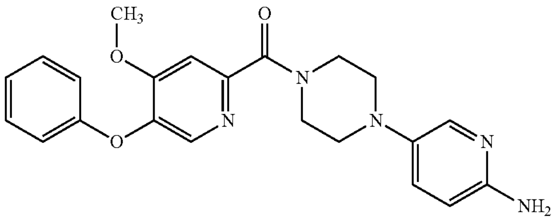 [SMILES: COc1cc(C(=O)N2CCN(c3ccc(N)nc3)CC2)ncc1Oc1ccccc1] | [4-(6-Amino-pyridin-3-yl)-piperazin-1-yl]-(4-methoxy-5-phenoxy-pyridin-2-yl)-methanone |
| 16 | 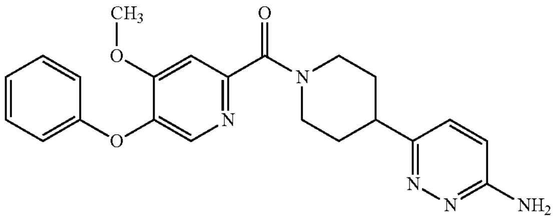 [SMILES: COc1cc(C(=O)N2CCC(c3ccc(N)nn3)CC2)ncc1Oc1ccccc1] | [4-(6-Amino-pyridazin-3-yl)-piperidin-1-yl]-(4-methoxy-5-phenoxy-pyridin-2-yl)-methanone |
| 17 | 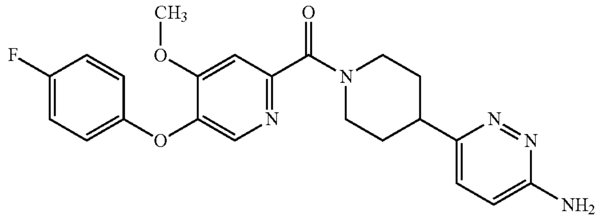 [SMILES: COc1cc(C(=O)N2CCC(c3ccc(N)nn3)CC2)ncc1Oc1ccc(F)cc1] | [4-(6-Amino-pyridazin-3-yl)-piperidin-1-yl]-[5-(4-fluoro-phenoxy)-4-methoxy-pyridin-2-yl]-methanone |

-continued

| Cpd No. | Structure | Compound Name |
| --- | --- | --- |
| 18 | 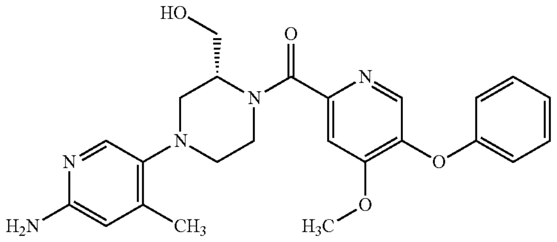 [SMILES: COc1cc(C(=O)N2CCN(c3cnc(N)cc3C)C[C@@H]2CO)ncc1Oc1ccccc1] | [(R)-4-(6-Amino-4-methyl-pyridin-3-yl)-2-hydroxymethyl-piperazin-1-yl]-(4-methoxy-5-phenoxy-pyridin-2-yl)-methanone |
| 19 | 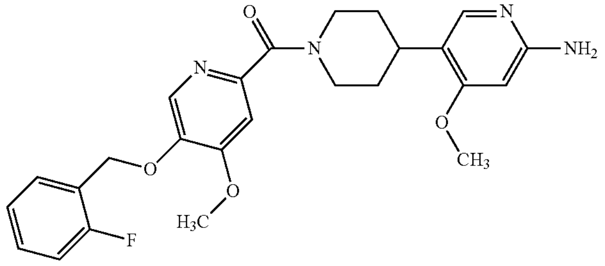 [SMILES: COc1cc(C(=O)N2CCC(c3cnc(N)cc3OC)CC2)ncc1OCc1ccccc1F] | (6-Amino-4-methoxy-3',4',5',6'-tetrahydro-2'H-[3,4']bipyridinyl-1'-yl)-[5-(2-fluoro-benzyloxy)-4-methoxy-pyridin-2-yl]-methanone |
| 20 | 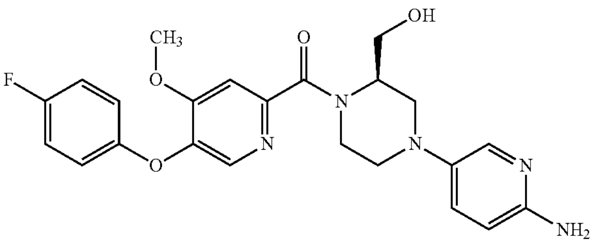 [SMILES: COc1cc(C(=O)N2CCN(c3ccc(N)nc3)C[C@@H]2CO)ncc1Oc1ccc(F)cc1] | [(R)-4-(6-Amino-pyridin-3-yl)-2-hydroxymethyl-piperazin-1-yl]-[5-(4-fluoro-phenoxy)-4-methoxy-pyridin-2-yl]-methanone |
| 21 | 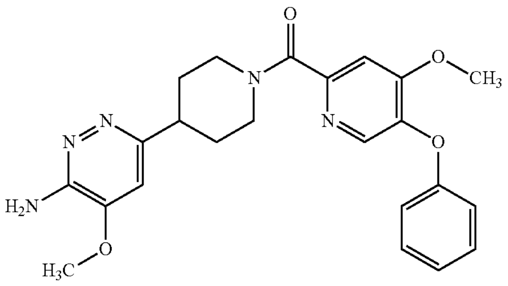 [SMILES: COc1cc(C(=O)N2CCC(c3cc(OC)c(N)nn3)CC2)ncc1Oc1ccccc1] | [4-(6-Amino-5-methoxy-pyridazin-3-yl)-piperidin-1-yl]-(4-methoxy-5-phenoxy-pyridin-2-yl)-methanone |
| 22 | 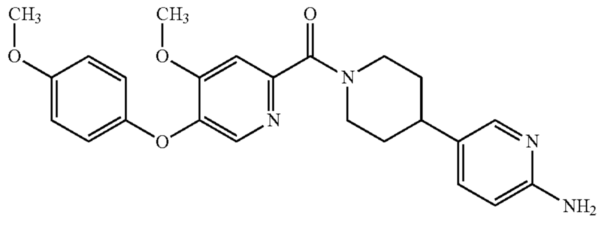 [SMILES: COc1ccc(Oc2cnc(C(=O)N3CCC(c4ccc(N)nc4)CC3)cc2OC)cc1] | (6-Amino-3',4',5',6'-tetrahydro-2'H-[3,4']bipyridinyl-1'-yl)-[4-methoxy-5-(4-methoxy-phenoxy)-pyridin-2-yl]-methanone |
| 23 | 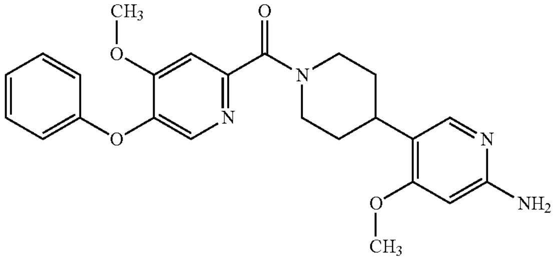 [SMILES: COc1cc(C(=O)N2CCC(c3cnc(N)cc3OC)CC2)ncc1Oc1ccccc1] | (6-Amino-4-methoxy-3',4',5',6'-tetrahydro-2'H-[3,4']bipyridinyl-1'-yl)-(4-methoxy-5-phenoxy-pyridin-2-yl)-methanone |

-continued

| Cpd No. | Structure | Compound Name |
|---|---|---|
| 24 | 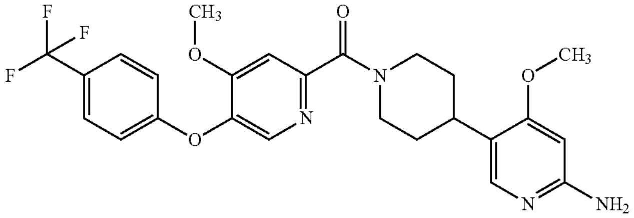 | (6-Amino-4-methoxy-3',4',5',6'-tetrahydro-2'H-[3,4']bipyridinyl-1'-yl)-[4-methoxy-5-(4-trifluoromethyl-phenoxy)-pyridin-2-yl]-methanone |
| 25 | 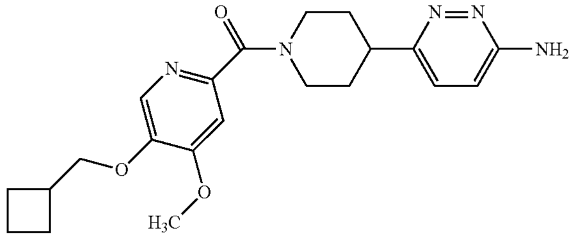 [SMILES: COc1cc(C(=O)N2CCC(c3ccc(N)nn3)CC2)ncc1OCC1CCC1] | [4-(6-Amino-pyridazin-3-yl)-piperidin-1-yl]-(5-cyclobutylmethoxy-4-methoxy-pyridin-2-yl)-methanone |
| 26 | 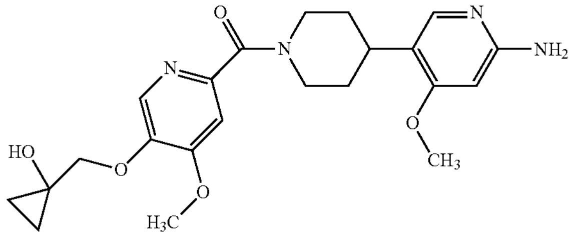 [SMILES: COc1cc(C(=O)N2CCC(c3cnc(N)cc3OC)CC2)ncc1OCC1(O)CC1] | (6-Amino-4-methoxy-3',4,5',6'-tetrahydro-2'H-[3,4']bipyridinyl-1'-yl)-[4-methoxy-5-(1-methyl-cyclopropylmethoxy)-pyridin-2-yl]-methanone |
| 27 | 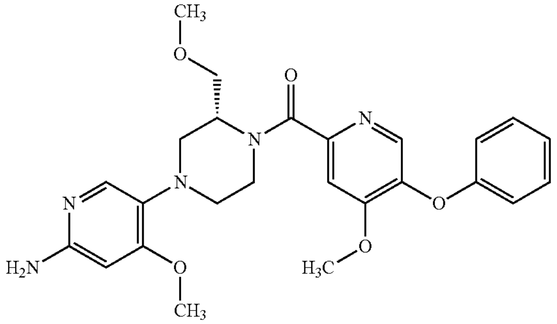 [SMILES: COC[C@H]1CN(c2cnc(N)cc2OC)CCN1C(=O)c1cc(OC)c(Oc2ccccc2)cn1] | [(R)-4-(6-Amino-4-methoxy-pyridin-3-yl)-2-methoxymethyl-piperazin-1-yl]-(4-methoxy-5-phenoxy-pyridin-2-yl)-methanone |
| 28 | 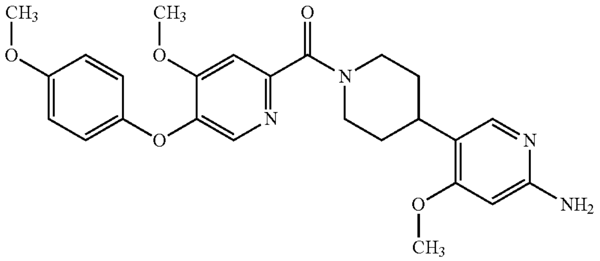 | (6-Amino-4-methoxy-3',4',5',6'-tetrahydro-2'H-[3,4']bipyridinyl-1'-yl)-[4-methoxy-5-(4-methoxy-phenoxy)-pyridin-2-yl]-methanone |
| 29 | 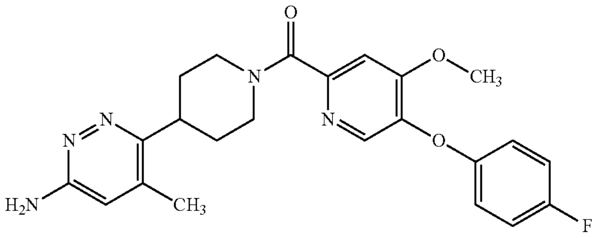 [SMILES: COc1cc(C(=O)N2CCC(c3nnc(N)cc3C)CC2)ncc1Oc1ccc(F)cc1] | [4-(6-Amino-4-methyl-pyridazin-3-yl)-piperidin-1-yl]-[5-(4-fluoro-phenoxy)-4-methoxy-pyridin-2-yl]-methanone |

-continued

| Cpd No. | Structure | Compound Name |
| --- | --- | --- |
| 30 | 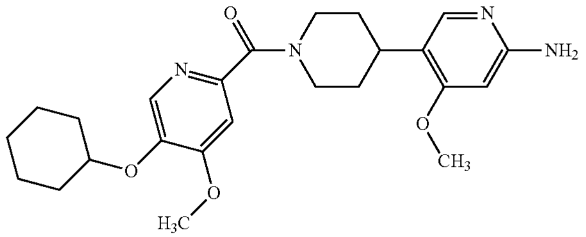 [SMILES: COc1cc(C(=O)N2CCC(c3cnc(N)cc3OC)CC2)ncc1OC1CCCCC1] | (6-Amino-4-methoxy-3',4',5',6'-tetrahydro-2'H-[3,4']bipyridinyl-1'-yl)-(5-cyclohexyloxy-4-methoxy-pyridin-2-yl)-methanone |
| 31 | 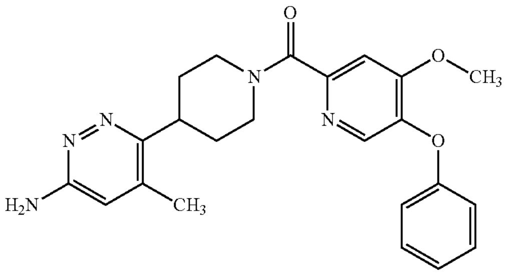 [SMILES: COc1cc(C(=O)N2CCC(c3nnc(N)cc3C)CC2)ncc1Oc1ccccc1] | [4-(6-Amino-4-methyl-pyridazin-3-yl)-piperidin-1-yl]-(4-methoxy-5-phenoxy-pyridin-2-yl)-methanone |
| 32 | 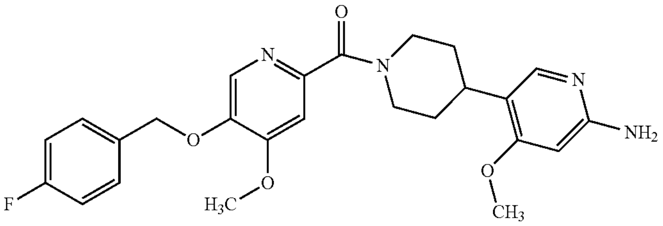 [SMILES: COc1cc(C(=O)N2CCC(c3cnc(N)cc3OC)CC2)ncc1OCc1ccc(F)cc1] | (6-Amino-4-methoxy-3',4',5',6'-tetrahydro-2'H-[3,4']bipyridinyl-1'-yl)-[5-(4-fluoro-benzyloxy)-4-methoxy-pyridin-2-yl]-methanone |
| 33 | 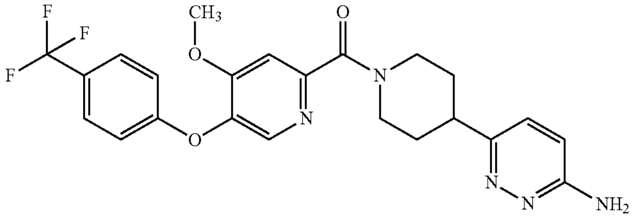 [SMILES: COc1cc(C(=O)N2CCC(c3ccc(N)nn3)CC2)ncc1Oc1ccc(C(F)(F)F)cc1] | [4-(6-Amino-pyridazin-3-yl)-piperidin-1-yl]-[4-methoxy-5-(4-trifluoromethyl-phenoxy)-pyridin-2-yl]-methanone |
| 34 | 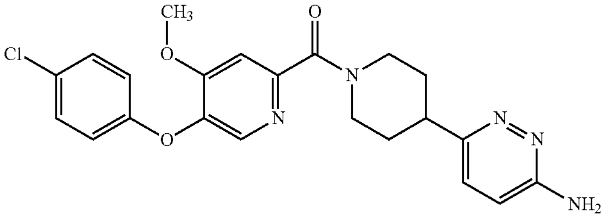 [SMILES: COc1cc(C(=O)N2CCC(c3ccc(N)nn3)CC2)ncc1Oc1ccc(Cl)cc1] | [4-(6-Amino-pyridazin-3-yl)-piperidin-1-yl]-[5-(4-chloro-phenoxy)-4-methoxy-pyridin-2-yl]-methanone |
| 35 | 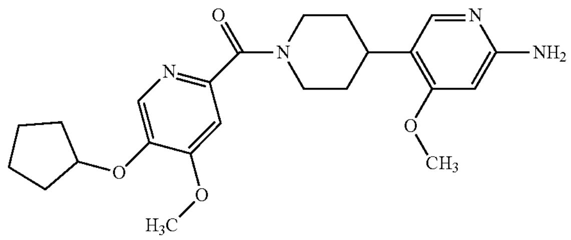 [SMILES: COc1cc(C(=O)N2CCC(c3cnc(N)cc3OC)CC2)ncc1OC1CCCC1] | (6-Amino-4-methoxy-3',4',5',6'-tetrahydro-2'H-[3,4']bipyridinyl-1'-yl)-(5-cyclopentyloxy-4-methoxy-pyridin-2-yl)-methanone |

-continued

| Cpd No. | Structure | Compound Name |
| --- | --- | --- |
| 36 | 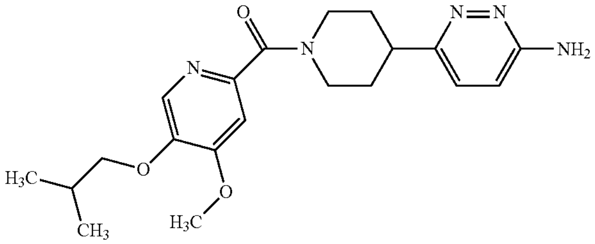 [SMILES: COc1cc(C(=O)N2CCC(c3ccc(N)nn3)CC2)ncc1OCC(C)C] | [4-(6-Amino-pyridazin-3-yl)-piperi-din-1-yl]-(5-isobutoxy-4-methoxy-pyridin-2-yl)-methanone |
| 37 | 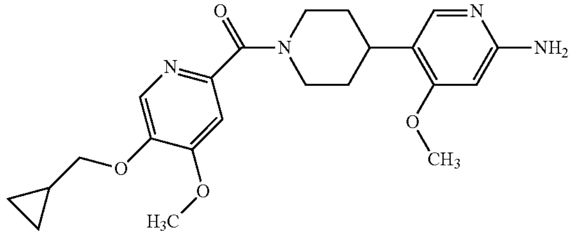 | (6-Amino-4-methoxy-3',4',5',6'-te-trahydro-2'H-[3,4']bipyridinyl-1'-yl)-(5-cyclopropylmethoxy-4-methoxy-pyridin-2-yl)-methanone |
| 38 | 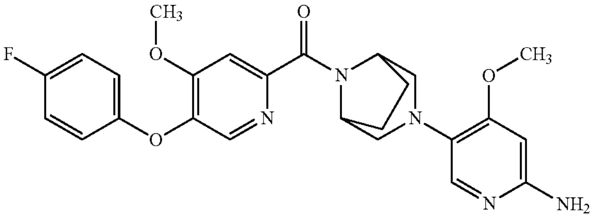 [SMILES: COc1cc(C(=O)N2C3CCC2CN(c2cnc(N)cc2OC)C3)ncc1Oc1ccc(F)cc1] | [3-(6-Amino-4-methoxy-pyridin-3-yl)-3,8-diaza-bicyclo[3.2.1]oct-8-yl]-[5-(4-fluoro-phenoxy)-4-methoxy-pyridin-2-yl]-methanone |
| 39 | 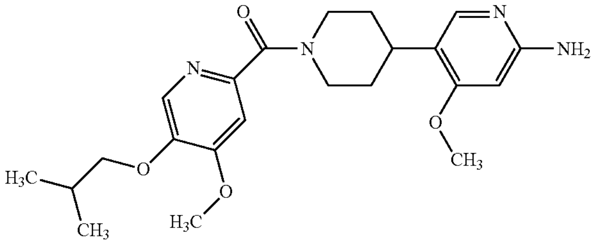 [SMILES: COc1cc(C(=O)N2CCC(c3cnc(N)cc3OC)CC2)ncc1OCC(C)C] | (6-Amino-4-methoxy-3',4',5',6'-te-trahydro-2'H-[3,4']bipyridinyl-1'-yl)-(5-isobutoxy-4-methoxy-pyridin-2-yl)-methanone |
| 40 | 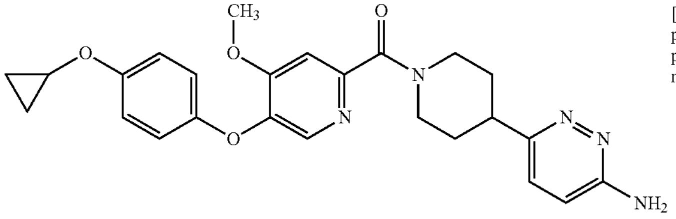 | [4-(6-Amino-pyridazin-3-yl)-piperidin-1-yl]-[5-(4-cyclopropoxy-phenoxy)-4-methoxy-pyridin-2-yl]-methanone |
| 41 | 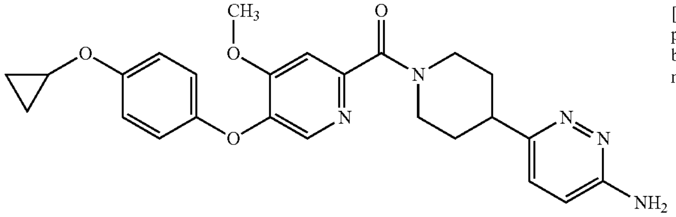 | [4-(6-Amino-pyridazin-3-yl)-piperidin-1-yl]-[5-(4-fluoro-benzyloxy)-4-methoxy-pyridin-2-yl]-methanone |

-continued

| Cpd No. | Structure | Compound Name |
|---|---|---|
| 42 | 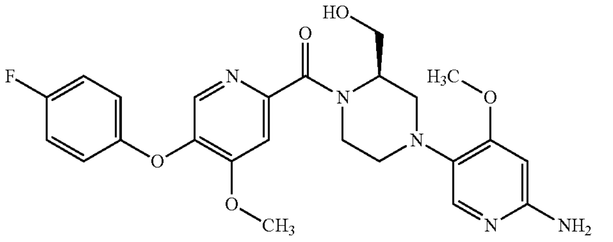 [SMILES: COc1cc(C(=O)N2CCN(c3cnc(N)cc3OC)C[C@@H]2CO)ncc1Oc1ccc(F)cc1] | [(R)-4-(6-Amino-4-methoxy-pyridin-3-yl)-2-hydroxymethyl-piperazin-1-yl]-[5-(4-fluoro-phenoxy)-4-methoxy-pyridin-2-yl]-methanone |
| 43 | 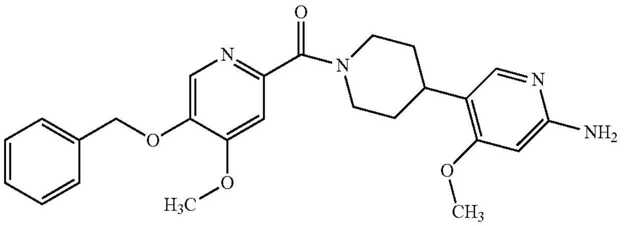 [SMILES: COc1cc(C(=O)N2CCC(c3cnc(N)cc3OC)CC2)ncc1OCc1ccccc1] | (6-Amino-4-methoxy-3',4',5',6'-tetrahydro-2'H-[3,4']bipyridinyl-1'-yl)-(5-benzyloxy-4-methoxy-pyridin-2-yl)-methanone |
| 44 | 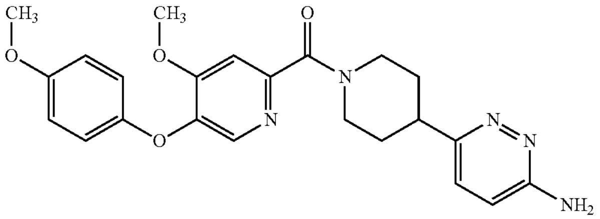 [SMILES: COc1ccc(Oc2cnc(C(=O)N3CCC(c4ccc(N)nn4)CC3)cc2OC)cc1] | [4-(6-Amino-pyridazin-3-yl)-piperidin-1-yl]-[4-methoxy-5-(4-methoxy-phenoxy)-pyridin-2-yl]-methanone |
| 45 | 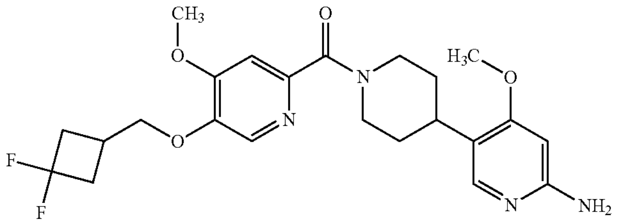 [SMILES: COc1cc(C(=O)N2CCC(c3cnc(N)cc3OC)CC2)ncc1OCC1CC(F)(F)C1] | (6-Amino-4-methoxy-3',4',5',6'-tetrahydro-2'H-[3,4']bipyridinyl-1'-yl)-[5-(3,3-difluoro-cyclobutylmethoxy)-4-methoxy-pyridin-2-yl]-methanone |
| 46 | 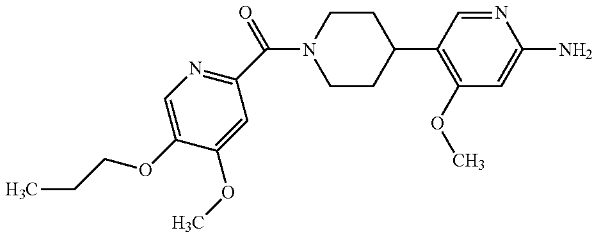 [SMILES: CCCOc1cnc(C(=O)N2CCC(c3cnc(N)cc3OC)CC2)cc1OC] | (6-Amino-4-methoxy-3',4',5',6'-tetrahydro-2'H-[3,4']bipyridinyl-1'-yl)-(4-methoxy-5-propoxy-pyridin-2-yl)-methanone |
| 47 | 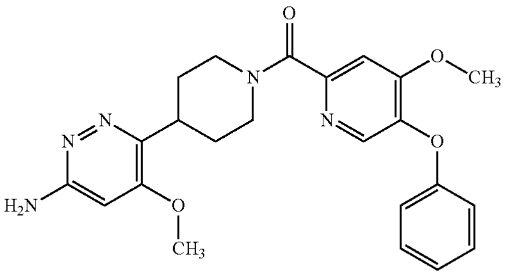 [SMILES: COc1cc(C(=O)N2CCC(c3nnc(N)cc3OC)CC2)ncc1Oc1ccccc1] | [4-(6-Amino-4-methoxy-pyridazin-3-yl)-piperidin-1-yl]-(4-methoxy-5-phenoxy-pyridin-2-yl)-methanone |

-continued

| Cpd No. | Structure | Compound Name |
|---|---|---|
| 48 | 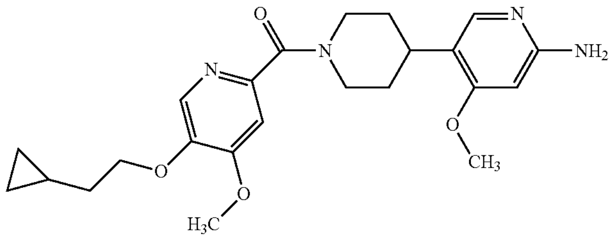 [SMILES: COc1cc(C(=O)N2CCC(c3cnc(N)cc3OC)CC2)ncc1OCCC1CC1] | (6-Amino-4-methoxy-3',4',5',6'-tetrahydro-2'H-[3,4']bipyridinyl-1'-yl)-[5-(2-cyclopropyl-ethoxy)-4-methoxy-pyridin-2-yl]-methanone |
| 49 | 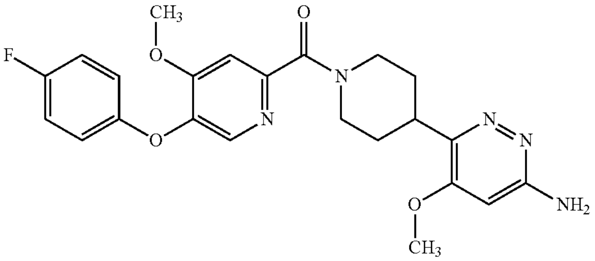 [SMILES: COc1cc(C(=O)N2CCC(c3nnc(N)cc3OC)CC2)ncc1Oc1ccc(F)cc1] | [4-(6-Amino-4-methoxy-pyridazin-3-yl)-piperidin-1-yl]-[5-(4-fluoro-phenoxy)-4-methoxy-pyridin-2-yl]-methanone |
| 50 | 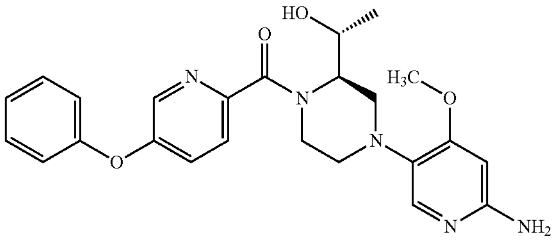 [SMILES: COc1cc(N)ncc1N1CCN(C(=O)c2ccc(Oc3ccccc3)cn2)[C@@H]([C@@H](C)O)C1] | (1R)-1-[(2R)-4-(6-amino-4-methoxy-pyridin-3-yl)-1-(5-phenoxypyridine-2-carbonyl)piperazin-2-yl]ethan-1-ol |
| 51 | 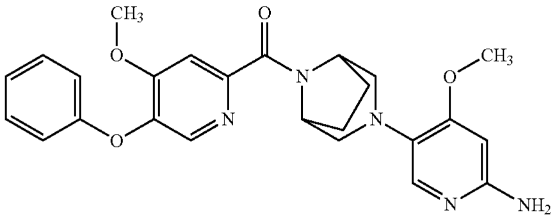 [SMILES: COc1cc(C(=O)N2C3CCC2CN(c2cnc(N)cc2OC)C3)ncc1Oc1ccccc1] | [3-(6-Amino-4-methoxy-pyridin-3-yl)-3,8-diaza-bicyclo[3.2.1]oct-8-yl]-(4-methoxy-5-phenoxy-pyridin-2-yl)-methanone |
| 52 | 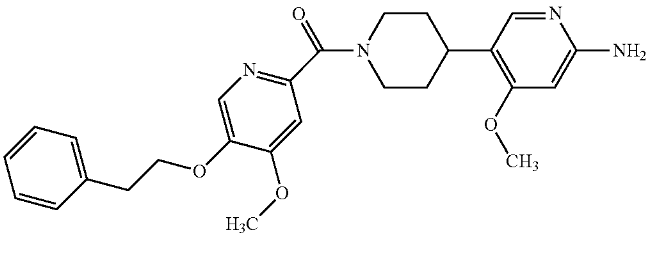 [SMILES: COc1cc(C(=O)N2CCC(c3cnc(N)cc3OC)CC2)ncc1OCCc1ccccc1] | (6-Amino-4-methoxy-3',4',5',6'-tetrahydro-2'H-[3,4']bipyridinyl-1'-yl)-(4-methoxy-5-phenethyloxy-pyridin-2-yl)-methanone |
| 53 | 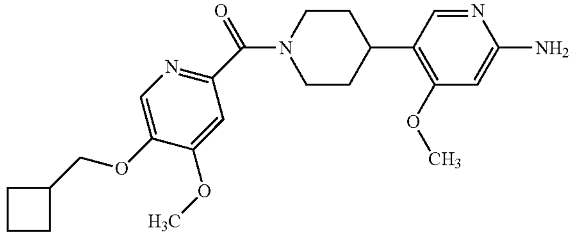 [SMILES: COc1cc(C(=O)N2CCC(c3cnc(N)cc3OC)CC2)ncc1OCC1CCC1] | (6-Amino-4-methoxy-3',4',5',6'-tetrahydro-2'H-[3,4']bipyridinyl-1'-yl)-(5-cyclobutylmethoxy-4-methoxy-pyridin-2-yl)-methanone |

-continued

| Cpd No. | Structure | Compound Name |
| --- | --- | --- |
| 54 | 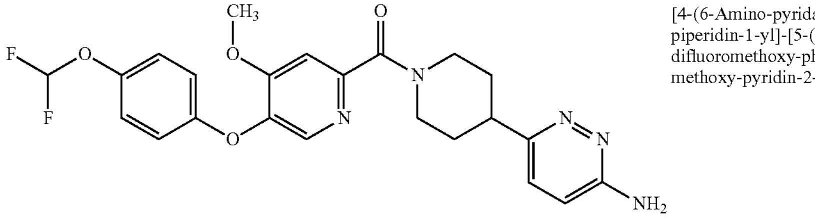 | [4-(6-Amino-pyridazin-3-yl)-piperidin-1-yl]-[5-(4-difluoromethoxy-phenoxy)-4-methoxy-pyridin-2-yl]-methanone |
| 55 | 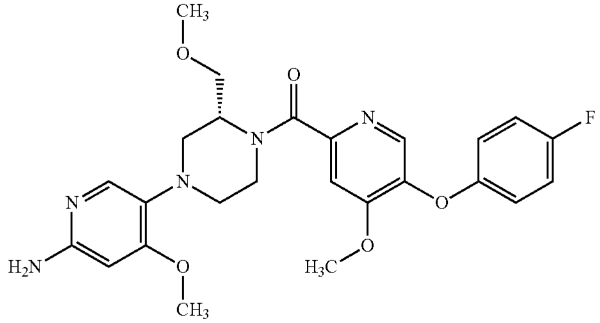 [SMILES: COC[C@H]1CN(c2cnc(N)cc2OC)CCN1C(=O)c1cc(OC)c(Oc2ccc(F)cc2)cn1] | [(R)-4-(6-Amino-4-methoxy-pyridin-3-yl)-2-methoxymethyl-piperazin-1-yl]-[5-(4-fluoro-phenoxy)-4-methoxy-pyridin-2-yl]-methanone |
| 56 | 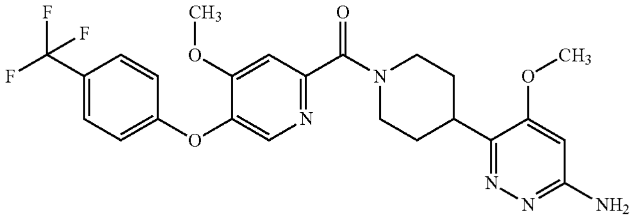 [SMILES: COc1cc(C(=O)N2CCC(c3nnc(N)cc3OC)CC2)ncc1Oc1ccc(C(F)(F)F)cc1] | [4-(6-Amino-4-methoxy-pyridazin-3-yl)-piperidin-1-yl]-[4-methoxy-5-(4-trifluoromethyl-phenoxy)-pyridin-2-yl]-methanone |
| 57 | 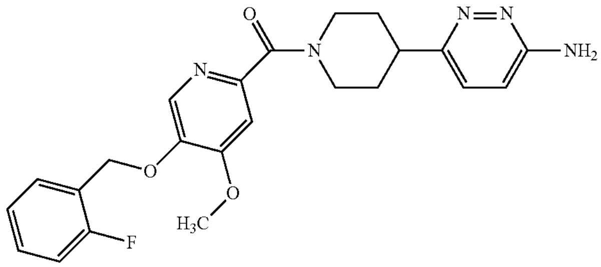 [SMILES: COc1cc(C(=O)N2CCC(c3ccc(N)nn3)CC2)ncc1OCc1ccccc1F] | [4-(6-Amino-pyridazin-3-yl)-piperidin-1-yl]-[5-(2-fluoro-benzyloxy)-4-methoxy-pyridin-2-yl]-methanone |
| 58 | 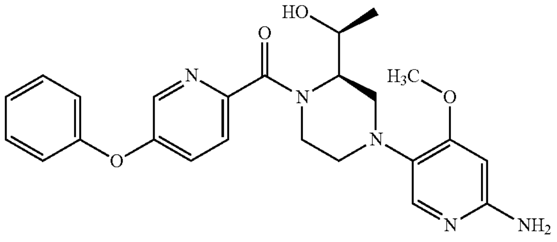 [SMILES: COc1cc(N)ncc1N1CCN(C(=O)c2ccc(Oc3ccccc3)cn2)[C@@H]([C@H](C)O)C1] | (1S)-1-[(2R)-4-(6-amino-4-methoxy-pyridin-3-yl)-1-(5-phenoxypyridine-2-carbonyl)piperazin-2-yl]ethan-1-ol |
| 59 | 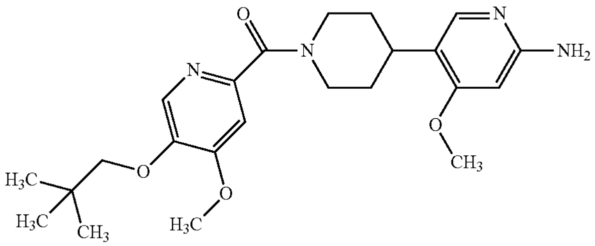 [SMILES: COc1cc(C(=O)N2CCC(c3cnc(N)cc3OC)CC2)ncc1OCC(C)(C)C] | (6-Amino-4-methoxy-3',4',5',6'-tetrahydro-2'H-[3,4']bipyridinyl-1'-yl)-[5-(2,2-dimethyl-propoxy)-4-methoxy-pyridin-2-yl]-methanone |

-continued

| Cpd No. | Structure | Compound Name |
| --- | --- | --- |
| 60 | 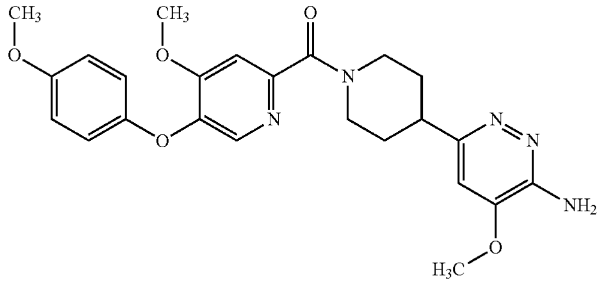 [SMILES: COc1ccc(Oc2cnc(C(=O)N3CCC(c4cc(OC)c(N)nn4)CC3)cc2OC)cc1] | [4-(6-Amino-5-methoxy-pyridazin-3-yl)-piperidin-1-yl]-[4-methoxy-5-(4-methoxy-phenoxy)-pyridin-2-yl]-methanone |
| 61 | 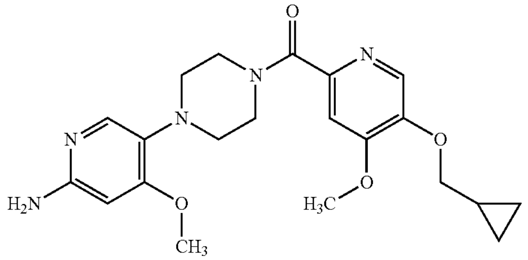 [SMILES: COc1cc(C(=O)N2CCN(c3cnc(N)cc3OC)CC2)ncc1OCC1CC1] | [4-(6-Amino-4-methoxy-pyridin-3-yl)-piperazin-1-yl]-(5-cyclopropyl-methoxy-4-methoxy-pyridin-2-yl)-methanone |
| 62 | 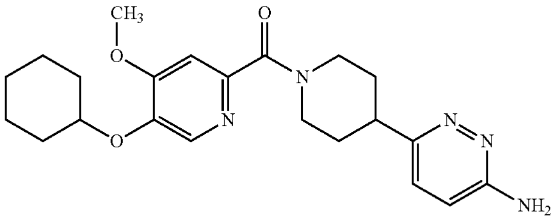 [SMILES: COc1cc(C(=O)N2CCC(c3ccc(N)nn3)CC2)ncc1OC1CCCCC1] | [4-(6-Amino-pyridazin-3-yl)-piperidin-1-yl]-(5-cyclohexyloxy-4-methoxy-pyridin-2-yl)-methanone |
| 63 | 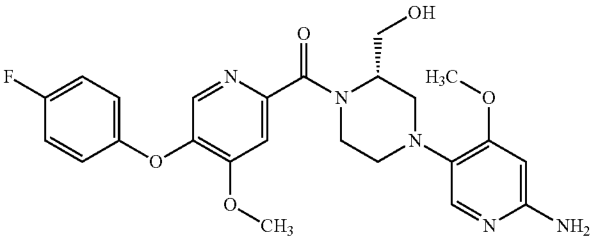 [SMILES: COc1cc(C(=O)N2CCN(c3cnc(N)cc3OC)C[C@H]2CO)ncc1Oc1ccc(F)cc1] | [(S)-4-(6-Amino-4-methoxy-pyridin-3-yl)-2-hydroxymethyl-piperazin-1-yl]-[5-(4-fluoro-phenoxy)-4-methoxy-pyridin-2-yl]-methanone |
| 64 | 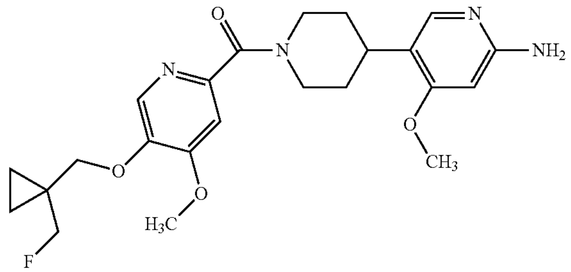 [SMILES: COc1cc(C(=O)N2CCC(c3cnc(N)cc3OC)CC2)ncc1OCC1(CF)CC1] | (6-Amino-4-methoxy-3',4',5',6'-tetrahydro-2'H-[3,4']bipyridinyl-1'-yl)-[5-(1-fluoromethyl-cyclopropyl-methoxy)-4-methoxy-pyridin-2-yl]-methanone |
| 65 | 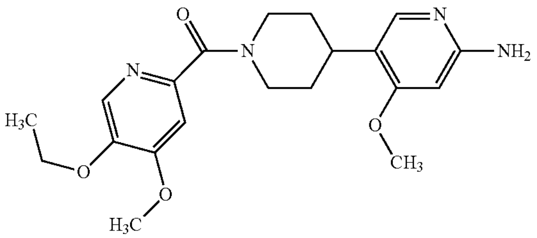 [SMILES: CCOc1cnc(C(=O)N2CCC(c3cnc(N)cc3OC)CC2)cc1OC] | (6-Amino-4-methoxy-3',4',5',6'-tetrahydro-2'H-[3,4']bipyridinyl-1'-yl)-(5-ethoxy-4-methoxy-pyridin-2-yl)-methanone |

-continued

| Cpd No. | Structure | Compound Name |
| --- | --- | --- |
| 66 | 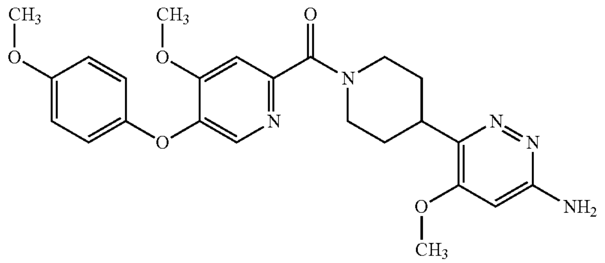 [SMILES: COc1ccc(Oc2cnc(C(=O)N3CCC(c4nnc(N)cc4OC)CC3)cc2OC)cc1] | [4-(6-Amino-4-methoxy-pyridazin-3-yl)-piperidin-1-yl]-[4-methoxy-5-(4-methoxy-phenoxy)-pyridin-2-yl]-methanone |
| 67 | 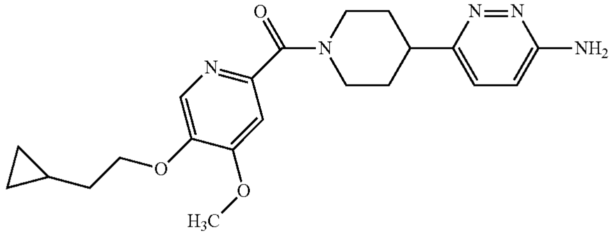 | [4-(6-Amino-pyridazin-3-yl)-piperidin-1-yl]-[5-(2-cyclopropyl-ethoxy)-4-methoxy-pyridin-2-yl]-methanone |
| 68 | 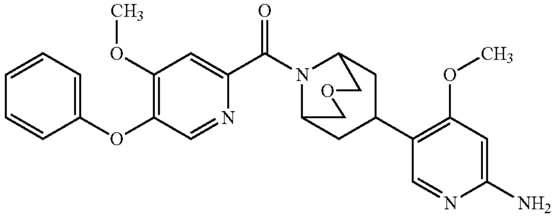 [SMILES: COc1cc(C(=O)N2C3COCC2CC(c2cnc(N)cc2OC)C3)ncc1Oc1ccccc1] | [7-(6-Amino-4-methoxy-pyridin-3-yl)-3-oxa-9-aza-bicyclo[3.3.1]non-9-yl]-(4-methoxy-5-phenoxy-pyridin-2-yl)-methanone |
| 69 | 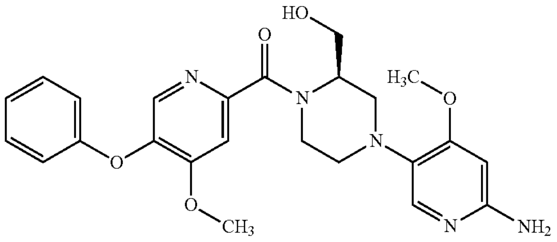 [SMILES: COc1cc(C(=O)N2CCN(c3cnc(N)cc3OC)C[C@@H]2CO)ncc1Oc1ccccc1] | [(R)-4-(6-Amino-4-methoxy-pyridin-3-yl)-2-hydroxymethyl-piperazin-1-yl]-(4-methoxy-5-phenoxy-pyridin-2-yl)-methanone |
| 70 | 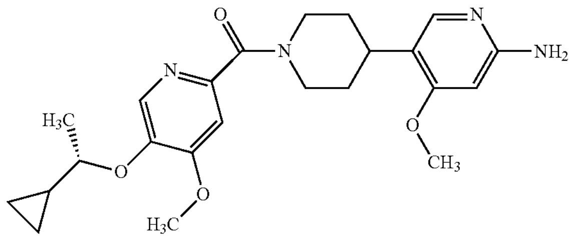 [SMILES: COc1cc(C(=O)N2CCC(c3cnc(N)cc3OC)CC2)ncc1O[C@@H](C)C1CC1] | (6-Amino-4-methoxy-3',4',5',6'-tetrahydro-2'H-[3,4']bipyridinyl-1'-yl)-[5-((S)-1-cyclopropyl-ethoxy)-4-methoxy-pyridin-2-yl]-methanone |
| 71 | 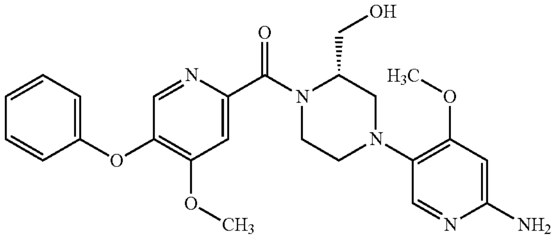 [SMILES: COc1cc(C(=O)N2CCN(c3cnc(N)cc3OC)C[C@H]2CO)ncc1Oc1ccccc1] | [(S)-4-(6-Amino-4-methoxy-pyridin-3-yl)-2-hydroxymethyl-piperazin-1-yl]-(4-methoxy-5-phenoxy-pyridin-2-yl)-methanone |

-continued

| Cpd No. | Structure | Compound Name |
| --- | --- | --- |
| 72 | 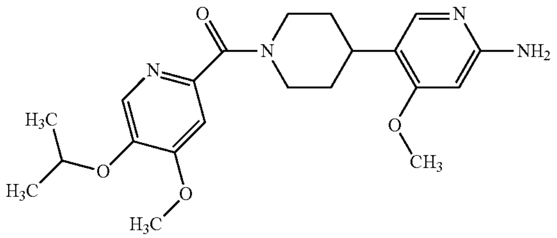 [SMILES: COc1cc(C(=O)N2CCC(c3cnc(N)cc3OC)CC2)ncc1OC(C)C] | (6-Amino-4-methoxy-3',4',5',6'-tetrahydro-2'H-[3,4']bipyridinyl-1'-yl)-(5-isopropoxy-4-methoxy-pyridin-2-yl)-methanone |
| 73 | 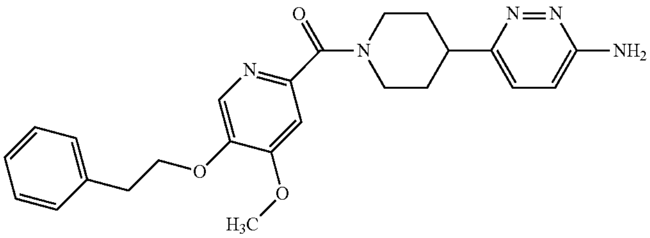 [SMILES: COc1cc(C(=O)N2CCC(c3ccc(N)nn3)CC2)ncc1OCCc1ccccc1] | [4-(6-Amino-pyridazin-3-yl)-piperidin-1-yl]-(4-methoxy-5-phenethyloxy-pyridin-2-yl)-methanone |
| 74 | 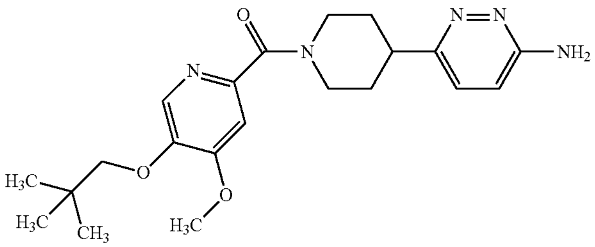 [SMILES: COc1cc(C(=O)N2CCC(c3ccc(N)nn3)CC2)ncc1OCC(C)(C)C] | [4-(6-Amino-pyridazin-3-yl)-piperidin-1-yl]-[5-(2,2-dimethyl-propoxy)-4-methoxy-pyridin-2-yl]-methanone |
| 75 | 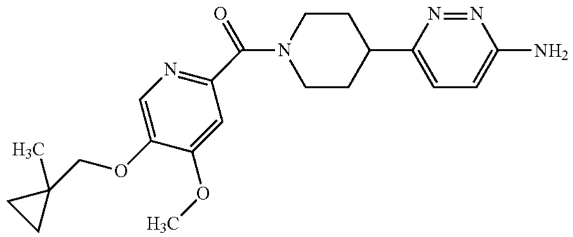 [SMILES: COc1cc(C(=O)N2CCC(c3ccc(N)nn3)CC2)ncc1OCC1(C)CC1] | [4-(6-Amino-pyridazin-3-yl)-piperidin-1-yl]-[4-methoxy-5-(1-methyl-cyclopropylmethoxy)-pyridin-2-yl]-methanone |
| 76 | 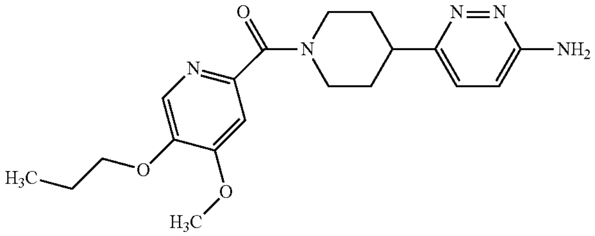 [SMILES: CCCOc1cnc(C(=O)N2CCC(c3ccc(N)nn3)CC2)cc1OC] | [4-(6-Amino-pyridazin-3-yl)-piperidin-1-yl]-(4-methoxy-5-propoxy-pyridin-2-yl)-methanone |
| 77 | 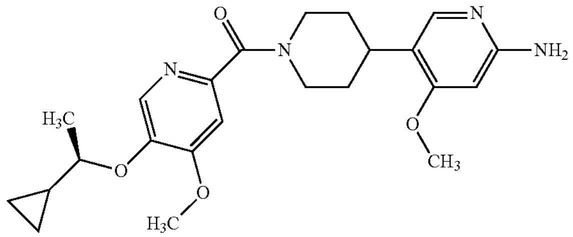 | (6-Amino-4-methoxy-3',4',5',6'-tetrahydro-2'H-[3,4']bipyridinyl-1'-yl)-[5-((R)-1-cyclopropyl-ethoxy)-4-methoxy-pyridin-2-yl]-methanone |

-continued

| Cpd No. | Structure | Compound Name |
| --- | --- | --- |
| 78 | 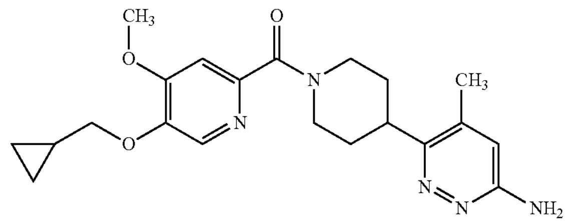 [SMILES: COc1cc(C(=O)N2CCC(c3nnc(N)cc3C)CC2)ncc1OCC1CC1] | [4-(6-Amino-4-methyl-pyridazin-3-yl)-piperidin-1-yl]-(5-cyclopropyl-methoxy-4-methoxy-pyridin-2-yl)-methanone |
| 79 | 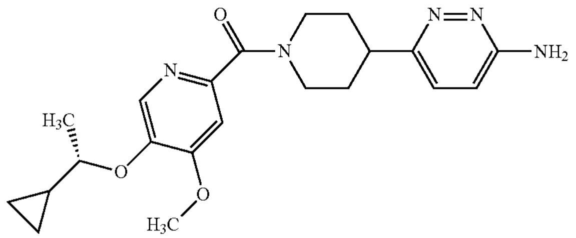 [SMILES: COc1cc(C(=O)N2CCC(c3ccc(N)nn3)CC2)ncc1O[C@@H](C)C1CC1] | [4-(6-Amino-pyridazin-3-yl)-piperidin-1-yl]-[5-((S)-1-cyclopropyl-ethoxy)-4-methoxy-pyridin-2-yl]-methanone |
| 80 | 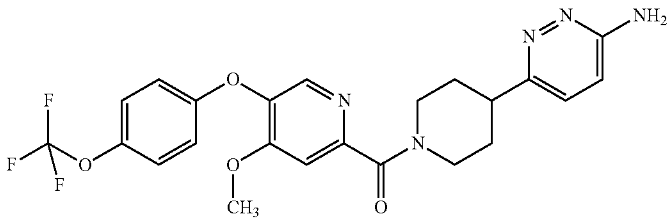 [SMILES: COc1cc(C(=O)N2CCC(c3ccc(N)nn3)CC2)ncc1Oc1ccc(OC(F)(F)F)cc1] | [4-(6-Amino-pyridazin-3-yl)-piperidin-1-yl]-[4-methoxy-5-(4-trifluoromethoxy-phenoxy)-pyridin-2-yl]-methanone |
| 81 | 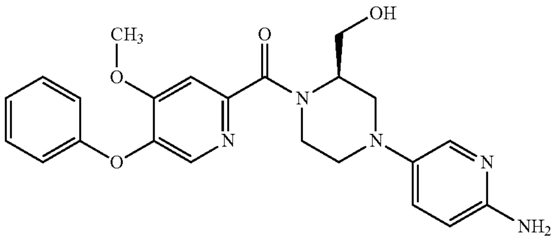 [SMILES: COc1cc(C(=O)N2CCN(c3ccc(N)nc3)C[C@@H]2CO)ncc1Oc1ccccc1] | [(R)-4-(6-Amino-pyridin-3-yl)-2-hy-droxymethyl-piperazin-1-yl]-(4-methoxy-5-phenoxy-pyridin-2-yl)-methanone |
| 82 | 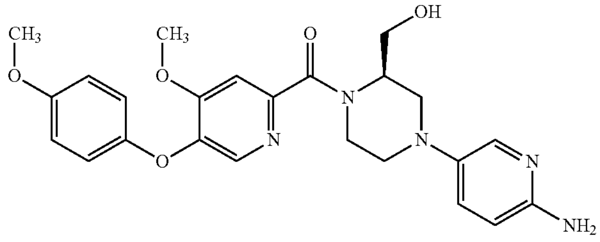 [SMILES: COc1ccc(Oc2cnc(C(=O)N3CCN(c4ccc(N)nc4)C[C@@H]3CO)cc2OC)cc1] | [(R)-4-(6-Amino-pyridin-3-yl)-2-hy droxymethyl-piperazin-1-yl]-[4-methoxy-5-(4-methoxy-phenoxy)-pyridin-2-yl]-methanone |
| 83 | 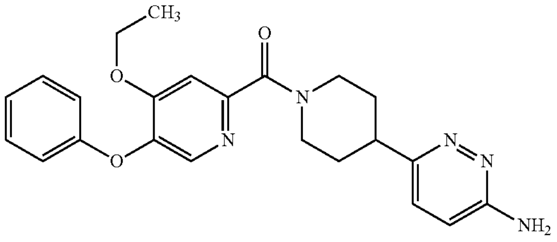 [SMILES: CCOc1cc(C(=O)N2CCC(c3ccc(N)nn3)CC2)ncc1Oc1ccccc1] | [4-(6-Amino-pyridazin-3-yl)-piperidin-1-yl]-[5-(phenoxy)-4-ethoxy-pyridin-2-yl]-methanone |

-continued

| Cpd No. | Structure | Compound Name |
|---|---|---|
| 84 | 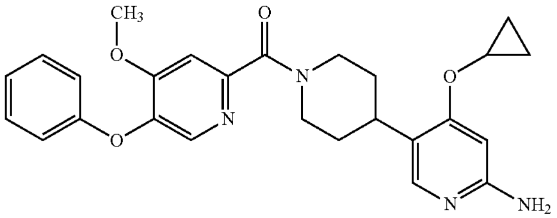 [SMILES: COc1cc(C(=O)N2CCC(c3cnc(N)cc3OC3CC3)CC2)ncc1Oc1ccccc1] | (6-Amino-4-cyclopropoxy-3',4',5',6'-tetrahydro-2'H-[3,4']bipyridinyl-1'-yl)-[5-(phenoxy)-4-methoxy-pyridin-2-yl]-methanone |
| 85 | 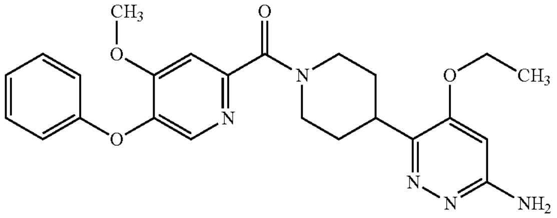 [SMILES: CCOc1cc(N)nnc1C1CCN(C(=O)c2cc(OC)c(Oc3ccccc3)cn2)CC1] | [4-(6-Amino-4-ethoxy-pyridazin-3-yl)-piperidin-1-yl]-[4-methoxy-5-(phenoxy)-pyridin-2-yl]-methanone |
| 86 | 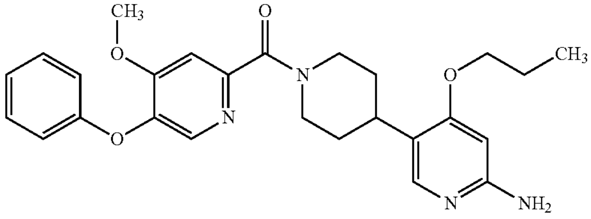 [SMILES: CCCOc1cc(N)ncc1C1CCN(C(=O)c2cc(OC)c(Oc3ccccc3)cn2)CC1] | (6-Amino-4-propoxy-3',4,5',6'-tetrahydro-2'H-[3,4']bipyridinyl-1'-yl)-[5-(phenoxy)-4-methoxy-pyridin-2-yl]-methanone |
| 87 | 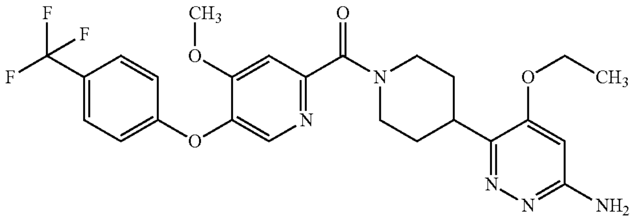 [SMILES: CCOc1cc(N)nnc1C1CCN(C(=O)c2cc(OC)c(Oc3ccc(C(F)(F)F)cc3)cn2)CC1] | 5-Ethoxy-6-(1-{4-methoxy-5-[4-(trifluoromethyl)phenoxy]pyridine-2-carbonyl}piperidin-4-yl)pyridazin-3-amine |
| 88 | 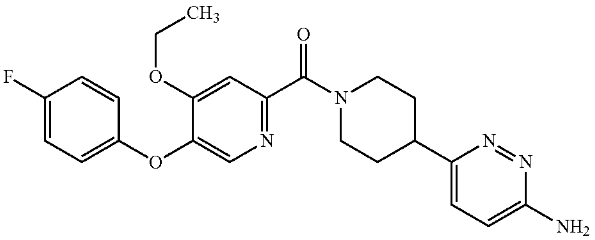 [SMILES: CCOc1cc(C(=O)N2CCC(c3ccc(N)nn3)CC2)ncc1Oc1ccc(F)cc1] | [4-(6-Amino-pyridazin-3-yl)-piperidin-1-yl]-[5-(4-fluoro-phenoxy)-4-ethoxy-pyridin-2-yl]-methanone |
| 89 | 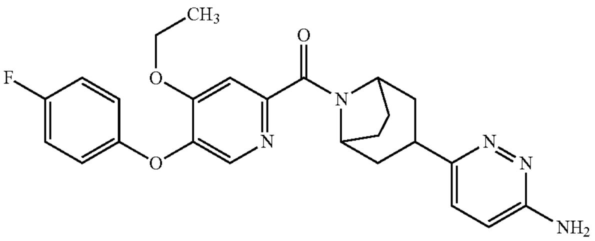 [SMILES: CCOc1cc(C(=O)N2C3CCC2CC(c2ccc(N)nn2)C3)ncc1Oc1ccc(F)cc1] | [3-(6-Amino-pyridazin-3-yl)-8-aza-bicyclo[3.2.1]oct-8-yl]-[4-ethoxy-5-(4-fluoro-phenoxy)-pyridin-2-y l]-methanone |

-continued

| Cpd No. | Structure | Compound Name |
|---|---|---|
| 90 | 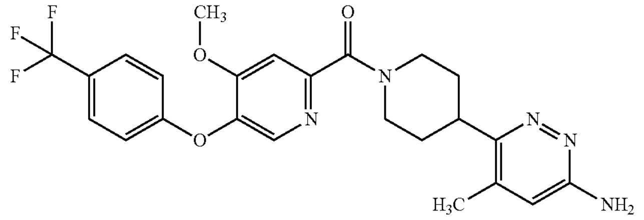 [SMILES: COc1cc(C(=O)N2CCC(c3nnc(N)cc3C)CC2)ncc1Oc1ccc(C(F)(F)F)cc1] | 6-(1-{4-Methoxy-5-[4-(trifluoro-methyl)phenoxy]pyridine-2-carbonyl}piperidin-4-yl)-5-methyl-pyridazin-3-amine |
| 91 | 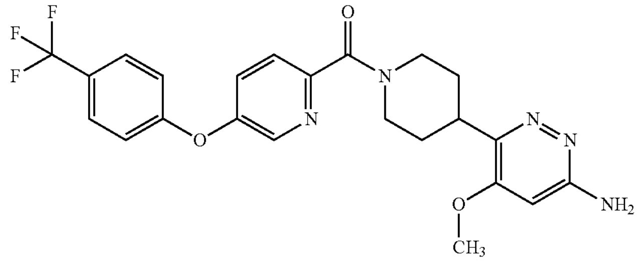 [SMILES: COc1cc(N)nnc1C1CCN(C(=O)c2ccc(Oc3ccc(C(F)(F)F)cc3)cn2)CC1] | 5-Methoxy-6-(l-{5-[4-(trifluoro-methyl)-phenoxy]-pyridine-2-carbonyl}piperidin-4-yl)-pyridazin-3-amine |
| 92 | 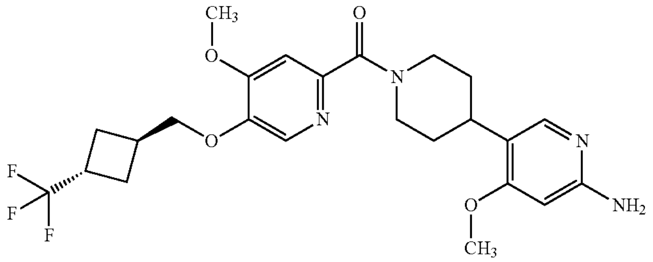 [SMILES: COc1cc(C(=O)N2CCC(c3cnc(N)cc3OC)CC2)ncc1OC[C@H]1C[C@H](C(F)(F)F)C1] | 4-Methoxy-5-[1-(4-methoxy-5-{[trans-3-(trifluoromethyl)cyclobutyl]-methoxy}pyridine-2-carbonyl)-piperidin-4-yl]pyridin-2-amine |
| 93 | 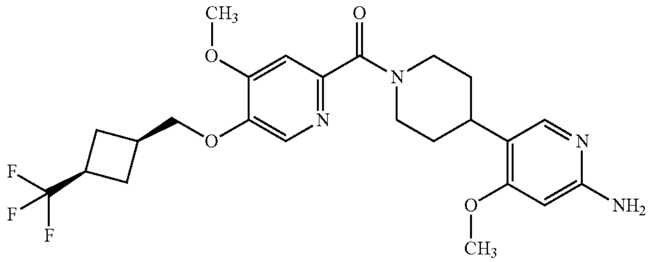 [SMILES: COc1cc(C(=O)N2CCC(c3cnc(N)cc3OC)CC2)ncc1OC[C@H]1C[C@@H](C(F)(F)F)C1] | 4-Methoxy-5-[1-(4-methoxy-5-{[(cis-3-(trifluoromethyl)-cyclobutyl]methoxy}-pyridine-2-carbonyl)piperidin-4-yl]pyridin-2-amine |
| 94 | 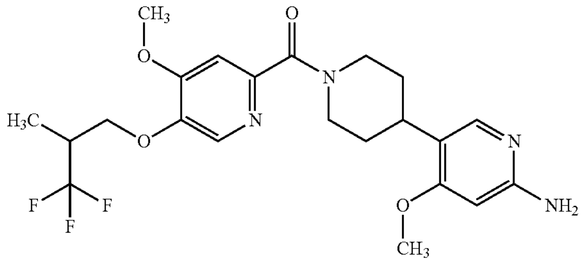 [SMILES: COc1cc(C(=O)N2CCC(c3cnc(N)cc3OC)CC2)ncc1OCC(C)C(F)(F)F] | 4-Methoxy-5-(1-{4-methoxy-5-[(2)-3,3,3-trifluoro-2-methylpropoxy]-pyridine-2-carbonyl}piperidin-4-yl)pyridin-2-amine |

-continued

| Cpd No. | Structure | Compound Name |
| --- | --- | --- |
| 95 | 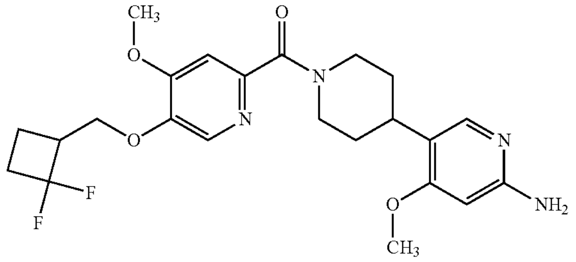 [SMILES: COc1cc(C(=O)N2CCC(c3cnc(N)cc3OC)CC2)ncc1OCC1CCC1(F)F] | 5-(1-{5-[(2,2-Difluorocyclobutyl)-methoxy]-4-methoxy-pyridine-2-carbonyl}-piperidin-4-yl)-4-methoxypyridin-2-amine |

or a pharmaceutically acceptable salt thereof.

4. The method of claim 1, wherein the TRPC6 inhibitor is administered in combination with one or more additional therapeutic agents selected from the group consisting of antimalarials, virostatic nucleoside analogs, HIV-protease inhibitors, angiotensin II receptor antagonists, angiotensin converting enzyme inhibitors, CGRP antagonists, anticoagulants, antidiabetics, bronchodilators, and steroids.

5. The method of claim 1, wherein the TRPC6 inhibitor is administered in combination with one or more additional therapeutic agents selected from the group consisting of one or more monoclonal antibodies that block infectivity of SARS-CoV-2, anti-IL-6 antibodies, kinase inhibitors providing immunomodulatory effects, and antifibrotics.

6. The method of claim 3, wherein the TRPC6 inhibitor is [4-(6-Amino-pyridazin-3-yl)-piperidin-1-yl]-[5-(4-isopropoxy-phenoxy)-4-methoxy-pyridin-2-yl]-methanone (6), or a pharmaceutically acceptable salt thereof.

7. The method of claim 3, wherein the TRPC6 inhibitor is [4-(6-Amino-pyridazin-3-yl)-piperidin-1-yl]-(4-methoxy-5-phenoxy-pyridin-2-yl)-methanone (16), or a pharmaceutically acceptable salt thereof.

8. The method of claim 3, wherein the TRPC6 inhibitor is [4-(6-Amino-pyridazin-3-yl)-piperidin1-yl]-[5-(4-fluoro-phenoxy)-4-methoxy-pyridin-2-yl]-methanone (17), or a pharmaceutically acceptable salt thereof.

9. The method of claim 3, wherein the TRPC6 inhibitor is [4-(6-Amino-pyridazin-3-yl)-piperidin-1-yl]-[5-(4-difluoromethoxy-phenoxy)-4-methoxy-pyridin-2-yl]-methanone (54), or a pharmaceutically acceptable salt thereof.

10. The method of claim 3, wherein the TRPC6 inhibitor is [4-(6-Amino-pyridazin-3-yl)-piperidin-1-yl]-[4-methoxy-5-(4-trifluoromethoxy-phenoxy)-pyridin-2-yl]-methanone (80), or a pharmaceutically acceptable salt thereof.

11. The method of claim 3, wherein the TRPC6 inhibitor is [4-(6-Amino-pyridazin-3-yl)-piperidin-1-yl]-[5-(phenoxy)-4-ethoxy-pyridin-2-yl]-methanone (83), or a pharmaceutically acceptable salt thereof.

12. The method of claim 3, wherein the TRPC6 inhibitor is the pharmaceutically acceptable salt of [4-(6-Amino-pyridazin-3-yl)-piperidin-1-yl]-[5-(4-isopropoxy-phenoxy)-4-methoxy-pyridin-2-yl]-methanone (6).

13. The method of claim 3, wherein the TRPC6 inhibitor is the pharmaceutically acceptable salt of [4-(6-Amino-pyridazin-3-yl)-piperidin-1-yl]-(4-methoxy-5-phenoxy-pyridin-2-yl)-methanone (16).

14. The method of claim 3, wherein the TRPC6 inhibitor is the pharmaceutically acceptable salt of [4-(6-Amino-pyridazin-3-yl)-piperidin 1-yl]-[5-(4-fluoro-phenoxy)-4-methoxy-pyridin-2-yl]-methanone (17).

15. The method of claim 3, wherein the TRPC6 inhibitor is the pharmaceutically acceptable salt of [4-(6-Amino-pyridazin-3-yl)-piperidin-1-yl]-[5-(4-difluoromethoxy-phenoxy)-4-methoxy-pyridin-2-yl]-methanone (54).

16. The method of claim 3, wherein the TRPC6 inhibitor is the pharmaceutically acceptable salt of [4-(6-Amino-pyridazin-3-yl)-piperidin-1-yl]-[4-methoxy-5-(4-trifluoromethoxy-phenoxy)-pyridin-2-yl]-methanone (80).

17. The method of claim 3, wherein the TRPC6 inhibitor is the pharmaceutically acceptable salt of [4-(6-Amino-pyridazin-3-yl)-piperidin-1-yl]-[5-(phenoxy)-4-ethoxy-pyridin-2-yl]-methanone (83).

18. The method of claim 3, wherein the TRPC6 inhibitor is [4-(6-Amino-pyridazin-3-yl)-piperidin-1-yl]-[5-(4-isopropoxy-phenoxy)-4-methoxy-pyridin-2-yl]-methanone (6).

19. The method of claim 3, wherein the TRPC6 inhibitor is [4-(6-Amino-pyridazin-3-yl)-piperidin-1-yl]-(4-methoxy-5-phenoxy-pyridin-2-yl)-methanone (16).

20. The method of claim 3, wherein the TRPC6 inhibitor is [4-(6-Amino-pyridazin-3-yl)-piperidin1-yl]-[5-(4-fluoro-phenoxy)-4-methoxy-pyridin-2-yl]-methanone (17).

21. The method of claim 3, wherein the TRPC6 inhibitor is [4-(6-Amino-pyridazin-3-yl)-piperidin-1-yl]-[5-(4-difluoromethoxy-phenoxy)-4-methoxy-pyridin-2-yl]-methanone (54).

22. The method of claim 3, wherein the TRPC6 inhibitor is [4-(6-Amino- pyridazin-3-yl)-piperidin-1-yl]-[4-methoxy-5-(4-trifluoromethoxy-phenoxy)-pyridin-2-yl]-methanone (80).

23. The method of claim 3, wherein the TRPC6 inhibitor is [4-(6-Amino-pyridazin-3-yl)-piperidin-1-yl]-[5-(phenoxy)-4-ethoxy-pyridin-2-yl]-methanone (83).

* * * * *